United States Patent
Eberwine et al.

(10) Patent No.: US 9,260,703 B2
(45) Date of Patent: Feb. 16, 2016

(54) METHODS OF DETECTING TRANSCRIPTION

(75) Inventors: James H Eberwine, Philadelphia, PA (US); Ulo Langel, Bandhagen (SE); Emelia Eiriksdottir, Stockholm (SE); Tina Peritz, Philadelphia, PA (US); Jai-Yoon Sul, Bensalem, PA (US); Philip G. Haydon, Boston, MA (US); Junhyong Kim, Narberth, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1953 days.

(21) Appl. No.: 11/920,618

(22) PCT Filed: May 17, 2006

(86) PCT No.: PCT/US2006/019107
§ 371 (c)(1),
(2), (4) Date: Jul. 24, 2009

(87) PCT Pub. No.: WO2006/125012
PCT Pub. Date: Nov. 23, 2006

(65) Prior Publication Data
US 2010/0041025 A1 Feb. 18, 2010

Related U.S. Application Data

(60) Provisional application No. 60/682,334, filed on May 18, 2005.

(51) Int. Cl.
C12Q 1/68 (2006.01)
C12N 9/12 (2006.01)

(52) U.S. Cl.
CPC .............. *C12N 9/127* (2013.01); *C12N 9/1247* (2013.01); *C12Q 1/68* (2013.01); *C07K 2319/72* (2013.01); *C07K 2319/73* (2013.01); *C07K 2319/85* (2013.01)

(58) Field of Classification Search
CPC ....................................................... C12Q 1/68
USPC ........................................................ 435/6.1
See application file for complete search history.

(56) References Cited

U.S. PATENT DOCUMENTS

| | | | |
|---|---|---|---|
| 5,843,730 A * | 12/1998 | Wain-Hobson et al. | 435/91.1 |
| 6,251,303 B1 | 6/2001 | Bawendi et al. | |
| 6,319,426 B1 | 11/2001 | Bawendi et al. | |
| 6,322,901 B1 | 11/2001 | Bawendi et al. | |
| 6,423,551 B1 | 7/2002 | Weiss et al. | |
| 6,426,513 B1 | 7/2002 | Bawendi et al. | |
| 6,444,143 B2 | 9/2002 | Bawendi et al. | |
| 6,576,291 B2 | 6/2003 | Bawendi et al. | |
| 2002/0025317 A1 * | 2/2002 | Leung et al. | 424/145.1 |
| 2003/0059822 A1 * | 3/2003 | Chan et al. | 435/6 |
| 2003/0165434 A1 * | 9/2003 | Reinhard et al. | 424/45 |
| 2003/0175790 A1 * | 9/2003 | Case | 435/6 |
| 2004/0053399 A1 * | 3/2004 | Gilmanshin | 435/252.3 |
| 2006/0217892 A1 * | 9/2006 | Heilper et al. | 702/19 |

OTHER PUBLICATIONS

Ostrander et al. Template Supercoiling by a Chimera of Yeast GAL4 Protein and Phage T7 RNA Polymerase. Science (1990) 249: 1261-1265.*
Soomets et al. Biochimica et Biophysica Acta (BBA)—Biomembranes (2000) 1467(1): 165-176.*
Braun et al. (2002) Journal of Molecular Biology, vol. 318, pp. 237-243.*
Ortiz et al., "PNA molecular beacons for rapid detection of PCR amplicons", Molecular and Cellular Probes (1998) 12, 219-226.
Del Poeta et al., "*Cryptococcus neoformans* Differential Gene Expression Detected In Vitro and In Vivo with Green Fluorescent Protein", Infection and Immunity, Apr. 1999, 1812-1820.
Ziemiecki et al., "Oncogenic activation of the human *trk* proto-oncogene by recombination with the ribosomal large subunit protein L7a," The EMBO Journal, 1990, 9(1):191-196.
Ostrander et al., "Template Supercoiling by a Chimera of Yeast *GAL4* Protein and Phase T7 RNA Polymerase," *Science*, Sep. 1990, 249:1261-1265.
Examiner's Report issued in Australian Application No. 2006247215, dated Dec. 8, 2010.
Adams, et al., 1991, Science 252: 1651-1656.
Alwine et al., 1977, Proc. Nat'l Acad. Sci. USA 74: 5350-5354.
Bell et al. 2002, Biophys. J. 83: 1050-1073.
Berk and Sharp, 1977, Cell 12: 721-732.
Duggan et al., 1999, Nat Genet. 21(1 Suppl):10-14.
Egholm et al., 1992, J. Am. Chem. Soc. 114, pp. 1895-1897.
Eiríksdóttir et al. 2004, Drug Design Reviews, 1:161-173.
Hällbrink et al., 2001, Biochim. Biophys. Acta. 1515:101-109.
Hanvey et al., 1992, Science 258, 1481-1485.
Haustein et al., 2004, Curr. Opin. Struct. Biol. 14: 531-540.
Järver, 2004, Drug Discov. Today 9: 395-402.
Korn et al., 2003, Nucleic Acid Res., 31(16): e89.
Liang and Pardee, 1992, Science 257: 967-971.
Lockhart, et al., 1996, Nature Biotechnol. 14: 1675-1680.
Nair et al. 2003, Nucleic Acid Research 31:397-399.
Nielsen et al., 1991, Science 254,1497-1500.
Okubo, et al., 1992, Nature Genet. 2: 173-179.
Pooga et al., 1998, FASEB J. 12: 67-77.
Pooga et al., 2001 Curr. Cancer Drug Targets 1: 231-239.
Pooga et al., 2001, FASEB J. 15: 1451-1453.
Schena, et al., 1995, Science 270: 467-470.
Schena, et al., 1996, Proc. Natl Acad. Sci. USA 93: 10614-10619.
van der Heide et al., 2000 Biophys J., 78: 2138-2150.
Velculescu et al., 1995, Science 270: 484-487.

* cited by examiner

*Primary Examiner* — Angela M Bertagna
(74) *Attorney, Agent, or Firm* — Riverside Law LLP

(57) ABSTRACT

The present invention includes compositions, methods and kits for the real-time detection of transcription and translation in live cells, tissues and organisms. The present invention further provides method for the rapid sequencing of nucleic acids without using conventional sequencing techniques or reactions.

33 Claims, 35 Drawing Sheets

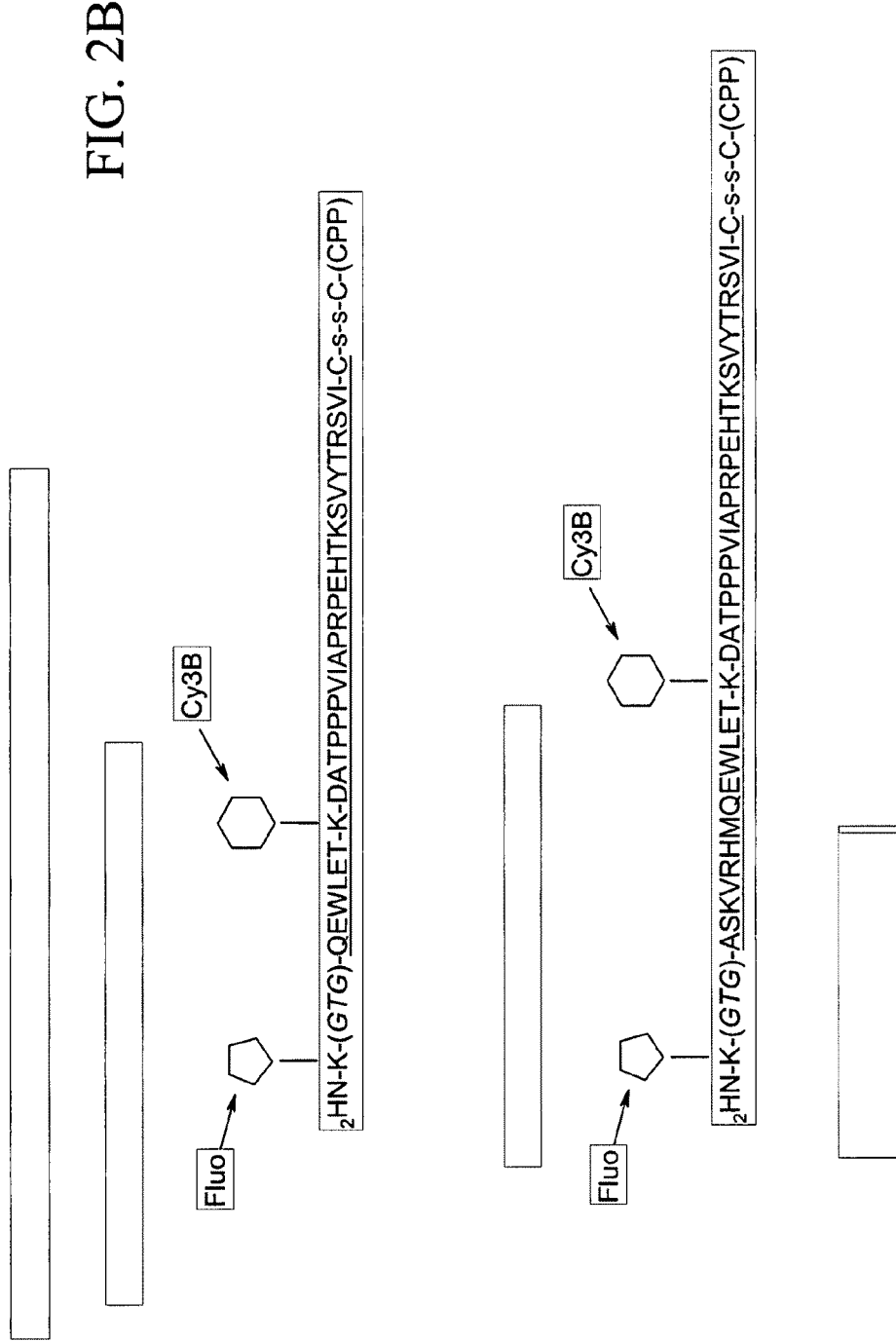

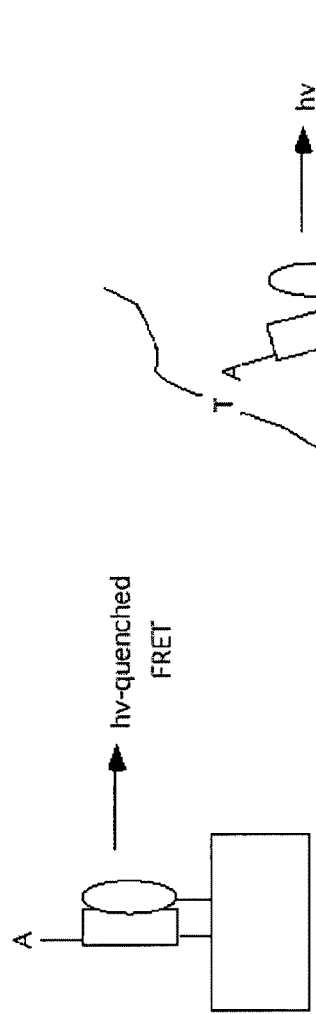
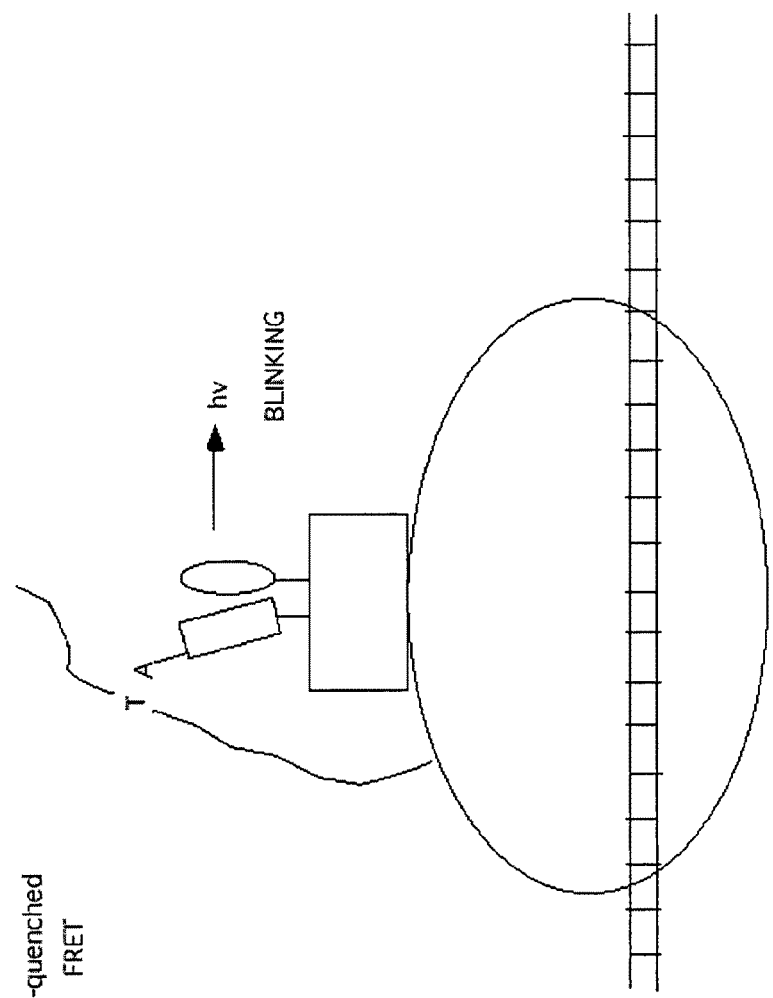
FIG. 6
FIG. 7

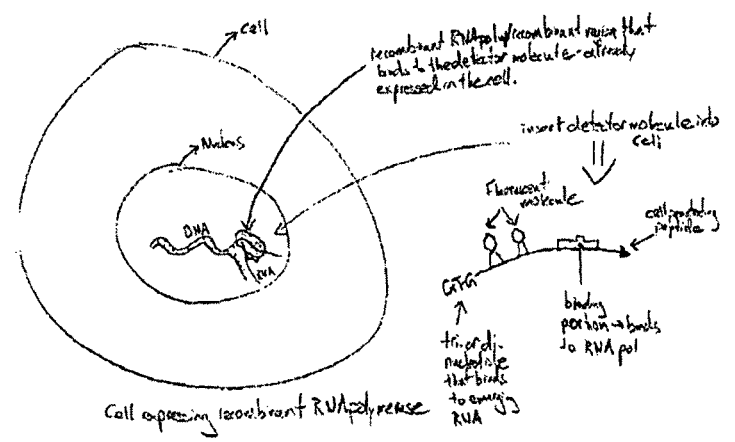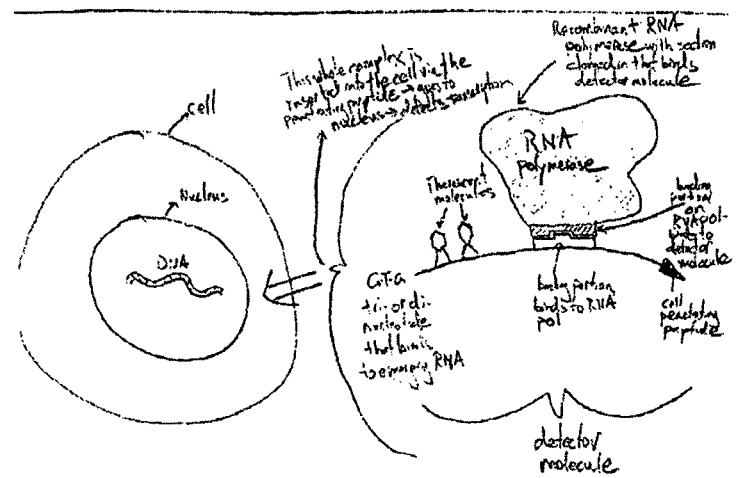
FIG. 8 atgactgata acgccaacag ccaactggta gtacgagcca
agtttaactt ccagcagacc aatgaagatg agctctcctt
ctcgaagggt gacgtcatcc atgtcactcg agtggaggaa
ggaggctggt gggaaggcac acacaatggc aggaccggct
ggttccccag caactacgta cgagagatc

MTDNANSQLVVRAKFNFQQTNE
DELSFSKGDVIHVTRVEEGGWW
EGTHNGRTGWFPSNYVREI

FIG. 25

FIG. 26 atgaacacga ttaacatgc taagaacgac ttcctgaca tcgaactggc tgctatcccg ttcaacactc tggctgacca ttacggtgag cgtttagctc
gcgaacagtt ggcccttgag catgagtctt acgagatggg tgaagcacgc ttccgcaaga tgttgagcg tcaacttaaa gctggtgagg
ttgcggataa cgctgccgcc aagcctctca tcactaccct actccctaag atgatgcac gcatcaacga ctggtttgag gaagtgaaag
ctaagcgcgg caagcgcccg acagccttcc agttcctgca agaaatcaag cggaagccg tagcgtacat ccggagcacgt caccattaag accactctgg
cttgcctaac cagtgctgac aatacaaccg ttcaggtgt agcaagcgca atcggtcgg ccattgagga cgaggctgc ttcggtcgta
tccgtgacct tgaagctaag cacttcaaga aaaacgttga gtctactcgg gtctactagg aacaagcgcg tagggcacgt ctacaagaaa gcatttatgc
aagttgtcga ggctgacatg ctctctaagg attgagtcaa cggaatggt tagcttacac cgccaaaatg ctggcgtagt aggtcaagac tctgagacta
tacgctgcat cgagatgctc attgagtcaa cggaatggt tagcttacac cgccaaaatg ctggcgtagt aggtcaagac tctgagacta
tcgaactgc acctgaatac gctgaggcta tcgcaacccg tgcaggtgcg cgtgtcctc tgctctccgat gttccaacct tgcgtagttc
ctcctaagcc gtggactggc attactggtg gtggctattg ggctaacggt cgtgtcctc tggcgtggt gcgtactcac agtaagaaag
cactgatgcg ctacgaagac gtttacatgc ctgaggtgta caaagcgatt aacattgcgc aaaaccgc atggaaaatc aacaagaaag
tcctagcgt cgccaacgta atcaccaagt ggaagcattg tccggtcgag gacatccctg cgattgagcg cgatgagcg ccgatgaaac
cggaagacat cgacatgaat cctgaggctc tcaccgcgtg gaaacgtgct gccgctgctg tgtaccgcaa ggacaaggct cgcaagtctc
gccgtacag ccttgagttc atgcttgagc aagccaataa gttgctaac cataaggca tctggttccc ttacaacatg gactggcgcg gtcgtgtta
cgctgtgtca atgttcaacc cgcaaggtaa cgcaaggtgtc tgcgggtgtc cgatatgacc aaaggactgc ttacgctggc gaaagtaaa ccaatcggta aggaagtta
ctactggctg aaaatccacg gcttcaaactg gtcaaaactg tgcgggtgtc gataaggttc cgttccctga gcgcatcaag ggcgcatcaag ttcattgagg aaaaccacga
gaacatcatg gcttgcgcta agtcccact ggagaacatgc tcccttccgc ggagaacatgc tggttcgga cgggtcttgc tctggcatcc agcacttctc cgcgatgctc
gtacagcacc acggcctgag ctataactgc tcccttccgc ttgctcta gtgaaaccgt tcaggacatc tcaggacgt gacgatgag aacactggtg ttgctaagaa agtcaacgag
cgagatgagg taggtgttcg cgcggttaac ttgctcta gataacgaag tagttaccgt gttactcg cagtgtgact aagcgttcag tcatgacgct ggcttacggg
attctacaag cagacgcaat caatgggacc gataacgaag tagttaccgt gttactcg cagtgtgact aagcgttcag tcatgacgct ggcttacggg
ctgggcacta aggcactggc tggtcaatgg ctgctacg ctggaagata ccattcagcc agcattgat tccggcaagg gtctgatgtt cactcagccg
tccaaagagt tcggcttccg tcaacaagtg cggctaagctg attggaat ctgtgagcgt gacggtggta gctgcggttg aagcaatgaa ctggcttaag
aatcaggctg ctggatacat ggctaagctg tgctgagtc aaagataaga agctgcttc gaacctgatg tatcgctcct aacttgacc aagccaaga cggtagccac
gatggtttcc cgtgtgca ggaatacaag cagcctattc gcacacaaac aggagtctgg tcgaatcttt tgcactgatt cacgactcct tcggtaccat tccggctgac
attaacacca acaaagatag cgagattgat gcacacaaac aggagtctgg tcgaatcttt tgcactgatt cacgactcct tcggtaccat tccggctgac
cttcgtaaga ctgtagttg ggcacacgag agtacggaa tcgaatcttt tgcactgatt cacgactcct tcggtaccat tccggctgac
gctgcgaacc tgttcaaagc agtgcgcgaa actatggttg acacatga agtgctaa aggtaacttg aacctccgtg acatcttaga gtcggacttc gcgttcgcgt a
acgagtctca attggacaaa atgccagcac tccggctaa aggtaacttg aacctccgtg acatcttaga gtcggacttc gcgttcgcgt a MNTINIAKNDFSDIELAAIPFNTLADHYGERLAREQLALEHESYEMGEARFRKMFERQLK
AGEVADNAAAKPLITTLLPKMIARINDWFEEVKAKRGKRPTAFQFLQEIKPEAVAYITIK
TTLACLTSADNTTVQAVASAIGRAIEDEARFGRIRDLEAKHFKKNVEEQLNKRVGHVYKK
AFMQVVEADMLSKGLLGGEAWSSWHKEDSIHVGVRCIEMLIESTGMVSLHRQNAGVVGQD
SETIELAPEYAEAIATRAGALAGISPMFQPCVVPPKPWTGITGGGYWANGRRPLALVRTH
SKKALMRYEDVYMPEVYKAINIAQNTAWKINKKVLAVANVITKWKHCPVEDIPAIEREEL
PMKPEDIDMNPEALTAWKRAAAAVYRKDKARKSRRISLEFMLEQANKFANHKAIWFPYNM
DWRGRVYAVSMFNPQGNDMTKGLLTLAKGKPIGKEGYYWLKIHGANCAGVDKVPFPERIK
FIEENHENIMACAKSPLENTWWAEQDSPFCFLAFCFEYAGVQHHGLSYNCSLPLAFDGSC
SGIQHFSAMLRDEVGGRAVNLLPSETVQDIYGIVAKKVNEILQADAINGTDNEVVTVTDE
NTGEISEKVKLGTKALAGQWLAYGVTRSVTKRSVMTLAYGSKEFGFRQQVLEDTIQPAID
SGKGLMFTQPNQAAGYMAKLIWESVSVTVVAAVEAMNWLKSAAKLLAAEVKDKKTGEILR
KRCAVHWVTPDGFPVWQEYKKPIQTRLNLMFLGQFRLQPTINTNKDSEIDAHKQESGIAP
NFVHSQDGSHLRKTVVWAHEKYGIESFALIHDSFGTIPADAANLFKAVRETMVDTYESCD
VLADFYDQFADQLHESQLDKMPALRLKVTTSVTSSRTSRSR

FIG. 27

DATPPPVIAPRPEHTKSVYTRSVI

| scan | peptide | linking | excitation | DNA | Data Call |
|---|---|---|---|---|---|
| 1 | 1 | codelink | 488 | act | ACT |
| 2 | 1 | codelink | 488 & 543 | act | ACT |
| 5 | 1 | codelink | 488 | pgem | No Decision |
| 6 | 1 | codelink | 488 & 543 | pgem | PGEM |
| 10 | 1 | codelink | 488 & 543 | pgem | PGEM |
| 13 | 2 | codelink | 488 | act | ACT |
| 14 | 2 | codelink | 488 & 543 | act | ACT |
| 17 | 2 | codelink | 488 | pgem | ACT |
| 18 | 2 | codelink | 488 & 543 | pgem | No Decision |
| 22 | 2 | codelink | 488 & 543 | pgem | ACT |
| 25 | 3 | codelink | 488 | act | ACT |
| 26 | 3 | codelink | 488 & 543 | act | ACT |
| 29 | 3 | codelink | 488 | pgem | ACT |
| 30 | 3 | codelink | 488 & 543 | pgem | PGEM |

SEQUENCE LISTING

<160> NUMBER OF SEQ ID NOS: 60

<210> SEQ ID NO 1
<211> LENGTH: 2650
<212> TYPE: DNA
<213> ORGANISM: Bacteriophage T7

<400> SEQUENCE: 1

```
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
cacttcaaga aaacgttga ggaacaactc aacaagcgcg tagggcacgt ctacaagaaa     540
gcatttatgc aagttgtcga ggctgacatg ctctctaagg gtctactcgg tggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgcgtagttc ctcctaagcc gtggactggc     840
attactggtg gtggctattg ggctaacggt cgtcgtcctc tggcgctggt gcgtactcac     900
agtaagaaag cactgatgcg ctacgaagac gtttacatgc tgaggtgta caaagcgatt     960 aacattgcgc aaaacaccgc atggaaaatc aacaagaaag tcctagcggt cgccaacgta    1020
atcaccaagt ggaagcattg tccggtcgag gacatccctg cgattgagcg tgaagaactc    1080
ccgatgaaac cggaagacat cgacatgaat cctgaggctc tcaccgcgtg gaaacgtgct    1140
gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
```

```
gactggcgcg gtcgtgttta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gataaggttc cgttccctga gcgcatcaag    1440
ttcattgagg aaaaccacga gaacatcatg gcttgcgcta agtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga aaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggttttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac tccggctaaa ggtaacttga acctccgtga catcttagag tcggacttcg    2640
cgttcgcgta                                                          2650

<210> SEQ ID NO 2
<211> LENGTH: 189
<212> TYPE: DNA
<213> ORGANISM: Rattus norvegicus
<220> FEATURE:
<221> NAME/KEY: misc_feature
<222> LOCATION: (1)..(189)
<223> OTHER INFORMATION: nucleotides 1-189 of beta-PIX coding sequence

<400> SEQUENCE: 2
atgactgata acgccaacag ccaactggta gtacgagcca gtttaacttc cagcagacc     60 aatgaagatg agctctcctt ctcgaagggt gacgtcatcc atgtcactcg agtggaggaa    120
ggaggctggt gggaaggcac acacaatggc aggaccggct ggttccccag caactacgta    180
cgagagatc                                                           189

<210> SEQ ID NO 3
<211> LENGTH: 881
<212> TYPE: PRT
<213> ORGANISM: Bacteriophage T7

<400> SEQUENCE: 3

Met Asn Thr Ile Asn Ile Ala Lys Asn Asp Phe Ser Asp Ile Glu Leu
1               5                   10                  15
```

-continued

```
Ala Ala Ile Pro Phe Asn Thr Leu Ala Asp His Tyr Gly Glu Arg Leu
             20                  25                  30

Ala Arg Glu Gln Leu Ala Leu Glu His Glu Ser Tyr Glu Met Gly Glu
         35                  40                  45

Ala Arg Phe Arg Lys Met Phe Glu Arg Gln Leu Lys Ala Gly Glu Val
     50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                 85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365

Met Asn Pro Glu Ala Leu Thr Ala Trp Lys Arg Ala Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
```

```
                435                 440                 445
Gly Lys Pro Ile Gly Lys Glu Gly Tyr Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
                500                 505                 510

Ala Phe Cys Phe Glu Tyr Ala Gly Val Gln His Gly Leu Ser Tyr
                515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
                580                 585                 590

Glu Val Val Thr Val Thr Asp Glu Asn Thr Gly Glu Ile Ser Glu Lys
                595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
                660                 665                 670

Ala Ala Gly Tyr Met Ala Lys Leu Ile Trp Glu Ser Val Ser Val Thr
                675                 680                 685

Val Val Ala Ala Val Glu Ala Met Asn Trp Leu Lys Ser Ala Ala Lys
                690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
                740                 745                 750

Gly Gln Phe Arg Leu Gln Pro Thr Ile Asn Thr Asn Lys Asp Ser Glu
                755                 760                 765

Ile Asp Ala His Lys Gln Glu Ser Gly Ile Ala Pro Asn Phe Val His
                770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
                835                 840                 845

Phe Ala Asp Gln Leu His Glu Ser Gln Leu Asp Lys Met Pro Ala Leu
                850                 855                 860
```

```
Arg Leu Lys Val Thr Thr Ser Val Thr Ser Ser Arg Thr Ser Arg Ser
865                 870                 875                 880

Arg

<210> SEQ ID NO 4
<211> LENGTH: 63
<212> TYPE: PRT
<213> ORGANISM: Rattus norvegicus
<220> FEATURE:
<221> NAME/KEY: DOMAIN
<222> LOCATION: (1)..(63)
<223> OTHER INFORMATION: SH3 domain
<220> FEATURE:
<221> NAME/KEY: MISC_FEATURE
<222> LOCATION: (1)..(63)
<223> OTHER INFORMATION: residues 1-63 of beta-PIX

<400> SEQUENCE: 4

Met Thr Asp Asn Ala Asn Ser Gln Leu Val Val Arg Ala Lys Phe Asn
1               5                   10                  15

Phe Gln Gln Thr Asn Glu Asp Glu Leu Ser Phe Ser Lys Gly Asp Val
            20                  25                  30

Ile His Val Thr Arg Val Glu Glu Gly Gly Trp Trp Glu Gly Thr His
        35                  40                  45

Asn Gly Arg Thr Gly Trp Phe Pro Ser Asn Tyr Val Arg Glu Ile
    50                  55                  60

<210> SEQ ID NO 5
<211> LENGTH: 24
<212> TYPE: PRT
<213> ORGANISM: Rattus rattus
<220> FEATURE:
<221> NAME/KEY: MISC_FEATURE
<222> LOCATION: (1)..(24)
<223> OTHER INFORMATION: residues 182-205 of alpha-PAK

<400> SEQUENCE: 5

Asp Ala Thr Pro Pro Pro Val Ile Ala Pro Arg Pro Glu His Thr Lys
1               5                   10                  15

Ser Val Tyr Thr Arg Ser Val Ile
            20

<210> SEQ ID NO 6
<211> LENGTH: 705
<212> TYPE: DNA
<213> ORGANISM: Escherichia coli

<400> SEQUENCE: 6
atggctaaac tgaccaagcg catgcgtgtt atccgcgaga agttgatgc aaccaaacag      60 tacgacatca cgaagctat cgcactgctg aaagagctgg cgactgctaa attcgtagaa     120
agcgtggacg tagctgttaa cctcggcatc gacgctcgta atctgacca gaacgtacgt     180 ggtgcaactg tactgccgca cggtactggc cgttccgttc gcgtagccgt atttacccaa    240
ggtgcaaacg ctgaagctgc taaagctgca ggcgcagaac tggtaggtat ggaagatctg    300
gctgaccaga tcaagaaagg cgaaatgaac tttgacgttg ttattgcttc tccggatgca    360
atgcgcgttg ttggccagct gggccaggtt ctgggtccgc gcggcctgat gccaaacccg    420
aaagtgggta ctgtaacacc gaacgttgct gaagcggtta aaacgctaa agctggccag    480 gttcgttacc gtaacgacaa aaacggcatc atccacacca ccatcggtaa agtggacttt    540
gacgctgaca aactgaaaga aaacctggaa gctctgctgg ttgcgctgaa aaaagcaaaa    600
```

```
ccgactcagg cgaaaggcgt gtacatcaag aaagttagca tctccaccac catgggtgca       660
ggtgttgcag ttgaccaggc tggcctgagc gcttctgtaa actaa                       705
```

<210> SEQ ID NO 7
<211> LENGTH: 234
<212> TYPE: PRT
<213> ORGANISM: Escherichia coli

<400> SEQUENCE: 7

```
Met Ala Lys Leu Thr Lys Arg Met Arg Val Ile Arg Glu Lys Val Asp
1               5                   10                  15

Ala Thr Lys Gln Tyr Asp Ile Asn Glu Ala Ile Ala Leu Leu Lys Glu
            20                  25                  30

Leu Ala Thr Ala Lys Phe Val Glu Ser Val Asp Val Ala Val Asn Leu
        35                  40                  45

Gly Ile Asp Ala Arg Lys Ser Asp Gln Asn Val Arg Gly Ala Thr Val
    50                  55                  60

Leu Pro His Gly Thr Gly Arg Ser Val Arg Val Ala Val Phe Thr Gln
65                  70                  75                  80

Gly Ala Asn Ala Glu Ala Ala Lys Ala Ala Gly Ala Glu Leu Val Gly
                85                  90                  95

Met Glu Asp Leu Ala Asp Gln Ile Lys Lys Gly Glu Met Asn Phe Asp
            100                 105                 110

Val Val Ile Ala Ser Pro Asp Ala Met Arg Val Val Gly Gln Leu Gly
        115                 120                 125

Gln Val Leu Gly Pro Arg Gly Leu Met Pro Asn Pro Lys Val Gly Thr
    130                 135                 140

Val Thr Pro Asn Val Ala Glu Ala Val Lys Asn Ala Lys Ala Gly Gln
145                 150                 155                 160

Val Arg Tyr Arg Asn Asp Lys Asn Gly Ile Ile His Thr Thr Ile Gly
                165                 170                 175

Lys Val Asp Phe Asp Ala Asp Lys Leu Lys Glu Asn Leu Glu Ala Leu
            180                 185                 190

Leu Val Ala Leu Lys Lys Ala Lys Pro Thr Gln Ala Lys Gly Val Tyr
        195                 200                 205

Ile Lys Lys Val Ser Ile Ser Thr Thr Met Gly Ala Gly Val Ala Val
    210                 215                 220

Asp Gln Ala Gly Leu Ser Ala Ser Val Asn
225                 230
```

<210> SEQ ID NO 8
<211> LENGTH: 27
<212> TYPE: DNA
<213> ORGANISM: Artificial
<220> FEATURE:
<223> OTHER INFORMATION: chemically synthesized

<400> SEQUENCE: 8

```
caccatgact gataacgcca acagcca                                            27
```

<210> SEQ ID NO 9
<211> LENGTH: 21
<212> TYPE: DNA
<213> ORGANISM: Artificial
<220> FEATURE:
<223> OTHER INFORMATION: chemically synthesized

<400> SEQUENCE: 9

```
gatctctcgt acgtagttgc t                                        21
```

<210> SEQ ID NO 10
<211> LENGTH: 21
<212> TYPE: DNA
<213> ORGANISM: Artificial
<220> FEATURE:
<223> OTHER INFORMATION: chemically synthesized

<400> SEQUENCE: 10

```
atgaacacga ttaacatcgc t                                        21
```

<210> SEQ ID NO 11
<211> LENGTH: 51
<212> TYPE: DNA
<213> ORGANISM: Artificial
<220> FEATURE:
<223> OTHER INFORMATION: chemically synthesized

<400> SEQUENCE: 11

```
ggcgataagg tccagctgat cggctttggc atgaacacga ttaacatcgc t       51
```

<210> SEQ ID NO 12
<211> LENGTH: 51
<212> TYPE: DNA
<213> ORGANISM: Artificial
<220> FEATURE:
<223> OTHER INFORMATION: chemically synthesized

<400> SEQUENCE: 12

```
ggcgagggcc tgccaggcat gtgtggcggc atgaacacga ttaacatcgc t       51
```

<210> SEQ ID NO 13
<211> LENGTH: 51
<212> TYPE: DNA
<213> ORGANISM: Artificial
<220> FEATURE:
<223> OTHER INFORMATION: chemically synthesized

<400> SEQUENCE: 13

```
ggcccagatg atactccatg ggatggcggc atgaacacga ttaacatcgc t       51
```

<210> SEQ ID NO 14
<211> LENGTH: 45
<212> TYPE: DNA
<213> ORGANISM: Artificial
<220> FEATURE:
<223> OTHER INFORMATION: chemically synthesized

<400> SEQUENCE: 14

```
ggcccaccag atactccata cgccgatggc atgaacacga ttaac              45
```

<210> SEQ ID NO 15
<211> LENGTH: 21
<212> TYPE: DNA
<213> ORGANISM: Artificial
<220> FEATURE:
<223> OTHER INFORMATION: chemically synthesized

<400> SEQUENCE: 15

```
ttacgcgaac gcgaagtccg a                                        21
```

<210> SEQ ID NO 16
<211> LENGTH: 24
<212> TYPE: PRT

<213> ORGANISM: Rattus norvegicus

<400> SEQUENCE: 16

Asp Ala Thr Pro Pro Val Ile Ala Pro Arg Pro Glu His Thr Lys
1               5                   10                  15
Ser Val Tyr Thr Arg Ser Val Ile
            20

<210> SEQ ID NO 17
<211> LENGTH: 10
<212> TYPE: PRT
<213> ORGANISM: Artificial
<220> FEATURE:
<223> OTHER INFORMATION: chemically synthesized

<400> SEQUENCE: 17

Gly Asp Lys Val Gln Leu Ile Gly Phe Gly
1               5                   10

<210> SEQ ID NO 18
<211> LENGTH: 10
<212> TYPE: PRT
<213> ORGANISM: Artificial
<220> FEATURE:
<223> OTHER INFORMATION: chemically synthesized

<400> SEQUENCE: 18

Gly Glu Gly Leu Pro Gly Met Cys Gly Gly
1               5                   10

<210> SEQ ID NO 19
<211> LENGTH: 10
<212> TYPE: PRT
<213> ORGANISM: Artificial
<220> FEATURE:
<223> OTHER INFORMATION: chemically synthesized

<400> SEQUENCE: 19

Gly Pro Asp Asp Thr Pro Trp Asp Gly Gly
1               5                   10

<210> SEQ ID NO 20
<211> LENGTH: 10
<212> TYPE: PRT
<213> ORGANISM: Artificial
<220> FEATURE:
<223> OTHER INFORMATION: chemically synthesized

<400> SEQUENCE: 20

Gly Pro Pro Asp Thr Pro Tyr Ala Asp Gly
1               5                   10

<210> SEQ ID NO 21
<211> LENGTH: 30
<212> TYPE: DNA
<213> ORGANISM: Artificial
<220> FEATURE:
<223> OTHER INFORMATION: chemically synthesized

<400> SEQUENCE: 21
ggcgataagg tccagctgat cggctttggc                                        30

<210> SEQ ID NO 22
<211> LENGTH: 30
<212> TYPE: DNA
<213> ORGANISM: Artificial

<220> FEATURE:
<223> OTHER INFORMATION: chemically synthesized

<400> SEQUENCE: 22
ggcgagggcc tgccaggcat gtgtggcggc         30

<210> SEQ ID NO 23
<211> LENGTH: 30
<212> TYPE: DNA
<213> ORGANISM: Artificial
<220> FEATURE:
<223> OTHER INFORMATION: chemically synthesized

<400> SEQUENCE: 23
ggcccagatg atactccatg ggatggcggc         30

<210> SEQ ID NO 24
<211> LENGTH: 30
<212> TYPE: DNA
<213> ORGANISM: Artificial
<220> FEATURE:
<223> OTHER INFORMATION: chemically synthesized

<400> SEQUENCE: 24
ggcccaccag atactccata cgccgatggc         30

<210> SEQ ID NO 25
<211> LENGTH: 20
<212> TYPE: DNA
<213> ORGANISM: Artificial
<220> FEATURE:
<223> OTHER INFORMATION: chemically synthesized

<400> SEQUENCE: 25
taatacgact cactataggg         20

<210> SEQ ID NO 26
<211> LENGTH: 27
<212> TYPE: PRT
<213> ORGANISM: Artificial
<220> FEATURE:
<223> OTHER INFORMATION: chemically synthesized

<400> SEQUENCE: 26

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 27
<211> LENGTH: 21
<212> TYPE: PRT
<213> ORGANISM: Artificial
<220> FEATURE:
<223> OTHER INFORMATION: chemically synthesized

<400> SEQUENCE: 27

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 28
<211> LENGTH: 18
<212> TYPE: PRT

```
<213> ORGANISM: Artificial
<220> FEATURE:
<223> OTHER INFORMATION: chemically synthesized
<220> FEATURE:
<221> NAME/KEY: MISC_FEATURE
<222> LOCATION: (1)..(18)
<223> OTHER INFORMATION: residues 615-632 of murine vascular endothelial
      cadherin

<400> SEQUENCE: 28

Leu Leu Ile Ile Leu Arg Arg Arg Ile Arg Lys Gln Ala His Ala His
1               5                   10                  15

Ser Lys

<210> SEQ ID NO 29
<211> LENGTH: 16
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (1)..(16)
<223> OTHER INFORMATION: residues 43-58 of Antennapedia homeodomain

<400> SEQUENCE: 29

Arg Gln Ile Lys Ile Trp Phe Gln Asn Arg Arg Met Lys Trp Lys Lys
1               5                   10                  15

<210> SEQ ID NO 30
<211> LENGTH: 14
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (1)..(14)
<223> OTHER INFORMATION: residues 48-60 of Tat protein

<400> SEQUENCE: 30

Gly Arg Lys Lys Arg Arg Gln Arg Arg Arg Pro Pro Gln Cys
1               5                   10

<210> SEQ ID NO 31
<211> LENGTH: 27
<212> TYPE: PRT
<213> ORGANISM: Artificial
<220> FEATURE:
<223> OTHER INFORMATION: chemically synthesized

<400> SEQUENCE: 31

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 32
<211> LENGTH: 18
<212> TYPE: PRT
<213> ORGANISM: Artificial
<220> FEATURE:
<223> OTHER INFORMATION: chemically synthesized

<400> SEQUENCE: 32

Lys Leu Ala Leu Lys Leu Ala Leu Lys Ala Leu Lys Ala Ala Leu Lys
1               5                   10                  15
```

Leu Ala

```
<210> SEQ ID NO 33
<211> LENGTH: 7
<212> TYPE: PRT
<213> ORGANISM: Artificial
<220> FEATURE:
<223> OTHER INFORMATION: chemically synthesized

<400> SEQUENCE: 33

Pro Lys Lys Lys Arg Lys Val
1               5

<210> SEQ ID NO 34
<211> LENGTH: 33
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (3)..(8)
<223> OTHER INFORMATION: residues 3 and 8 linked to BSR

<400> SEQUENCE: 34

Gln Glu Cys Trp Leu Glu Thr Cys Asp Ala Thr Pro Pro Val Ile
1               5                  10                  15

Ala Pro Arg Pro Glu His Thr Lys Ser Val Tyr Thr Arg Ser Val Ile
            20                  25                  30

Cys

<210> SEQ ID NO 35
<211> LENGTH: 37
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (7)..(12)
<223> OTHER INFORMATION: residues 7 and 12 linked to BSR

<400> SEQUENCE: 35

Gln Glu Trp Leu Glu Thr Cys Trp Leu Glu Thr Cys Asp Ala Thr Pro
1               5                  10                  15

Pro Pro Val Ile Ala Pro Arg Pro Glu His Thr Lys Ser Val Tyr Thr
            20                  25                  30

Arg Ser Val Ile Cys
        35

<210> SEQ ID NO 36
<211> LENGTH: 40
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (10)..(15)
<223> OTHER INFORMATION: residues 10 and 15 linked to BSR

<400> SEQUENCE: 36

Ala Ser Lys Val Arg His Met Gln Glu Cys Trp Leu Glu Thr Cys Asp
1               5                  10                  15

Ala Thr Pro Pro Val Ile Ala Pro Arg Pro Glu His Thr Lys Ser
            20                  25                  30
```

```
Val Tyr Thr Arg Ser Val Ile Cys
        35                  40

<210> SEQ ID NO 37
<211> LENGTH: 44
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (14)..(19)
<223> OTHER INFORMATION: residues 14 and 19 linked to BSR

<400> SEQUENCE: 37

Ala Ser Lys Val Arg His Met Gln Glu Trp Leu Glu Thr Cys Trp Leu
1               5                   10                  15

Glu Thr Cys Asp Ala Thr Pro Pro Val Ile Ala Pro Arg Pro Glu
            20                  25                  30

His Thr Lys Ser Val Tyr Thr Arg Ser Val Ile Cys
        35                  40

<210> SEQ ID NO 38
<211> LENGTH: 32
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (7)..(7)
<223> OTHER INFORMATION: linked to Cy3B

<400> SEQUENCE: 38

Gln Glu Trp Leu Glu Thr Lys Asp Ala Thr Pro Pro Val Ile Ala
1               5                   10                  15

Pro Arg Pro Glu His Thr Lys Ser Val Tyr Thr Arg Ser Val Ile Cys
            20                  25                  30

<210> SEQ ID NO 39
<211> LENGTH: 39
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (14)..(14)
<223> OTHER INFORMATION: linked to Cy3B

<400> SEQUENCE: 39

Ala Ser Lys Val Arg His Met Gln Glu Trp Leu Glu Thr Lys Asp Ala
1               5                   10                  15

Thr Pro Pro Val Ile Ala Pro Arg Pro Glu His Thr Lys Ser Val
            20                  25                  30

Tyr Thr Arg Ser Val Ile Cys
        35

<210> SEQ ID NO 40
<211> LENGTH: 32
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
```

<222> LOCATION: (8)..(8)
<223> OTHER INFORMATION: linked to TAMRA

<400> SEQUENCE: 40

Gly Gly Gly Ala Gly Gly Cys Lys Asp Ala Thr Pro Pro Val Ile
1               5                   10                  15

Ala Pro Arg Pro Glu His Thr Lys Ser Val Tyr Thr Arg Ser Val Ile
            20                  25                  30

<210> SEQ ID NO 41
<211> LENGTH: 6
<212> TYPE: PRT
<213> ORGANISM: Artificial
<220> FEATURE:
<223> OTHER INFORMATION: chemically synthesized

<400> SEQUENCE: 41

Gly Gly Gly Ala Gly Gly
1               5

<210> SEQ ID NO 42
<211> LENGTH: 26
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (2)..(2)
<223> OTHER INFORMATION: linked to TAMRA

<400> SEQUENCE: 42

Cys Lys Asp Ala Thr Pro Pro Val Ile Ala Pro Arg Pro Glu His
1               5                   10                  15

Thr Lys Ser Val Tyr Thr Arg Ser Val Ile
            20                  25

<210> SEQ ID NO 43
<211> LENGTH: 33
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (8)..(8)
<223> OTHER INFORMATION: linked to TAMRA

<400> SEQUENCE: 43

Gln Glu Trp Leu Glu Thr Cys Lys Asp Ala Thr Pro Pro Val Ile
1               5                   10                  15

Ala Pro Arg Pro Glu His Thr Lys Ser Val Tyr Thr Arg Ser Val Ile
            20                  25                  30

Cys

<210> SEQ ID NO 44
<211> LENGTH: 39
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (15)..(15)
<223> OTHER INFORMATION: linked to TAMRA

<400> SEQUENCE: 44

Gly Gly Ala Gly Gly Ala Gly Gly Ala Gly Gly Cys Lys Asp
1               5                   10                  15

Ala Thr Pro Pro Pro Val Ile Ala Pro Arg Pro Glu His Thr Lys Ser
                20                  25                  30

Val Tyr Thr Arg Ser Val Ile
            35

<210> SEQ ID NO 45
<211> LENGTH: 36
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (7)..(12)
<223> OTHER INFORMATION: residues 7 and 12 linked to BSR

<400> SEQUENCE: 45

Gly Gly Gly Ala Gly Gly Cys Gly Gly Gly Cys Asp Ala Thr Pro
1               5                   10                  15

Pro Pro Val Ile Ala Pro Arg Pro Glu His Thr Lys Ser Val Tyr Thr
                20                  25                  30

Arg Ser Val Ile
        35

<210> SEQ ID NO 46
<211> LENGTH: 43
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (14)..(19)
<223> OTHER INFORMATION: residues 14 and 19 linked to BSR

<400> SEQUENCE: 46

Gly Gly Ala Gly Gly Ala Gly Gly Ala Gly Gly Cys Gly Gly
1               5                   10                  15

Gly Gly Cys Asp Ala Thr Pro Pro Pro Val Ile Ala Pro Arg Pro Glu
                20                  25                  30

His Thr Lys Ser Val Tyr Thr Arg Ser Val Ile
            35                  40

<210> SEQ ID NO 47
<211> LENGTH: 40
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (8)..(8)
<223> OTHER INFORMATION: linked to TAMRA

<400> SEQUENCE: 47

Gly Gly Gly Ala Gly Gly Cys Lys Asp Ala Thr Pro Pro Val Ile
1               5                   10                  15

Ala Pro Arg Pro Glu His Thr Lys Ser Val Tyr Thr Arg Ser Val Ile
                20                  25                  30

Pro Lys Lys Lys Arg Lys Val Cys
        35                  40

```
<210> SEQ ID NO 48
<211> LENGTH: 47
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (15)..(15)
<223> OTHER INFORMATION: linked to TAMRA

<400> SEQUENCE: 48

Gly Gly Ala Gly Gly Gly Ala Gly Gly Gly Ala Gly Gly Cys Lys Asp
1               5                   10                  15

Ala Thr Pro Pro Pro Val Ile Ala Pro Arg Pro Glu His Thr Lys Ser
            20                  25                  30

Val Tyr Thr Arg Ser Val Ile Pro Lys Lys Lys Arg Lys Val Cys
        35                  40                  45

<210> SEQ ID NO 49
<211> LENGTH: 44
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (7)..(12)
<223> OTHER INFORMATION: residues 7 and 12 linked to BSR

<400> SEQUENCE: 49

Gly Gly Gly Ala Gly Gly Cys Gly Gly Gly Cys Asp Ala Thr Pro
1               5                   10                  15

Pro Pro Val Ile Ala Pro Arg Pro Glu His Thr Lys Ser Val Tyr Thr
            20                  25                  30

Arg Ser Val Ile Pro Lys Lys Lys Arg Lys Val Cys
        35                  40

<210> SEQ ID NO 50
<211> LENGTH: 51
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (14)..(19)
<223> OTHER INFORMATION: residues 14 and 19 linked to BSR

<400> SEQUENCE: 50

Gly Gly Ala Gly Gly Gly Ala Gly Gly Gly Ala Gly Gly Cys Gly Gly
1               5                   10                  15

Gly Gly Cys Asp Ala Thr Pro Pro Pro Val Ile Ala Pro Arg Pro Glu
            20                  25                  30

His Thr Lys Ser Val Tyr Thr Arg Ser Val Ile Pro Lys Lys Lys Arg
        35                  40                  45

Lys Val Cys
    50

<210> SEQ ID NO 51
<211> LENGTH: 8
<212> TYPE: PRT
<213> ORGANISM: Artificial
<220> FEATURE:
<223> OTHER INFORMATION: chemically synthesized
```

-continued

```
<220> FEATURE:
<221> NAME/KEY: MISC_FEATURE
<222> LOCATION: (8)..(8)
<223> OTHER INFORMATION: linked to fluorescein

<400> SEQUENCE: 51

Pro Lys Lys Lys Arg Lys Val Lys
1               5

<210> SEQ ID NO 52
<211> LENGTH: 44
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (15)..(20)
<223> OTHER INFORMATION: residues 14 and 20 are linked to BSR

<400> SEQUENCE: 52

Gly Gly Ala Gly Gly Gly Ala Gly Gly Gly Ala Gly Gly Cys Cys Gly
1               5                   10                  15

Gly Gly Gly Cys Asp Ala Thr Pro Pro Pro Val Ile Ala Pro Arg Pro
            20                  25                  30

Glu His Thr Lys Ser Val Tyr Thr Arg Ser Val Ile
        35                  40

<210> SEQ ID NO 53
<211> LENGTH: 38
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (9)..(14)
<223> OTHER INFORMATION: residues 9 and 14 linked to BSR

<400> SEQUENCE: 53

Pro Lys Lys Lys Arg Lys Val Cys Cys Gly Gly Gly Cys Asp Ala
1               5                   10                  15

Thr Pro Pro Pro Val Ile Ala Pro Arg Pro Glu His Thr Lys Ser Val
            20                  25                  30

Tyr Thr Arg Ser Val Ile
        35

<210> SEQ ID NO 54
<211> LENGTH: 44
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (15)..(20)
<223> OTHER INFORMATION: residues 15 and 20 linked to BSR

<400> SEQUENCE: 54

Pro Lys Lys Lys Arg Lys Val Gly Gly Gly Ala Gly Gly Cys Cys Gly
1               5                   10                  15

Gly Gly Gly Cys Asp Ala Thr Pro Pro Pro Val Ile Ala Pro Arg Pro
            20                  25                  30

Glu His Thr Lys Ser Val Tyr Thr Arg Ser Val Ile
        35                  40
```

```
<210> SEQ ID NO 55
<211> LENGTH: 33
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (9)..(9)
<223> OTHER INFORMATION: linked to Cy3B

<400> SEQUENCE: 55

Pro Lys Lys Lys Arg Lys Val Cys Lys Asp Ala Thr Pro Pro Val
 1               5                  10                  15

Ile Ala Pro Arg Pro Glu His Thr Lys Ser Val Tyr Thr Arg Ser Val
            20                  25                  30

Ile

<210> SEQ ID NO 56
<211> LENGTH: 39
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (15)..(15)
<223> OTHER INFORMATION: linked to Cy3B

<400> SEQUENCE: 56

Gly Gly Gly Pro Lys Lys Lys Arg Lys Val Gly Gly Gly Cys Lys Asp
 1               5                  10                  15

Ala Thr Pro Pro Pro Val Ile Ala Pro Arg Pro Glu His Thr Lys Ser
            20                  25                  30

Val Tyr Thr Arg Ser Val Ile
        35

<210> SEQ ID NO 57
<211> LENGTH: 32
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (8)..(8)
<223> OTHER INFORMATION: linked to Cy3B

<400> SEQUENCE: 57

Gly Gly Gly Ala Gly Gly Cys Lys Asp Ala Thr Pro Pro Val Ile
 1               5                  10                  15

Ala Pro Arg Pro Glu His Thr Lys Ser Val Tyr Thr Arg Ser Val Ile
            20                  25                  30

<210> SEQ ID NO 58
<211> LENGTH: 39
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (15)..(15)
<223> OTHER INFORMATION: Cy3B

<400> SEQUENCE: 58
```

```
Gly Gly Ala Gly Gly Gly Ala Gly Gly Gly Ala Gly Gly Cys Lys Asp
1               5                   10                  15

Ala Thr Pro Pro Pro Val Ile Ala Pro Arg Pro Glu His Thr Lys Ser
            20                  25                  30

Val Tyr Thr Arg Ser Val Ile
        35

<210> SEQ ID NO 59
<211> LENGTH: 33
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (9)..(9)
<223> OTHER INFORMATION: linked to TAMRA

<400> SEQUENCE: 59

Pro Lys Lys Lys Arg Lys Val Cys Lys Asp Ala Thr Pro Pro Pro Val
1               5                   10                  15

Ile Ala Pro Arg Pro Glu His Thr Lys Ser Val Tyr Thr Arg Ser Val
            20                  25                  30

Ile

<210> SEQ ID NO 60
<211> LENGTH: 39
<212> TYPE: PRT
<213> ORGANISM: Artificial
<220> FEATURE:
<223> OTHER INFORMATION: chemically synthesized
<220> FEATURE:
<221> NAME/KEY: MISC_FEATURE
<222> LOCATION: (15)..(15)
<223> OTHER INFORMATION: linked to TAMRA

<400> SEQUENCE: 60

Gly Gly Gly Pro Lys Lys Lys Arg Lys Val Gly Gly Gly Cys Lys Asp
1               5                   10                  15

Ala Thr Pro Pro Pro Val Ile Ala Pro Arg Pro Glu His Thr Lys Ser
            20                  25                  30

Val Tyr Thr Arg Ser Val Ile
        35
```

METHODS OF DETECTING TRANSCRIPTION

This is a National Stage application of PCT International Application No. PCT/US2006/19107, filed May 17, 2006, which in turn claims the benefit pursuant to 35 U.S.C. §119(e) of U.S. Provisional Application No. 60/682,334, filed on May 18, 2005, which is hereby incorporated by reference in its entirety herein.

BACKGROUND OF THE INVENTION

An increasing number of genomes from diverse and important organisms, including humans and pathogenic microbes, have been or are now being sequenced. As the nucleic acid sequence of each new genome sequence is resolved, the need for methods to determine the expression profiles and function of each gene becomes ever more pressing.

Transcriptional machinery is largely conserved between different species ranging from yeast to human, and reflects the fundamental nature of the transcriptional process. In fact, there is good sequence conservation of over 100 proteins known to be involved in the transcriptional process. The protein that synthesizes mRNA is known as RNA polymerase II. RNA polymerase II is a large protein complex composed of multiple subunits. This protein binds to a DNA sequence, which is known as the TATA box because of the linear arrangement of the DNA sequence and its proximity to the start of transcription. However, RNA polymerase II does not bind to the TATA box without the prior association of several other proteins, including transcription factors TFIID, TFIIA and others, with this DNA region. These proteins interact with one another, forming a complex to which RNA polymerase II can bind. This scaffolding of protein interactions at the TATA box forms the transcriptional apparatus. This basic transcriptional complex is very similar for all genes in all cells of an organism, yet it is clear that transcription of selective genes can be on or off, as well as differentially regulated, in distinct cell types to yield different amounts of mRNA. This process of transcriptional regulation is multifaceted and involves the association of several additional proteins in particular arrangements with the transcriptional complex. The arrangement and identity of transcriptional accessory proteins, also called transcription factors, can be unique for individual genes.

Two methods are predominantly used to determine the function of a gene. The sequence approach identifies sequence motifs encoding structural elements, such as nucleic acid-binding domains, that can be used to postulate the function of a gene having these motifs. The drawback to this method is that without prior knowledge of the function of a motif, the sequence approach is not useful. Thus, if a new gene is discovered, but contains no known motifs, the sequence approach fails to provide any clues as to the function of that gene.

The second method explores the pattern of expression of a particular gene. The pattern of expression can illuminate the function of the gene when the expression of that gene is compared to the stimuli that affected the expression. Accumulated expression data can then provide insight as to the function of the gene and the polypeptide it encodes.

A number of methods have been devised for detecting and quantifying gene expression levels, such as northern blots (Alwine et al., 1977, Proc. Nat'l Acad. Sci. USA 74: 5350-5354), differential display (Liang and Pardee, 1992, Science 257: 967-971), S1 nuclease protection (Berk and Sharp, 1977, Cell 12: 721-732), sequencing cDNA libraries (Adams, et al., 1991, Science 252: 1651-1656; Okubo, et al., 1992, Nature Genet. 2: 173-179), serial analysis of gene expression (SAGE) (Velculescu et al., 1995, Science 270: 484-487), cDNA arrays and oligonucleotide arrays (Schena, et al., 1995, Science 270: 467-470; Schena, et al., 1996, Proc. Natl. Acad. Sci. USA 93: 10614-10619; Lockhart, et al., 1996, Nature Biotechnol. 14: 1675-1680). The common theme between these various methods of analyzing gene expression is the highly sensitive and highly specific interaction of complementary nucleic acids. Most gene expression applications employ a single, labeled oligonucleotide and a mixture of cell or tissue derived RNA species. The exquisite selectivity of the nucleic acid hybridization between the labeled probe and the unknown target RNAs provides information regarding the abundance of a particular RNA in each pool of targets. From this, gene expression data can be obtained.

cDNA microarrays represent a significant improvement over these methods because microarrays allow for the specific nucleotide-nucleotide interaction to occur on a massive scale in that many gene specific polynucleotides derived from RNA transcripts are fixed on a support and are then exposed to an even larger number of fluorescent- or radio-labeled cDNAs derived from total RNA pools of a test cell or tissue. The signal generated by hybridization between the fixed probes and the labeled targets allows determination of the relative amount of a transcript present on the microarray and in the cDNA pool, and the result of the effect of a stimulus on a cell or tissue is determined by a comparison between a test cell or tissue and a control cell or tissue.

Methods for analyzing gene expression, and microarrays in particular, have proven to be a powerful tool in the analysis of gene function. The variance in gene expression between two divergent tissues derived from the same primordial cell, the effect of a toxic chemical on a cell or tissue, the difference in gene expression between a healthy tissue and one afflicted by disease, the molecular basis of tumorigenicity, the metabolic shift from anaerobic to aerobic respiration in yeast and the basis of virulence between a non-pathogenic and pathogenic strain of the same species have all been investigated using gene expression analysis and microarrays in particular. However, current methods of gene expression analysis all require lysis of the cell or tissue, isolation of RNA, and in vitro detection of transcription and translation events. Biological phenomena are not accurately represented in the sterile atmosphere of a glass microarray chip, but rather in the intracellular milieu that influences gene expression and protein translation. Further, the gene expression analysis methods currently used require that detection of transcription and translation events take place over a series of time points that may not accurately reflect the actual workings of a biological system, rather than in real-time. Thus, microarrays offer only an approximation of actual gene expression because they require in vitro detection spaced out over an arbitrary timeframe unlikely to correspond to actual biological events.

There exists a long felt need to provide in vivo real-time detection and analysis of gene expression and function. The present invention meets this need.

BRIEF SUMMARY OF THE INVENTION

In one aspect, the present invention includes a method of detecting transcription of a DNA molecule, the method comprising contacting a cell with a detector molecule and a chimeric RNA polymerase molecule comprising a detector binding domain that specifically binds the detector molecule; wherein the detector molecule comprises: a chimeric RNA polymerase binding domain (CRPBD) capable of binding to the detector binding domain, a peptide nucleic acid (PNA) complementary to a portion of the RNA molecule; and a signaling moiety, further wherein when the RNA polymerase transcribes the DNA to produce a nascent RNA molecule, the PNA binds to the nascent RNA molecule and a signal is emitted by the detector molecule, thereby detecting transcription of the DNA molecule.

In one aspect, the detector molecule further comprises a cell penetrating peptide.

In another aspect, the detector binding domain is selected from the group consisting of an SH3 domain and a leucine zipper.

In still another aspect, the CRPBD is selected from the group consisting of an α-PAK domain and a leucine zipper.

In one aspect, the cell penetrating peptide is selected from the group consisting of a transportan peptide (TP), a TP10 peptide, a pVEC peptide, a penetratin peptide, a tat fragment peptide, a signal sequence based peptide, and an amphiphilic model peptide.

In another aspect, the signaling moiety comprises a fluorescent molecule.

In yet another aspect, the fluorescent molecule is selected from the group consisting of ReAsH, bis-((N-iodoacetyl)piperazinyl)sulfonerhodamine (BSR), Cy3B, Cy5, tetramethylrhodamine (TAMRA) and fluorescein.

In one aspect, the PNA is complementary to a di-nucleotide or a tri-nucleotide of the nascent RNA molecule.

In another aspect, the PNA is complementary to a tri-nucleotide of the nascent RNA molecule.

In still another aspect, the tri-nucleotide has the nucleic acid sequence CAC.

In one aspect, the chimeric RNA polymerase is a chimeric RNA polymerase II.

In another aspect, the chimeric RNA polymerase is a chimeric T7 RNA polymerase.

In yet another aspect, the signal is a fluorescent resonance energy transfer (FRET) signal or a polarity change signal.

In another aspect, the nascent RNA molecule is in a cell.

In one aspect, the cell is an eukaryotic cell.

In yet another aspect, the cell is in an animal.

In another aspect, the animal is a mammal.

In yet another aspect, the cell is a biological sample.

In one aspect, the present invention includes an isolated nucleopeptide conjugate complex comprising;

a) a chimeric RNA polymerase comprising a detector binding domain; and b) a detector molecule comprising a signaling moiety, a PNA complementary to a portion of an RNA molecule, and a CRPBD capable of binding to a detector binding domain, wherein the CRPBD is specifically bound to the detector binding domain of the chimeric RNA polymerase.

In one aspect, the detector binding domain is selected from the group consisting of an SH3 domain and a leucine zipper.

In still another aspect, the CRPBD is selected from the group consisting of an α-PAK domain and a leucine zipper.

In yet another aspect, the signaling moiety comprises a fluorescent molecule.

In another aspect, the fluorescent molecule is selected from the group consisting of ReAsH, bis-((N-iodoacetyl)piperazinyl)sulfonerhodamine (BSR), Cy3B, Cy5, TAMRA and fluorescein.

In one aspect, the PNA is complementary to a di-nucleotide or a tri-nucleotide of an RNA molecule.

In still another aspect, the PNA is complementary to a tri-nucleotide of an RNA molecule.

In yet another aspect, the tri-nucleotide has the nucleic acid sequence of CAC.

In one aspect, the complex further comprises a cell penetrating peptide.

In another aspect, the cell penetrating peptide is selected from the group consisting of a transportan peptide (TP), a TP10 peptide, a pVEC peptide, a penetratin peptide, a tat fragment peptide, a signal sequence based peptide, and an amphiphilic model peptide.

In yet another aspect, the RNA polymerase is an RNA polymerase II.

In one aspect, the RNA polymerase is a T7 RNA polymerase.

In one aspect, the present invention includes an isolated nucleic acid encoding a chimeric RNA polymerase, wherein the chimeric RNA polymerase comprises an RNA polymerase and a detector binding domain.

In one aspect, the present invention includes an isolated nucleic acid encoding a chimeric RNA polymerase, wherein the isolated nucleic acid comprises SEQ ID NO:1 and SEQ ID NO:2, wherein SEQ ID NO:1 is separated from SEQ ID NO:2 by a isolated nucleic acid having the sequence set forth in the group selected from SEQ ID NO:21, SEQ ID NO:22, SEQ ID NO:23, and SEQ ID NO:24.

In still another aspect, the isolated nucleic acid comprises the nucleic acid sequence set forth in SEQ ID NO:1 and SEQ ID NO:2, wherein SEQ ID NO:1 is covalently linked to SEQ ID NO:2.

In one aspect, the nucleic acid further comprising a nucleic acid encoding a tag polypeptide covalently linked thereto.

In one aspect, the present invention includes an isolated nucleic acid encoding a chimeric RNA polymerase, wherein the amino acid sequence of the chimeric RNA polymerase comprises the amino acid sequence set forth in SEQ ID NO:3 and SEQ ID NO:4, wherein SEQ ID NO:3 is separated from SEQ ID NO:4 by a peptide having from 0 to 4 prolines.

In another aspect, the tag polypeptide is selected from the group consisting of a myc tag polypeptide, a glutathione-S-transferease tag polypeptide, a green fluorescent protein tag polypeptide, a myc-pyruvate kinase tag polypeptide, a $His_6$ tag polypeptide, an influenza virus hemagglutinin tag polypeptide, a flag tag polypeptide, and a maltose binding protein tag polypeptide.

In one aspect, the nucleic acid further comprising a nucleic acid specifying a promoter/regulatory sequence operably linked thereto.

In one aspect, the present invention includes a vector comprising an isolated nucleic acid encoding a chimeric RNA polymerase.

In still another aspect, the vector further comprising a nucleic acid specifying a promoter/regulatory sequence operably linked thereto.

In one aspect, the present invention includes a recombinant cell comprising an isolated nucleic acid of the invention encoding a chimeric RNA polymerase.

In one aspect, the present invention includes a recombinant cell comprising a vector of the invention comprising an isolated nucleic acid encoding a chimeric RNA polymerase.

In one aspect, the cell is a eukaryotic cell or a prokaryotic cell.

In another aspect, the RNA polymerase is an RNA polymerase II.

In still another aspect, the RNA polymerase is a T7 RNA polymerase.

In one aspect, the present invention includes an isolated polypeptide comprising a chimeric RNA polymerase.

In one aspect, the present invention includes an isolated polypeptide comprising a chimeric RNA polymerase, wherein the chimeric RNA polymerase comprises the amino acid sequence set forth in SEQ ID NO:3 and SEQ ID NO:4, further wherein SEQ ID NO:3 is separated from SEQ ID NO:4 by a polypeptide having from 0 to 4 prolines. In one aspect, the present invention includes an antibody that specifically binds the isolated polypeptide comprising a chimeric RNA polymerase.

In one aspect, the present invention includes an isolated detector molecule comprising a CRPBD, a PNA and a signaling moiety.

In one aspect, the CRPBD is capable of binding to a detector binding domain.

In yet another aspect, the CRPBD has 75% identity the amino acid sequence set forth in SEQ ID NO:5.

In yet another aspect, the PNA is complementary to a di-nucleotide or a tri-nucleotide.

In one aspect, the PNA is complementary to a tri-nucleotide.

In another aspect, the tri-nucleotide has the nucleic acid sequence CAC.

In still another aspect, the signaling moiety comprises a fluorescent molecule.

In one aspect, the fluorescent molecule is selected from the group consisting of ReAsH, bis-((N-iodoacetyl)piperazinyl)sulfonerhodamine (BSR), Cy3B, Cy5, TAMRA and fluorescein.

In yet another aspect, the detector molecule further comprises a cell penetrating peptide.

In one aspect, the cell penetrating peptide is selected from the group consisting of a transportan peptide (TP), a TP10 peptide, a pVEC peptide, a penetratin peptide, a tat fragment peptide, a signal sequence based peptide, and an amphiphilic model peptide.

In one aspect, the present invention includes an antibody that specifically binds a detector molecule of the invention.

In one aspect, the present invention includes a kit for detecting the transcription of an RNA molecule, the kit comprising a chimeric RNA polymerase, a detector molecule, and an instruction manual for the use thereof.

In one aspect, the detector molecule in the kit further comprises a cell penetrating peptide. In one aspect, the cell penetrating peptide is selected from the group consisting of a transportan peptide (TP), a TP10 peptide, a pVEC peptide, a penetratin peptide, a tat fragment peptide, a signal sequence based peptide, a transportan peptide, and an amphiphilic model peptide.

In still another aspect, the chimeric RNA polymerase in the kit comprises a detector binding domain selected from the group consisting of an SH3 domain and a leucine zipper.

In another aspect, the detector molecule in the kit comprises a CRPBD capable of binding to a detector binding domain selected from the group consisting of an α-PAK domain and a leucine zipper.

In another aspect, the detector molecule in the kit comprises a signaling moiety. In yet another aspect, the signaling moiety comprises a fluorescent molecule. In yet another aspect, the fluorescent molecule is selected from the group consisting of ReAsH, bis-((N-iodoacetyl)piperazinyl)sulfonerhodamine (BSR), Cy3B, Cy5, TAMRA and fluorescein.

In one aspect, the detector molecule in the kit comprises a PNA complementary to a portion of an RNA molecule. In another aspect, the PNA is complementary to a di-nucleotide or a tri-nucleotide of an RNA molecule. In one aspect, the PNA is complementary to a tri-nucleotide. In still another aspect, the tri-nucleotide has the nucleic acid sequence CAC.

In yet another aspect, the chimeric RNA polymerase in the kit is an RNA polymerase II. In one aspect, the chimeric RNA polymerase is a T7 RNA polymerase.

In one aspect, the present invention includes a kit for detecting the transcription of an RNA molecule, the kit comprising an isolated nucleic acid encoding a chimeric RNA polymerase, a detector molecule, and an instruction manual for the use thereof.

In another aspect, the detector molecule of the kit further comprises a cell penetrating peptide. In another aspect, the cell penetrating peptide is selected from the group consisting of a transportan peptide (TP), a TP10 peptide, a pVEC peptide, a penetratin peptide, a tat fragment peptide, a signal sequence based peptide, and an amphiphilic model peptide.

In still another aspect, the isolated nucleic acid of the kit comprises the nucleic acid sequence set forth in SEQ ID NO:1.

In one aspect, the detector molecule of the kit comprises a CRPBD capable of binding to a detector binding domain selected from the group consisting of an α-PAK domain and a leucine zipper.

In one aspect, the detector molecule of the kit comprises a signaling moiety. In yet another aspect, the signaling moiety comprises a fluorescent molecule. In another aspect, the fluorescent molecule is selected from the group consisting of ReAsH, bis-((N-iodoacetyl)piperazinyl)sulfonerhodamine (BSR), Cy3B, Cy5, TAMRA and fluorescein.

In one aspect, the detector molecule of the kit comprises a PNA complementary to a portion of an RNA molecule. In yet another aspect, the PNA is complementary to a di-nucleotide or a tri-nucleotide of an RNA molecule. In still another aspect, the PNA is complementary to a tri-nucleotide. In yet another aspect, the tri-nucleotide has the nucleic acid sequence CAC.

In another aspect, the chimeric RNA polymerase of the kit is an RNA polymerase II. In one aspect, the chimeric RNA polymerase is a T7 RNA polymerase.

In one aspect, the present invention includes a method of sequencing an isolated DNA molecule, the method comprising ligating an isolated DNA molecule to a promoter/regulatory sequence to form a ligated DNA molecule, contacting the isolated nucleic acid with a chimeric RNA polymerase bound to a detector molecule, wherein the chimeric RNA polymerase comprises a detector binding domain and the detector molecule comprises a CRPBD capable of binding to the detector binding domain, a PNA complementary to a portion of the isolated nucleic acid, and a signaling moiety, wherein when the chimeric RNA polymerase transcribes the isolated nucleic acid into an mRNA molecule, the PNA binds to the mRNA molecule so transcribed and a signal is emitted from the detector molecule, thereby sequencing a DNA molecule.

In one aspect, the isolated DNA molecule comprises a double stranded cDNA.

In another aspect, the promoter/regulatory sequence is a T7 promoter.

In still another aspect, the detector binding domain is selected from the group consisting of an SH3 domain and a leucine zipper.

In one aspect, the CRPBD is selected from the group consisting of the α-PAK domain and a leucine zipper.

In yet another aspect, the signaling moiety comprises a fluorescent molecule. In another aspect, the fluorescent molecule is selected from the group consisting of ReAsH, bis-((N-iodoacetyl)piperazinyl)sulfonerhodamine (BSR), Cy3B, Cy5, TAMRA, and fluorescein.

In yet another aspect, the PNA is complementary to a di-nucleotide or a tri-nucleotide portion of the ligated DNA molecule. In still another aspect, the PNA is complementary to a tri-nucleotide portion of the ligated DNA molecule.

In one aspect, the RNA polymerase is an RNA polymerase II. In still another aspect, the RNA polymerase is a T7 RNA polymerase.

In another aspect, the signal is fluorescent resonance energy transfer (FRET) signal or a polarity change signal.

In yet another aspect, the tri-nucleotide has the nucleic acid sequence GTG.

In still another aspect, the promoter/regulatory sequence is attached to a substrate.

In one aspect, the method is repeated at least once and wherein the detector molecule in each repetition comprises a different PNA that is complementary to a different portion of the ligated DNA molecule.

In one aspect, the present invention includes a method of detecting translation of an RNA molecule, the method comprising contacting a cell with a detector molecule and a chimeric ribosome molecule having a chimeric ribosomal subunit comprising a detector binding domain that specifically binds the detector molecule, wherein the detector molecule comprises: a chimeric ribosome binding domain (CRBD) capable of binding to the detector binding domain, a PNA complementary to a portion of the RNA molecule; and a signaling moiety, wherein when the ribosome translates the RNA, the PNA binds to the RNA exiting the RNA exit pore on the chimeric ribosome and a signal is emitted from the detector molecule, thereby detecting translation of an RNA molecule.

In another aspect, the detector molecule further comprises a cell penetrating peptide. In one aspect, the cell penetrating peptide is selected from the group consisting of a transportan peptide (TP), a TP10 peptide, a pVEC peptide, a penetratin peptide, a tat fragment peptide, a signal sequence based peptide, and an amphiphilic model peptide.

In one aspect, the detector binding domain is selected from the group consisting of an SH3 domain and a leucine zipper.

In yet another aspect, the CRBD is selected from the group consisting of the α-PAK domain and a leucine zipper.

In another aspect, the signaling moiety comprises a fluorescent molecule. In still another aspect, the fluorescent molecule is selected from the group consisting of ReAsH, bis-((N-iodoacetyl)piperazinyl)sulfonerhodamine (BSR), Cy3B, Cy5, TAMRA, and fluorescein.

In one aspect, the PNA is complementary to a di-nucleotide or a tri-nucleotide portion of the RNA molecule. In another aspect, the PNA is complementary to a tri-nucleotide portion of the RNA molecule. In yet another aspect, the tri-nucleotide has the nucleic acid sequence CAC.

In still another aspect, the ribosome is a prokaryotic ribosome.

In one aspect, the ribosome is the 50s subunit of the ribosome.

In yet another aspect, the signal is a fluorescent resonance energy transfer (FRET) signal or a polarity change signal.

In another aspect, the RNA molecule is in a cell.

In still another aspect, the cell is an eukaryotic cell.

In one aspect, the cell is in an animal.

In yet another aspect, the animal is a mammal.

In another aspect, the cell is a biological sample.

In one aspect, the present invention comprises an isolated nucleic acid encoding a chimeric ribosomal subunit component, wherein the chimeric ribosomal subunit component comprises a ribosomal subunit component and a detector binding domain.

In one aspect, the present invention includes an isolated nucleic acid encoding a chimeric ribosomal subunit component, wherein the isolated nucleic acid comprises SEQ ID NO:6 and SEQ ID NO:2, wherein SEQ ID NO:6 is separated from SEQ ID NO:2 by an isolated nucleic acid having a sequence set forth in the group selected from SEQ ID NO:21, SEQ ID NO:22, SEQ ID NO:23, and SEQ ID NO:24.

In another aspect, the isolated nucleic acid comprises the nucleic acid sequence set forth in SEQ ID NO:6 and SEQ ID NO:2, wherein SEQ ID NO:6 is covalently linked to SEQ ID NO:2.

In one aspect, the nucleic acid further comprising a nucleic acid encoding a tag polypeptide covalently linked thereto.

In one aspect, the present invention includes an isolated nucleic acid encoding a chimeric ribosomal subunit component, wherein the amino acid sequence of the chimeric ribosomal subunit component comprises the amino acid sequence set forth in SEQ ID NO:7 and SEQ ID NO:4, wherein SEQ ID NO:7 is separated from SEQ ID NO:4 by a peptide having from 0 to 4 prolines.

In still another aspect, the tag polypeptide is selected from the group consisting of a myc tag polypeptide, a glutathione-S-transferease tag polypeptide, a green fluorescent protein tag polypeptide, a myc-pyruvate kinase tag polypeptide, a His$_6$ tag polypeptide, an influenza virus hemagglutinin tag polypeptide, a flag tag polypeptide, and a maltose binding protein tag polypeptide.

In another aspect, the nucleic acid further comprising a nucleic acid specifying a promoter/regulatory sequence operably linked thereto.

In one aspect, the present invention includes a vector comprising an isolated nucleic acid encoding a chimeric ribosomal subunit component.

In one aspect, the vector further comprising a nucleic acid specifying a promoter/regulatory sequence operably linked thereto. In one aspect, a recombinant cell comprises the vector.

In one aspect, the present invention includes a recombinant cell comprising an isolated nucleic acid encoding a chimeric ribosomal subunit component 1.

In yet another aspect, the cell is a eukaryotic cell or a prokaryotic cell.

In one aspect, the ribosomal subunit component is a prokaryotic ribosomal subunit.

In another aspect, the ribosomal subunit is a component of a 50s subunit.

In one aspect, the present invention includes an isolated polypeptide comprising a chimeric ribosomal subunit component.

In one aspect, the present invention includes an isolated polypeptide comprising a chimeric ribosomal subunit component, wherein the chimeric ribosomal subunit component comprises the amino acid sequence set forth in SEQ ID NO:7 and SEQ ID NO:4, wherein SEQ ID NO:7 is separated from SEQ ID NO:4 by a polypeptide having from 0 to 4 prolines. In one aspect, the present invention includes an antibody that specifically binds the isolated polypeptide comprising a chimeric ribosomal subunit component.

In one aspect, the present invention includes a method of detecting the transcription of a nucleic acid molecule, the method comprising contacting a cell with a detector molecule and a chimeric enzyme that transcribes a nucleic acid molecule wherein the chimeric enzyme comprises a detector binding domain that specifically binds the detector molecule, wherein the detector molecule comprises; a chimeric enzyme binding domain (CEBD) capable of binding to the detector binding domain, a PNA complementary to a portion of the nucleic acid molecule; and a signaling moiety, wherein when the chimeric enzyme transcribes the nucleic acid, the PNA binds to an RNA molecule emerging from the enzyme and a signal is emitted from the detector molecule, further wherein said method further comprises a means for detecting the signal, thereby detecting transcription of a nucleic acid molecule.

In one aspect, the detector molecule further comprises a cell penetrating peptide.

In still another aspect, the detector binding domain is selected from the group consisting of an SH3 domain and a leucine zipper.

In another aspect, the CEBD is selected from the group consisting of the α-PAK domain and a leucine zipper.

In one aspect, the cell penetrating peptide is selected from the group consisting of a transportan peptide (TP), a TP10 peptide, a pVEC peptide, a penetratin peptide, a tat fragment peptide, a signal sequence based peptide, and an amphiphilic model peptide.

In another aspect, the signaling moiety comprises a fluorescent molecule.

In yet another aspect, the fluorescent molecule is selected from the group consisting of ReAsH, bis-((N-iodoacetyl)piperazinyl)sulfonerhodamine (BSR), Cy3B, Cy5, TAMRA and fluorescein.

In one aspect, the PNA is complementary to a di-nucleotide or a tri-nucleotide portion of a nucleic acid molecule.

In another aspect, the PNA is complementary to a tri-nucleotide portion of a nucleic acid molecule.

In still another aspect, the tri-nucleotide has the nucleic acid sequence CAC.

In one aspect, the chimeric enzyme that transcribes a nucleic acid molecule is a RNA polymerase II.

In yet another aspect, the RNA polymerase is a T7 RNA polymerase.

In still another aspect, the signal is fluorescent resonance energy transfer (FRET) signal or a polarity change signal.

In another aspect, the nucleic acid molecule is in a cell.

In one aspect, the cell is an eukaryotic cell.

In yet another aspect, the cell is in an animal.

In still another aspect, the animal is a mammal.

In one aspect, the cell is a biological sample.

In one aspect, the present invention includes a method of detecting the translation of a nucleic acid molecule, the method comprising contacting a cell with detector molecule and a chimeric enzyme that translates a nucleic acid molecule wherein the chimeric enzyme comprises a detector binding domain that specifically binds the detector molecule, wherein the detector molecule comprises: a chimeric enzyme binding domain (CEBD) capable of binding to the detector binding domain, a PNA complementary to a portion of the nucleic acid molecule; and a signaling moiety, wherein when the chimeric enzyme transcribes the nucleic acid, the PNA binds to an RNA molecule emerging from the enzyme and a signal is emitted from the detector molecule, further wherein said method further comprises a means for detecting the signal, thereby detecting translation of a nucleic acid molecule.

In one aspect, the detector molecule further comprises a cell penetrating peptide. In yet another aspect, the cell penetrating peptide is selected from the group consisting of a transportan peptide (TP), a TP10 peptide, a pVEC peptide, a penetratin peptide, a tat fragment peptide, a signal sequence based peptide, and an amphiphilic model peptide.

In another aspect, the detector binding domain is selected from the group consisting of an SH3 domain and a leucine zipper.

In one aspect, the CEBD is selected from the group consisting of an α-PAK domain and a leucine zipper.

In still another aspect, the signaling moiety comprises a fluorescent molecule. In one aspect, the fluorescent molecule is selected from the group consisting of ReAsH, bis-((N-iodoacetyl)piperazinyl)sulfonerhodamine (BSR), Cy3B, Cy5, TAMRA, and fluorescein.

In another aspect, the PNA is complementary to a di-nucleotide or a tri-nucleotide portion of the RNA molecule. In one aspect, the PNA is complementary to a tri-nucleotide portion of the RNA molecule. In one aspect, the tri-nucleotide has the nucleic acid sequence CAC.

In another aspect, the chimeric enzyme is a ribosome.

In yet another aspect, the ribosome is a prokaryotic ribosome.

In one aspect, the signal is fluorescent resonance energy transfer (FRET) signal or a polarity change signal.

In yet another aspect, the nucleic acid is in a cell.

In one aspect, the cell is an eukaryotic cell.

In still another aspect, the cell is in an animal.

In one aspect, the animal is a mammal.

In another aspect, the cell is a biological sample.

In one aspect, the present invention includes a method of identifying a nucleic acid that is transcribed, the method comprising contacting a cell with a detector molecule and a chimeric enzyme that transcribes a nucleic acid molecule, wherein the chimeric enzyme comprises a detector binding domain that specifically binds a the detector molecule, wherein the detector molecule comprises: a) a chimeric enzyme binding domain (CEBD) capable of binding to a the detector binding domain, b) a PNA complementary to a portion of the nucleic acid molecule; and c) a signaling moiety, and wherein when the chimeric enzyme transcribes the nucleic acid, the PNA binds to a nascent nucleic acid molecule emerging from the enzyme and a signal is emitted by the detector molecule; detecting the signal; and identifying the nucleic acid molecule transcribed using a constrained local dynamic time warp algorithm to match the signal detected to a library of signals associated with specific sequences, thereby identifying the nucleic acid that is transcribed.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising In FIG. 1A, the underlined portions are, top to bottom, SEQ ID NOs: 45, 52, 53 and 54, respectively. The double-underlined portion is SEQ ID NO:55, which contains a nuclear localization signal (NLS). In FIG. 1B, the underlined portions are SEQ ID NOs: 34-37, top to bottom. Fluo=fluorescein. gtg=peptide nucleic acid (PNA). BSR=bis-((N-iodoacetyl)piperazinyl)sulfonerhodamine. CPP=cell penetrating peptide.

FIG. 2, comprising FIGS. 2A and 2B, is an image depicting the amino acid sequence and PNA sequence of various detector molecules. In FIG. 2A, the underlined portions are, top to bottom, SEQ ID NOs: 55, 56, 57 and 58. The double-underlined portion is SEQ ID NO:55, which contains an NLS. TP10, having a cysteine added at its N-terminal, is disulfide bonded to a cysteine in the underlined sequence. In FIG. 2B, the underlined portions are SEQ ID NOs: 38 and 39, top to bottom. Fluo=fluorescein. gtg=peptide nucleic acid (PNA). CPP=cell penetrating peptide.

FIG. 6 is an image depicting a schematic representation of a quenched signal moiety (box and oval) in a detector molecule in the absence of a nascent RNA molecule binding to a complementary PNA on the detector molecule.

FIG. 7 is an image depicting a schematic representation of a signal moiety emitting a signal in the presence of a nascent RNA molecule binding to a complementary PNA on the detector molecule.

FIG. 8 is an image depicting a schematic representation of the detection of the transcription of a DNA molecule by a chimeric RNA polymerase that specifically binds a detector molecule. A PNA bound to the detector molecule is complementary to the nascent RNA molecule and binds the nascent transcribed RNA molecule, emitting a signal from the signaling moiety that is detected, thereby detecting transcription of the DNA molecule.

FIG. 13, comprising In FIG. 13A, the underlined portions are, top to bottom, SEQ ID NOS: 59, 60, 40 and 44. The double-underlined portion is SEQ ID NO:55, which contains an NLS. TP10, having a cysteine added at its N-terminal, is disulfide bonded to a cysteine in the underlined sequence. In FIG. 13B, the underlined portions are, top to bottom, SEQ ID NOs: 47-50, respectively. The additional N-terminal cysteine added to TP10 is depicted in the detector molecules in FIG. 13B. Fluo=fluorescein. TAMRA=tetramethylrhodamine. BSR=bis-((N-iodoacetyl)piperazinyl)sulfonerhodamine. gtg=peptide nucleic acid (PNA).

FIG. 25 is an image of the nucleic acid (SEQ ID No. 2) and amino acid sequence (SEQ ID No. 4) of an SH3 domain SEQ ID NOS.

FIG. 26 is an image of the nucleic acid sequence of a T7 polymerase (SEQ ID NO:1).

FIG. 27 is an image of the amino acid sequence of a T7 polymerase (SEQ ID NO:3).

FIG. 28 is an image of the amino acid sequence of an alpha-PAK domain (SEQ ID NO:5).

FIG. 33 depicts the results of the prediction of DNA identity based upon analysis of in vitro Blinker signal. "Scan" refers to the Blinker spot that was scanned. "Peptide" is one of 3 different Blinker detector molecules used, varying by distance between fluorophores of the signal moiety. "Linking" is the type of coating on the slide for immobilization of the DNA. "Excitation" is fluorescent excitation energy. "DNA" is the identity of the DNA spotted on the microarray. "Data Call" is the ID attributed to the DNA after Blinker analysis.

DETAILED DESCRIPTION OF THE INVENTION

Figure 1A:
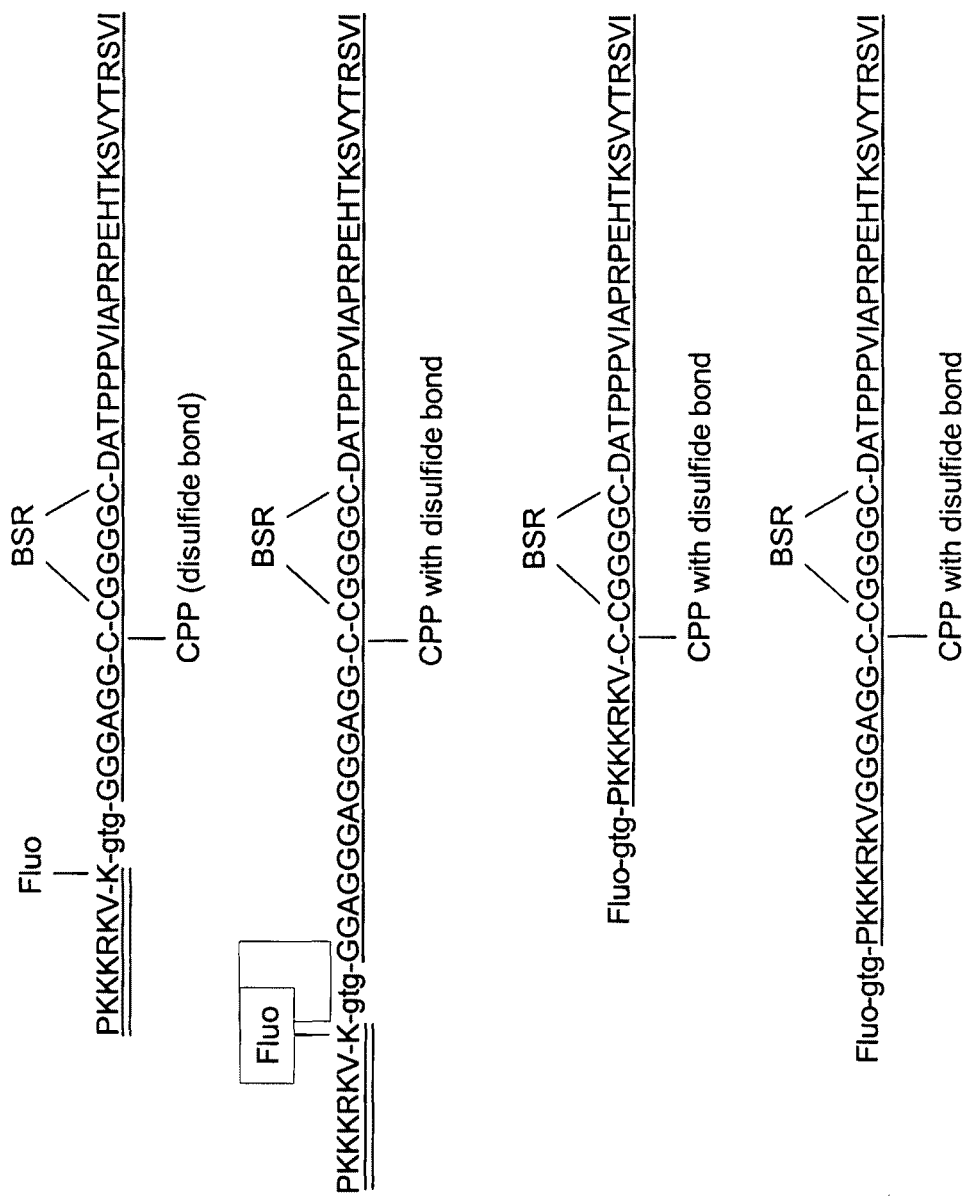
FIGS. 1A and 1B, is an image depicting the amino acid sequence and peptide nucleic acid (PNA) sequence of various detector molecules.
Figure 1B:
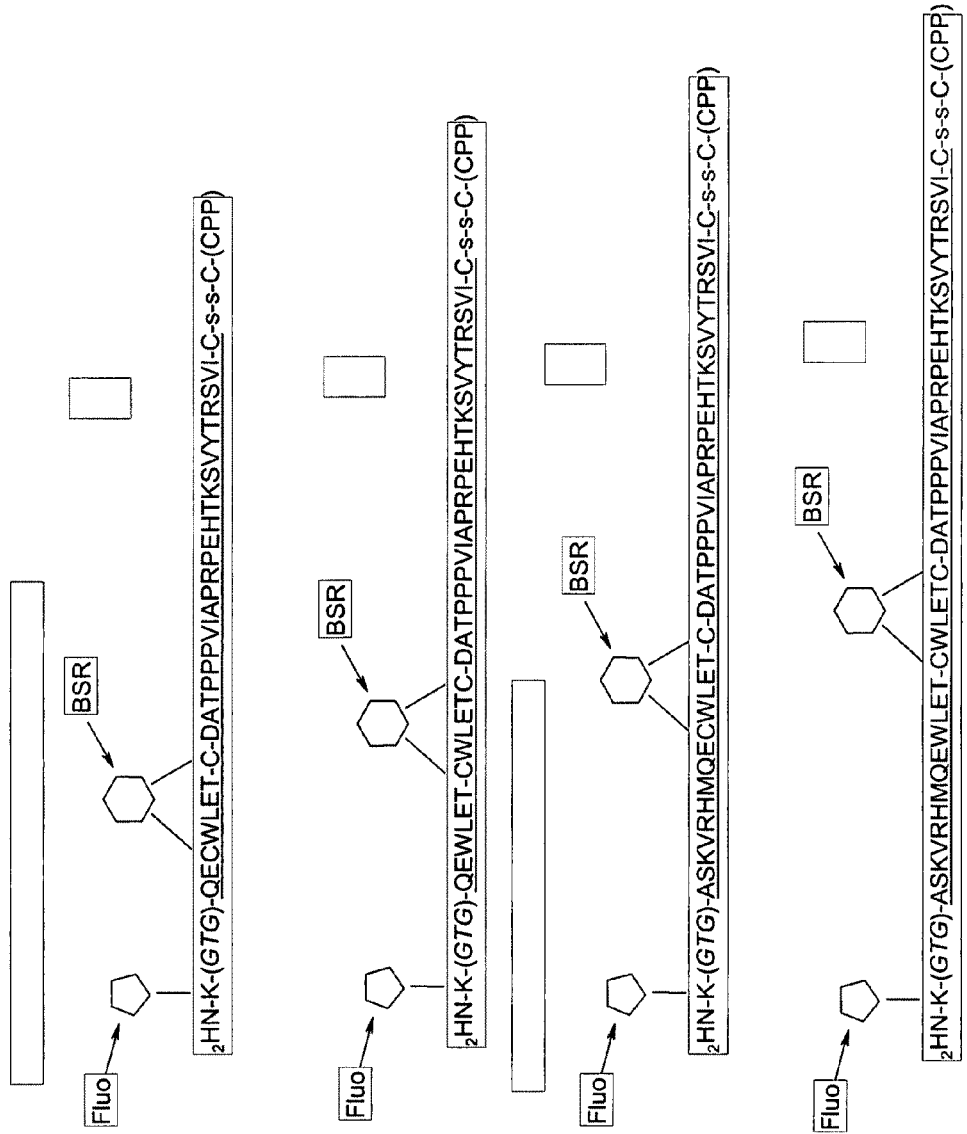
Figure 2A:
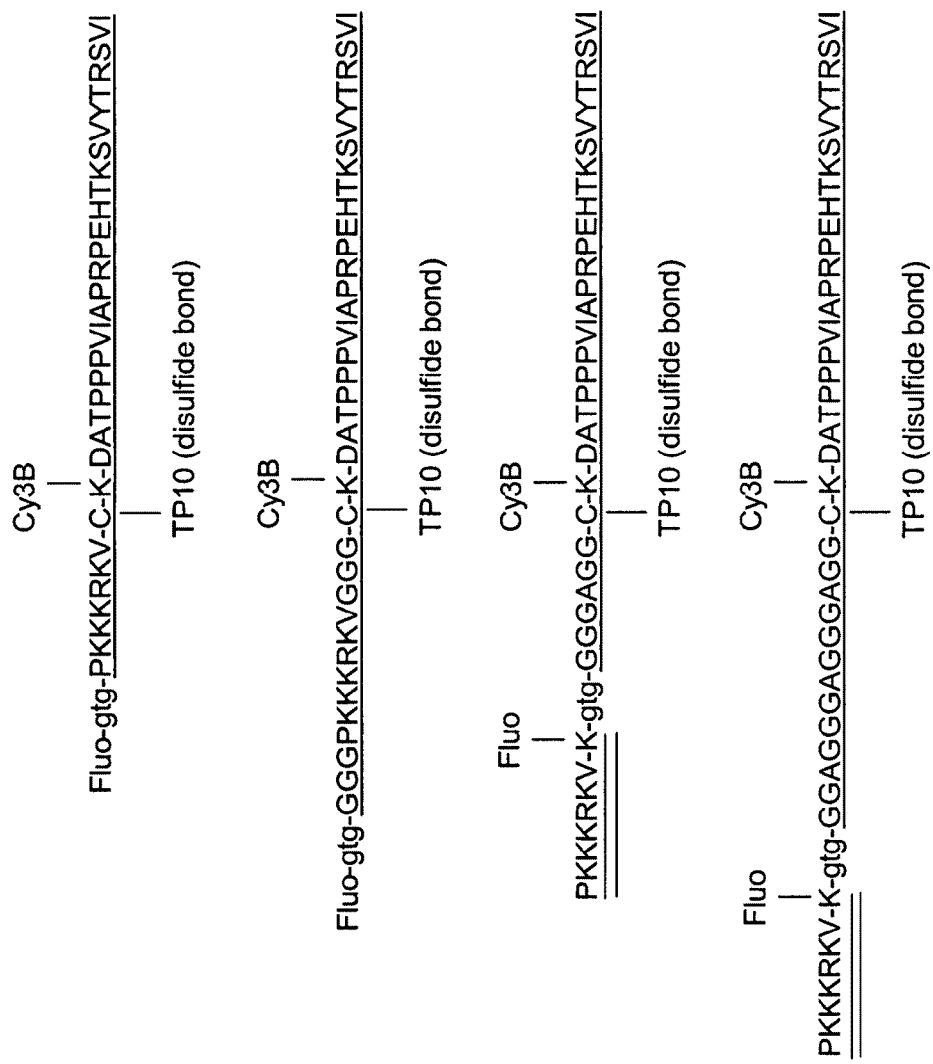
Figure 3:
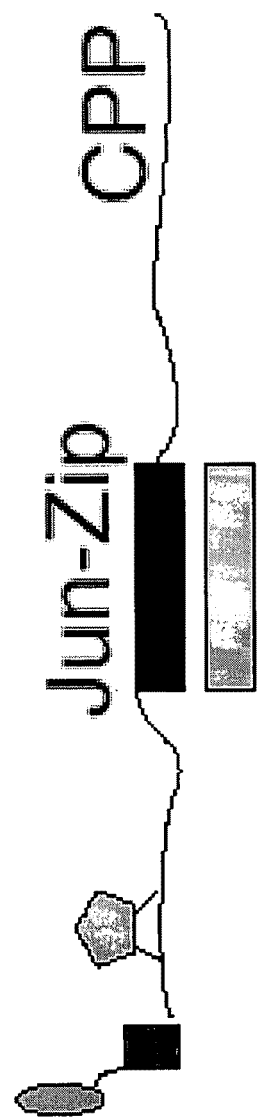
FIG. 3 is a schematic representation of a detector molecule including the signaling moiety (represented by the pentagon and the square), the chimeric RNA polymerase binding domain (CRPBD) bound to the detector binding domain, a peptide nucleic acid (PNA; oval) and a cell penetrating peptide (CPP).
Figure 4:
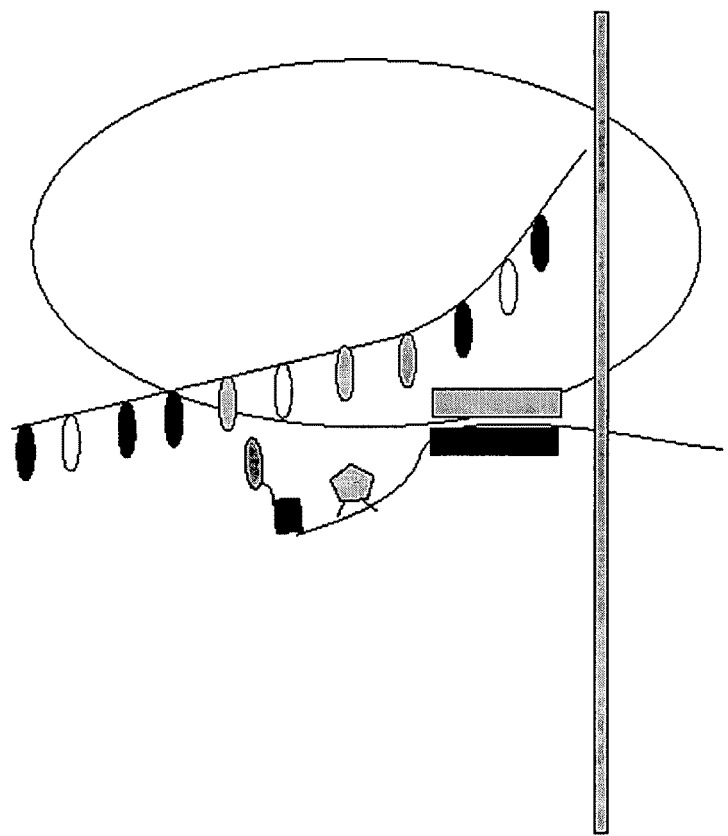
FIG. 4 is an image depicting a schematic representation of a detector molecule bound to the detector binding domain (light gray rectangle) of a chimeric RNA polymerase and detecting the transcription of a DNA molecule (thin vertical rectangle). The string of ovals represents the nascent RNA molecule produced.
Figure 5:
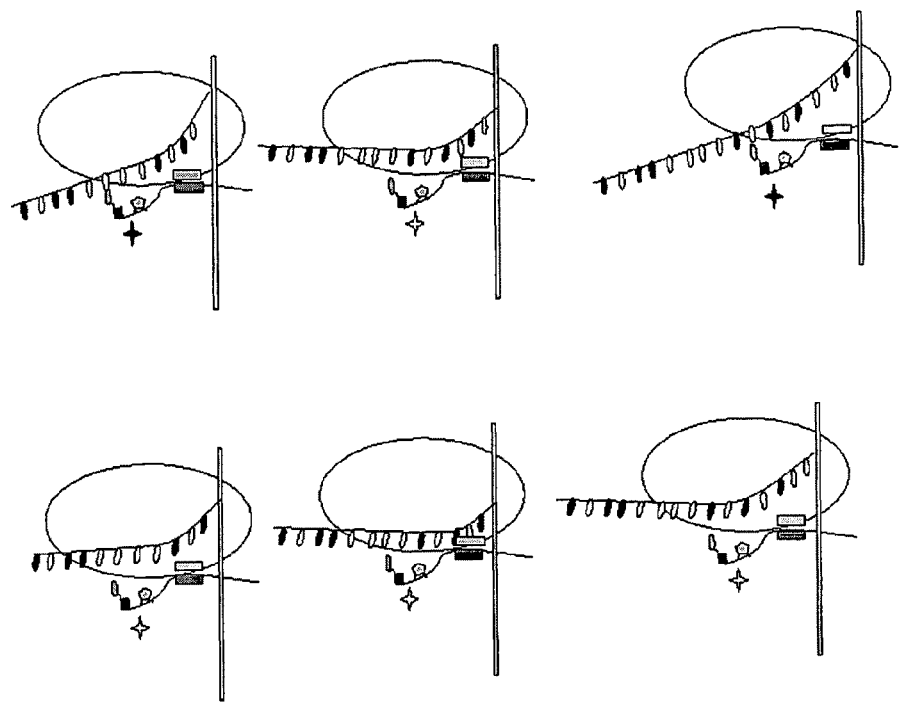
FIG. 5 is a series of images depicting a schematic representation of a nascent RNA molecule binding to a complementary PNA on the detector molecule and the detector molecule emitting a signal that detects the transcription of the DNA. The black cross indicates a blink which occurs when the PAN of the detector molecule binds to a portion of the nascent RNA molecule.
Figure 9:
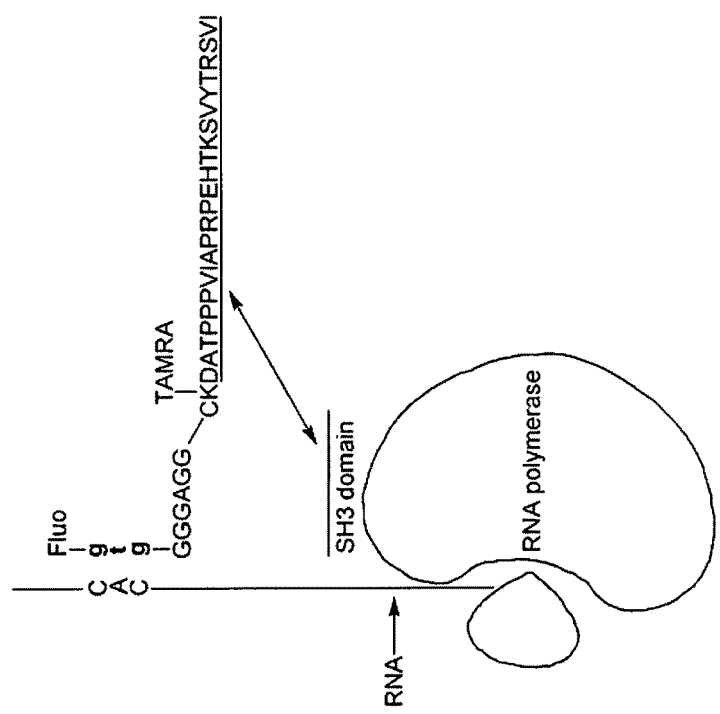
FIG. 9 is an image depicting a schematic representation of a detector molecule interacting with a chimeric RNA polymerase. The underlined amino acids are the α-PAK domain in the detector molecule which binds to the SH3 domain in the chimeric RNA polymerase. The PNA (gtg) binds the same complementary sequence as does a GTG oligonucleotide, and therefore binds to a CAC sequence in the nascent RNA. The detector molecule comprises SEQ ID NO. 40. TAMRA=tetramethylrhodamine. Fluo=fluorescein.

The ability to rapidly and accurately detect the transcription and translation of nucleic acids in vivo allows for a window into the actual workings of a cell, and thus a greater understanding of all levels of biology. In addition, the effect of therapeutic drugs, toxins, contaminants, hormones and cell-to-cell interactions, on a cell, tissue, organ or animal can be monitored at the nucleic acid level in order to elucidate the mechanism of action of a composition on its most basic level.

The present invention is based, in part, on the observation that RNA polymerase undergoes a conformational change when it binds to DNA such that the N-terminus of the protein is in close proximity to the RNA exit pore.

The present invention includes a small capture peptide (the detector binding domain) engineered in the N-terminus of RNA polymerase, thus creating a chimeric RNA polymerase. The invention further includes a synthetic detector molecule that contains multiple domains including a region (a chimeric RNA polymerase binding domain; CRPBD) that binds to the detector binding domain engineered into the RNA polymerase. Another domain in the detector molecule contains one or more moieties, preferably two, that are separated by a peptide spacer region and that comprise a signaling moiety. Another domain in the detector molecule is a peptide nucleic acid (PNA) that specifically binds a complementary nucleotide on a nascent RNA and is equivalent to at least about two, preferably three nucleotides in length. When the detector molecule is bound to the chimeric RNA polymerase as it moves along the DNA template, the PNA binds to its corresponding sequence in the emerging RNA and upon such binding, the signaling moiety is moved such that a fluorescent energy transfer signal and polarity change are produced. The detector molecule can be synthesized so that it works in vitro on microarrays or in vivo in live cells. For the latter, the detector molecule is conjugated to the transport vector, a cell-penetrating peptide (CPP).

The present invention further includes a chimeric ribosome molecule. The chimeric ribosome molecule comprises a chimeric ribosomal subunit which has a subunit component into which a detector binding domain is engineered. The chimeric ribosome molecule is useful in a method of detecting translation of an RNA molecule, using a detector molecule to produce a signal.

The present invention encompasses novel compositions, methods and kits for the detection of the transcription and translation of nucleic acid as well as for the rapid sequencing of nucleic acids.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

"Amplification" refers to any means by which a polynucleotide sequence is copied and thus expanded into a larger number of polynucleotide molecules, e.g., by reverse transcription, polymerase chain reaction, and ligase chain reaction.

The term "antibody" as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator" as the term is used herein, is meant any device or implement including, but not limited to, a hypodermic syringe, a pipette, a microcentrifuge tube, and the like, useful in the practice of any method of the invention.

"Binding" is used herein to mean specifically binds.

"Biological sample," as that term is used herein, means a sample obtained from or in a mammal that can be used to assess the level of expression of a nucleic acid, the level of a protein present, or both. Such a sample includes, but is not limited to, a cell, a blood sample, a neural tissue sample, a brain sample, and a cerebrospinal fluid sample.

A "cell penetrating peptide" is used herein to refer to a polypeptide that facilitates the entry of said polypeptide, along with any molecule associated with the polypeptide, across one or more membranes to the interior of a cell. Cell penetrating peptides as used herein include, but are not limited to, TP10, TP, pVEC, penetratin, Tat fragment, signal sequence based peptides, transportan and amphiphilic model peptide.

The terms "complementary" and "antisense", as used herein, are not entirely synonymous. "Antisense" refers particularly to the nucleic acid sequence of the non-coding strand of a double stranded DNA molecule encoding a protein, or to a sequence which is substantially homologous to the non-coding strand.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g. amino acid residues in a protein export signal sequence).

A "detector binding domain" is used herein to refer to a portion of a polypeptide that specifically binds to a portion of another polypeptide or to a non-polypeptide molecule that specifically binds another non-polypeptide molecule. A non-limiting example of a non-polypeptide specifically binding to another non-polypeptide is the binding of biotin to avidin or streptavidin.

A "detector molecule" is used herein to refer to a composition comprising a polypeptide, one or more signaling moieties, one or more peptide nucleic acids (PNA) and a portion that binds to a detector binding domain.

"Di-nucleotide" is used herein to refer to two nucleotides sharing a covalent bond.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

A first region of an oligonucleotide "flanks" a second region of the oligonucleotide if the two regions are adjacent one another or if the two regions are separated by no more than about 1000 nucleotide residues, and preferably no more than about 100 nucleotide residues.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 9 of 10 positions are matched or homologous, the two sequences share 90% homology. By way of example, the DNA sequences 3'ATTGCC5' and 3'TATGGC5' share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

An "isolated nucleic acid" refers to a nucleic acid segment or fragment which has been separated from sequences which flank it in a naturally-occurring state, e.g., a DNA fragment which has been removed from the sequences which are normally adjacent to the fragment, e.g., the sequences adjacent to the fragment in a genome in which the fragment naturally occurs. The term also applies to nucleic acids which have been substantially purified from other components, e.g., RNA or DNA or proteins, which naturally accompany the nucleic acid, in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is naturally-occurring.

A "nucleopeptide conjugate complex" is used herein to refers to a molecule comprising at least one polypeptide, at least one PNA, and a signaling moiety.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "chimeric PNA polymerase binding domain (CRPBD)" is used herein to refer to a polypeptide or molecule in a detector molecule that specifically binds to a detector binding domain.

A "chimeric ribosome binding domain (CRBD)" is used herein to refer to a polypeptide or molecule in a detector molecule that specifically binds to a detector binding domain in a ribosome.

A "chimeric enzyme binding domain (CEBD)" is used herein to refer to a polypeptide or molecule in a detector molecule that binds specifically to a detector binding domain in an enzyme.

A "portion" of a polynucleotide means at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well as a coding function.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

"Polypeptide" refers to a polymer composed of amino acid residues, related naturally-occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "chimeric RNA polymerase" is used herein to refer to an RNA polymerase molecule comprising a peptide that is not naturally-occurring in the RNA polymerase.

An "RNA polymerase molecule" or "RNA polymerase", as used herein, means an enzyme that catalyzes the synthesis of an RNA molecule on a DNA template from nucleoside triphosphate precursors.

A "signaling moiety" is used herein to refer to one or more molecules that emit a signal when stimulated or moved, the signal being detectable by a machine or human.

By the term "specifically binds," as used herein, is meant an antibody which recognizes and binds an epitope or a protein which recognizes and binds a domain, for instance, an SH3 domain or α-PAK domain, but does not substantially recognize or bind other molecules in a sample.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

A "transgene", as used herein, means an exogenous nucleic acid sequence comprising a nucleic acid which encodes a promoter/regulatory sequence operably linked to nucleic acid which encodes an amino acid sequence, which exogenous nucleic acid is encoded by an animal or cell.

"Tri-nucleotide" is used herein to refer to three nucleotides sharing two covalent bonds.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

DESCRIPTION

I. Isolated Nucleic Acids

The present invention includes an isolated nucleic acid encoding a chimeric RNA polymerase, or a fragment thereof, wherein the chimeric RNA polymerase comprises an RNA polymerase, a detector binding domain, and, optionally, a variable spacer peptide comprising from about one to about three prolines between the RNA polymerase and the detector binding domain.

The nucleic acid encoding the RNA polymerase shares at least about 50% identity with a nucleic acid having the sequence of SEQ ID NO:1. Preferably, the nucleic acid is about 60% identical, more preferably, the nucleic acid is about 65% identical to SEQ ID NO:1. Preferably, the nucleic acid is about 70% identical, more preferably, the nucleic acid is about 75% identical to SEQ ID NO:1. Preferably, the nucleic acid is about 80% identical, more preferably, the nucleic acid is about 85% identical to SEQ ID NO:1. Preferably, the nucleic acid is about 90% identical, more preferably, the nucleic acid is about 95% identical to SEQ ID NO:1. Preferably, the nucleic acid is about 97% identical, more preferably, the nucleic acid is about 98% identical to SEQ ID NO:1. Preferably, the nucleic acid is about 99% identical, more preferably, the nucleic acid is about 99.9% identical to SEQ ID NO:1. Even more preferably, the nucleic acid is identical to SEQ ID NO:1, the nucleic acid encoding a T7 RNA polymerase.

The nucleic acid encoding the detector binding domain of the chimeric RNA polymerase shares at least about 50% identity with a nucleic acid having the sequence of SEQ ID NO:2. Preferably, the nucleic acid is about 60% identical, more preferably, the nucleic acid is about 65% identical to SEQ ID NO:2. Preferably, the nucleic acid is about 70% identical, more preferably, the nucleic acid is about 75% identical to SEQ ID NO:2. Preferably, the nucleic acid is about 80% identical, more preferably, the nucleic acid is about 85% identical to SEQ ID NO:2. Preferably, the nucleic acid is about 90% identical, more preferably, the nucleic acid is about 95% identical to SEQ ID NO:2. Preferably, the nucleic acid is about 97% identical, more preferably, the nucleic acid is about 98% identical to SEQ ID NO:2. Preferably, the nucleic acid is about 99% identical, more preferably, the nucleic acid is about 99.9% identical to SEQ ID NO:2. Even more preferably, the nucleic acid is SEQ ID NO:2, the nucleic acid encoding rat beta-pix SH3 domain which binds alpha-PAK.

The chimeric RNA polymerase of the present invention can comprise an RNA polymerase fused directly to a detector binding domain. Alternatively, the chimeric RNA polymerase can comprise a variable spacer peptide between the RNA polymerase and the detector binding domain. The variable spacer peptide can comprise a polypeptide comprising one or more amino acids. Preferably, the variable spacer peptide comprising between about 1 to about 10 amino acids, preferably from about 2 to about 9 amino acids, even more preferably from about 3 to about 8 amino acids, even more preferably from about 4 to about 7 amino acids, even more preferably from about 5 to about 6 amino acids. Most preferably, the spacer peptide comprises about 1 to about 3 amino acids. Even more preferably, an amino acid in the spacer peptide is a proline. As an example, a nucleic acid encoding a chimeric RNA polymerase comprising no prolines in the spacer peptide between the detector binding domain and an RNA polymerase can comprise SEQ ID NO:21 (GGC-GATAAGGTCCAGCTGATCGGCTTT GGC). A chimeric RNA polymerase comprising one proline in the linker between the detector binding domain and an RNA polymerase can be encoded by a nucleic acid comprising SEQ ID NO:22 (GGCGAGGGCCTGCCAGGCATGTGTG-GCGGC). A nucleic acid encoding a chimeric RNA polymerase comprising two prolines in the linker between the detector binding domain and an RNA polymerase can comprise SEQ ID NO:23 (GGCCCAGATGATACTCCATGG-GATGGCGGC). A nucleic acid encoding a chimeric RNA polymerase comprising three prolines in the linker between the detector binding domain and an RNA polymerase can comprise SEQ ID NO:24 (GGCCCACCAGATACTCCAT-ACGCCGATGGC). As will be recognized by one of skill in the art, the present invention is not limited to a proline in the spacer region peptide, but rather can comprise any amino acid, including those set forth elsewhere herein. A codon encoding such an amino acid and methods of incorporating a codon into a nucleic acid sequence are well known in the art and are described elsewhere herein.

The present invention also includes an isolated nucleic acid encoding a chimeric ribosomal subunit component, or a fragment thereof, wherein the chimeric ribosomal subunit component comprises a component of a ribosomal subunit, a detector binding domain, and, optionally, a variable spacer peptide comprising from about one to about three prolines between the chimeric component of a ribosomal subunit and the detector binding domain. Preferably the ribosomal subunit is the L1 subunit. The chimeric ribosomal subunit component is part of a chimeric ribosome molecule. Preferably, the ribosome is a prokaryotic ribosome. In another embodiment, the ribosome is an eukaryotic ribosome, such as a mammalian ribosome, a yeast ribosome, a plant ribosome, and the like. In one embodiment, the ribosomal subunit component is a component of the 30s subunit (i.e. one of the about 21 proteins in the 30s subunit), in another embodiment the chimeric ribosomal subunit component is a component of the 50s subunit (i.e. one of the about 34 proteins in the 50s subunit, preferably the L1 subunit). In another embodiment, the ribosomal subunit component is a component of the 60s large subunit or a component of the 40s small subunit.

The nucleic acid encoding the ribosomal subunit component shares at least about 50% identity with a nucleic acid having the sequence of SEQ ID NO:6. Preferably, the nucleic acid is about 60% identical, more preferably, the nucleic acid is about 65% identical to SEQ ID NO:6. Preferably, the nucleic acid is about 70% identical, more preferably, the nucleic acid is about 75% identical to SEQ ID NO:6. Preferably, the nucleic acid is about 80% identical, more preferably, the nucleic acid is about 85% identical to SEQ ID NO:6. Preferably, the nucleic acid is about 90% identical, more preferably, the nucleic acid is about 95% identical to SEQ ID NO:6. Preferably, the nucleic acid is about 97% identical, more preferably, the nucleic acid is about 98% identical to SEQ ID NO:6. Preferably, the nucleic acid is about 99% identical, more preferably, the nucleic acid is about 99.9% identical to SEQ ID NO:6. Even more preferably, the nucleic acid is identical to SEQ ID NO:6, the nucleic acid encoding the L1 component of a bacterial 50s subunit.

The nucleic acid encoding the detector binding domain in the chimeric ribosomal subunit component shares at least about 50% identity with a nucleic acid having the sequence of SEQ ID NO:2. Preferably, the nucleic acid is about 60% identical, more preferably, the nucleic acid is about 65% identical to SEQ ID NO:2. Preferably, the nucleic acid is about 70% identical, more preferably, the nucleic acid is about 75% identical to SEQ ID NO:2. Preferably, the nucleic acid is about 80% identical, more preferably, the nucleic acid is about 85% identical to SEQ ID NO:2. Preferably, the nucleic acid is about 90% identical, more preferably, the nucleic acid is about 95% identical to SEQ ID NO:2. Preferably, the nucleic acid is about 97% identical, more preferably, the nucleic acid is about 98% identical to SEQ ID NO:2. Preferably, the nucleic acid is about 99% identical, more preferably, the nucleic acid is about 99.9% identical to SEQ ID NO:2. Even more preferably, the nucleic acid is SEQ ID NO:2, the nucleic acid encoding rat beta-pix SH3 domain which binds alpha-PAK.

The chimeric ribosomal subunit component of the present invention can comprise an ribosome fused directly to a detector binding domain. Alternatively, the chimeric ribosomal subunit component can comprise a spacer peptide between the ribosomal subunit component and the detector binding domain. The spacer region peptide can comprise one or more amino acids. Preferably, the spacer region peptide comprising between about 1 to about 10 amino acids, preferably from about 2 to about 9 amino acids, even more preferably from about 3 to about 8 amino acids, even more preferably from about 4 to about 7 amino acids, even more preferably from about 5 to about 6 amino acids. Most preferably, the spacer peptide comprises about 1 to about 3 amino acids.

The isolated nucleic acid of the invention should be construed to include an RNA or a DNA sequence encoding a chimeric RNA polymerase or chimeric ribosomal subunit component of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

The present invention should not be construed as being limited solely to the nucleic and amino acid sequences disclosed herein. Once armed with the present invention, it is readily apparent to one skilled in the art that other nucleic acids encoding a chimeric RNA polymerase, a chimeric ribosomal subunit component, an RNA polymerase, a detector binding domain or a spacer peptide can be obtained by following the procedures described herein in the experimental details section for the generation of other isolated nucleic acids encoding a chimeric RNA polymerase or a chimeric ribosomal subunit component as disclosed herein (e.g., site-directed mutagenesis, frame shift mutations, and the like), and procedures that are well-known in the art or to be developed. As an example, the present invention can comprise a detector binding domain comprising one helix of a leucine-zipper motif and a CRPBD comprising the other helix of the leucine-zipper motif.

Further, any other number of procedures may be used for the generation of derivative or variant forms of a chimeric RNA polymerase or a chimeric ribosomal subunit component using recombinant DNA methodology well known in the art such as, for example, that described in Sambrook et al. (2001, Molecular Cloning: A Laboratory Manual, Cold Spring Harbor Laboratory Press, New York) and Ausubel et al. (1997, Current Protocols in Molecular Biology, Green & Wiley, New York).

Procedures for the introduction of amino acid changes in a protein or polypeptide by altering the DNA sequence encoding the polypeptide are well known in the art and are also described in Sambrook et al. (2001, supra); Ausubel et al. (1997, supra). The invention also includes a nucleic acid encoding a chimeric RNA polymerase, a chimeric ribosomal subunit component, an RNA polymerase, a detector binding domain, or a spacer peptide, further comprising a nucleic acid encoding a tag polypeptide covalently linked thereto. That is, the invention encompasses a chimeric nucleic acid wherein the nucleic acid sequence encoding a tag polypeptide is covalently linked to the nucleic acid encoding a chimeric RNA polymerase or a chimeric ribosomal subunit component. Such tag polypeptides are well known in the art and include, for instance, green fluorescent protein (GFP), myc, myc-pyruvate kinase (myc-PK), $His_6$, maltose binding protein (MBP), an influenza virus hemagglutinin tag polypeptide, a flag tag polypeptide (FLAG), and a glutathione-S-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

The nucleic acid comprising a nucleic acid encoding a tag polypeptide can be used to localize a chimeric RNA polymerase or a chimeric ribosomal subunit component within a cell, a tissue, and/or a whole organism (e.g., a mammalian cell), detect a chimeric RNA polymerase or a chimeric ribosomal subunit component within the nucleus of a cell, detect a chimeric RNA polymerase or a chimeric ribosomal subunit component on a glass slide or other substrate, and/or to study the role(s) of a chimeric RNA polymerase or a chimeric ribosomal subunit component in a cell. Further, addition of a tag polypeptide facilitates isolation and purification of the "tagged" protein such that the proteins of the invention can be produced and purified readily.

II. Isolated Polypeptides

The present invention includes an isolated polypeptide comprising a chimeric RNA polymerase, or a fragment thereof, wherein the chimeric RNA polymerase comprises an RNA polymerase, a detector binding domain, and, optionally, a variable spacer peptide comprising from about one to about three prolines between the RNA polymerase polypeptide and the detector binding domain polypeptide. Preferably, the RNA polymerase polypeptide is at least about 50% identical to a polypeptide having the amino acid sequence of SEQ ID NO:3, or a fragment thereof. Preferably, the RNA polymerase polypeptide is about 55% identical, more preferably, about 60% identical, more preferably, about 65% identical to SEQ ID NO:3, or some fragment thereof. Even more preferably, the RNA polymerase polypeptide is about 70% identical, more preferably, about 75% identical, more preferably, about 80% identical to SEQ ID NO:3, or some fragment thereof. More preferably, the RNA polymerase polypeptide is about 85% identical, more preferably, about 90% identical, more preferably, about 95% identical to SEQ ID NO:3, or some fragment thereof. Even more preferably, the isolated RNA polymerase polypeptide is about 96% identical, more preferably, about 97% identical, more preferably, about 98% identical, and even more preferably about 99% identical to SEQ ID NO:3, or some fragment thereof. Most preferably, the RNA polymerase polypeptide in the chimeric RNA polymerase is SEQ ID NO:3, the amino acid sequence for the T7 RNA polymerase.

The isolated polypeptide comprising a chimeric RNA polymerase further comprises a detector binding domain. Preferably, the detector binding domain is at least about 50% identical to a polypeptide having the amino acid sequence of SEQ ID NO:4, or a fragment thereof. Preferably, the detector binding domain polypeptide is about 55% identical, more preferably, about 60% identical, more preferably, about 65% identical to SEQ ID NO:4, or some fragment thereof. Even more preferably, the detector binding domain polypeptide is about 70% identical, more preferably, about 75% identical, more preferably, about 80% identical to SEQ ID NO:4, or some fragment thereof. More preferably, the detector binding domain polypeptide is about 85% identical, more preferably, about 90% identical, more preferably, about 95% identical to SEQ ID NO:4, or some fragment thereof. Even more preferably, the detector binding domain polypeptide is about 96% identical, more preferably, about 97%/identical, more preferably, about 98% identical, and even more preferably about 99% identical to SEQ ID NO:4, or some fragment thereof. Most preferably, the portion of the isolated polypeptide comprising a detector binding domain is SEQ ID NO:4, the amino acid sequence of the SH3 domain from rat beta-PIX which binds alpha-PAK.

The chimeric RNA polymerase of the present invention can comprise an RNA polymerase fused directly to a detector binding domain, or alternatively, it can comprise a spacer peptide between the RNA polymerase polypeptide and the detector binding domain polypeptide. The spacer peptide can comprise one or more amino acids. Preferably, the spacer peptide comprises between about 1 to about 10 amino acids, preferably from about 2 to about 9 amino acids, even more preferably from about 3 to about 8 amino acids, even more preferably from about 4 to about 7 amino acids, even more preferably from about 5 to about 6 amino acids. Most preferably, the spacer peptide comprises about 1 to about 3 amino acids. Preferably, the spacer peptide comprises a proline.

The present invention also includes an isolated polypeptide comprising a chimeric ribosomal subunit component, or a fragment thereof, wherein the chimeric ribosomal subunit component comprises a ribosomal subunit component, a detector binding domain, and a variable linker region comprising from about one to about three prolines between the ribosomal subunit component and the detector binding domain. Preferably the isolated polypeptide comprising a ribosomal subunit component is derived from a prokaryotic ribosome. More preferably, the ribosomal subunit component is a component of a 50s subunit of a prokaryotic ribosome. Preferably, the ribosomal subunit component is at least about 50% identical to a polypeptide having the amino acid sequence of SEQ ID NO:7, or a fragment thereof. Preferably, the ribosomal subunit component is about 55% identical, more preferably, about 60% identical, more preferably, about 65% identical to SEQ ID NO:7, or some fragment thereof.

Even more preferably, the ribosomal subunit component is about 70% identical, more preferably, about 75% identical, more preferably, about 80% identical to SEQ ID NO:7, or some fragment thereof. More preferably, the ribosomal subunit component is about 85% identical, more preferably, about 90% identical, more preferably, about 95% identical to SEQ ID NO:7, or some fragment thereof. Even more preferably, the i ribosomal subunit component is about 96% identical, more preferably, about 97% identical, more preferably, about 98% identical, and even more preferably about 99% identical to SEQ ID NO:7, or some fragment thereof. Most preferably, the ribosomal subunit component is SEQ ID NO:7, the amino acid sequence for the L1 component of the 50s subunit of a prokaryotic ribosome.

The isolated polypeptide comprising a chimeric ribosomal subunit component further comprises a detector binding domain. Preferably, the detector binding domain is at least about 50% identical to a polypeptide having the amino acid sequence of SEQ ID NO:4, or a fragment thereof. Preferably, the detector binding domain polypeptide is about 55% identical, more preferably, about 60% identical, more preferably, about 65% identical to SEQ ID NO:4, or some fragment thereof. Even more preferably, the detector binding domain polypeptide is about 70% identical, more preferably, about 75% identical, more preferably, about 80% identical to SEQ ID NO:4, or some fragment thereof. More preferably, the detector binding domain polypeptide is about 85% identical, more preferably, about 90% identical, more preferably, about 95% identical to SEQ ID NO:4, or some fragment thereof. Even more preferably, the idetector binding domain polypeptide is about 96% identical, more preferably, about 97% identical, more preferably, about 98% identical, and even more preferably about 99% identical to SEQ ID NO:4, or some fragment thereof. Most preferably, the portion of the chimeric ribosomal subunit component polypeptide comprising a detector binding domain is SEQ ID NO:4, the amino acid sequence of the rat beta-PIX SH3 domain which binds alpha-PAK.

The chimeric ribosome of the present invention comprises a chimeric ribosomal subunit component. The chimeric ribosomal subunit component can comprise a ribosomal subunit component fused directly to a detector binding domain, or alternatively, the chimeric ribosomal subunit component can comprise a spacer peptide between the ribosome and the detector binding domain polypeptide. The spacer peptide can comprise one or more amino acids. Preferably, the spacer peptide comprises between about 1 to about 10 amino acids, preferably from about 2 to about 9 amino acids, even more preferably from about 3 to about 8 amino acids, even more preferably from about 4 to about 7 amino acids, even more preferably from about 5 to about 6 amino acids. Most preferably, the spacer peptide comprises about 1 to about 3 amino acids. Preferably, the spacer peptide comprises a proline.

The present invention includes an isolated polypeptide comprising a chimeric enzyme that transcribes a nucleic acid, or a fragment thereof, wherein the chimeric enzyme comprises an enzyme that transcribes a nucleic acid, a detector binding domain, and, optionally, a variable spacer peptide comprising from about one to about three prolines between the enzyme and the detector binding domain polypeptide. In one embodiment, the enzyme that transcribes a nucleic acid is a DNA polymerase.

III. Isolated Polypeptide Conjugates

The present invention further includes an isolated polypeptide conjugate comprising an isolated polypeptide and a non-peptide molecule. An isolated polypeptide conjugate of the present invention includes a detector molecule. In one embodiment, the detector molecule comprises a CRPBD that specifically binds to the detector binding domain of a chimeric RNA polymerase, a peptide nucleic acid (PNA) and a signaling moiety covalently or otherwise chemically bound to each other. In one embodiment, the detector molecule comprises a CRBD that specifically binds to the detector binding domain of a chimeric ribosome, a peptide nucleic acid (PNA) and a signaling moiety covalently or otherwise chemically bound to each other. In yet another embodiment, the detector molecule comprises a CEBD that specifically binds to the detector binding domain of a chimeric enzyme, a peptide nucleic acid (PNA) and a signaling moiety covalently or otherwise chemically bound to each other. In addition, the detector molecule can comprise a cell penetrating peptide, which may also be covalently or otherwise chemically bound to the remainder of the detector molecule.

The detector molecule comprises a CRPBD, a CRBD or a CEBD that specifically binds to a detector binding domain in another polypeptide, such as a chimeric RNA polymerase described elsewhere herein. Preferably, the CRPBD, the CRBD, or the CEBD is at least about 75% identical to a polypeptide having the amino acid sequence of SEQ ID NO:5, or a fragment thereof. Preferably, the CRPBD, the CRBD, or the CEBD is about 80% identical, more preferably, about 85% identical, more preferably, about 90% identical to SEQ ID NO:5, or some fragment thereof. Even more preferably, the CRPBD, the CRBD, or the CEBD is about 95% identical, more preferably, about 96% identical, more preferably, about 97% identical to SEQ ID NO:5, or some fragment thereof. More preferably, the CRPBD, the CRBD, or the CEBD of the detector molecule is about 98% identical, more preferably, about 99% identical to SEQ ID NO:5, or some fragment thereof. Most preferably, the CRPBD, the CRBD, or the CEBD of the detector molecule is SEQ ID NO:5. The skilled artisan would readily appreciate, when armed with the present disclosure and the methods disclosed herein, that the CRPBD, the CRBD, or the CEBD is not limited to SEQ ID NO:5, or fragments and homologous variants thereof, but rather includes any polypeptide wherein the polypeptide specifically binds another polypeptide that can be part of a chimeric RNA polymerase.

The detector molecule can further comprise additional peptide sequences to serve as linkers or as attachment points for a signaling moiety. The CRPBD, the CRBD, or the CEBD of the detector molecule can further comprise a peptide sequence that does not specifically bind to a detector binding domain on a chimeric RNA polymerase, but rather, serves as a point of attachment for an antibody, or a fragment thereof, that specifically binds an RNA polymerase. Thus the present invention further includes a CRPBD attached to an antibody, or a fragment thereof.

The detector molecule of the present invention further comprises a peptide nucleic acid (PNA) which binds to a nascent RNA or DNA in the method of the present invention. The PNA can be a monomer, a dimer, a trimer, or a higher polymer. Preferably, the PNA attached to the detector molecule specifically binds a di-nucleotide or a tri-nucleotide. A PNA monomer is 2-aminoethyl glycine linked by a methylenecarbonyl linkage to one of the four bases (adenine, guanine, thymine, and cytosine) found in DNA. Like amino acids, PNA monomers have amino and carboxyl termini. Unlike nucleotides, PNA monomers lack pentose sugar phosphate groups. The N-terminus of a PNA hybridizes to the 5'-end of complementary single-stranded DNA (Nielsen et al., 1991, Science 254, 1497; Eghom et al., 1992, J. Am. Chem. Soc. 114, 1895; Ilanvey et al., 1992, Science 258, 1481).

The PNA of the detector molecule can be any sequence using the common bases of A, T, C and G. Thus, a PNA can bind a di-nucleotide such as AA, AT, AC, AG, TA, TT, TC, TG, CA, CT, CC, CG, GA, GT, GC or GG. The skilled artisan, given the example above and disclosed elsewhere herein can readily produce a PNA that binds a tri-nucleotide having the sequences made from the various permutations of A, T, C, and G, and therefore such sequences need not be reproduced here. Preferably, the PNA binds a nascent RNA tri-nucleotide.

The detector molecule of the present invention further comprises two or more molecules that collectively operate as a signaling moiety. One molecule in the signaling moiety is a fluorescent molecule, such as a ReAsH molecule, a bis-((N-iodoacetyl)piperazinyl)sulfonerhodamine (BSR) molecule, a Cy3B molecule, a Cy5 molecule, or a fluorescein molecule. The second molecule is a fluorescent molecule, such as a ReAsH molecule, a bis-((N-iodoacetyl)piperazinyl)sulfonerhodamine (BSR) molecule, a Cy3B molecule, a Cy5 molecule, or a fluorescein molecule. Third and additional molecules can be a ReAsH molecule, a bis-((N-iodoacetyl) piperazinyl)sulfonerhodamine (BSR) molecule, a Cy3B molecule, a Cy5 molecule, or a fluorescein molecule. Preferably, the signaling moiety comprises two fluorescent molecules, such as a fluorescein molecule and a BSR molecule, or a fluorescein molecule and a Cy3B molecule. Thus, as demonstrated by the present disclosure, the detector molecule of the present invention can comprise any combination of molecules that are capable of generating a fluorescent or polarity signal detectable by one of the methods disclosed elsewhere herein and known in the art. In addition, the present invention can comprise the use of two or more molecules that generate a detectable fluorescent or polarity signal supplemented with additional fluorescent or polarity-generating molecules that are capable of amplifying the detectable fluorescent or polarity molecules.

The signaling moiety is covalently or otherwise chemically bound to the detector molecule such that one fluorescent molecule is bound to the CRPBD of the detector molecule or a polypeptide attached to the CRPBD of the detector molecule. A second fluorescent molecule is covalently or otherwise chemically bound to the detector molecule on an amino acid separated from the rest of the detector molecule by the PNA such that the PNA and one or more amino acids are between a first and second fluorescent molecule comprising the signaling moiety.

The detector molecule can further comprise a cell penetrating peptide covalently or otherwise chemically bound to the detector molecule. Preferably, the cell penetrating peptide is bound to the detector molecule via a disulfide bond between to cysteines. The cell penetrating peptide can be any cell penetrating peptide known in the art, including, but not limited to, a transportan peptide (TP), a TP10 peptide, a pVEC peptide, a penetratin peptide, a tat fragment peptide, a signal sequence based peptide, an amphiphilic model peptide, and the like. Sequences for cell penetrating peptides are well known in the art and are disclosed elsewhere herein. As an example, the sequences for the cell penetrating peptides TP, TP10 and pVEC are disclosed in, for example, Eiríksdóttir et al. (2004, Drug Design Reviews, 1:161-173) and in Table 1.

TABLE 1

Cell Penetrating Peptides

| Cell Penetrating Peptide | SEQ ID No. | Amino Acid Sequence |
| --- | --- | --- |
| Transportan (TP) | 26 | GWTLNSAGYLLGKINLKA LAALAKKIL |
| TP10 | 27 | AGYLLGKINLKALAALAK KIL |
| pVEC | 28 | LLIILRRRIRKQAHAHSK |
| Penetratin | 29 | RQIKIWFQNRRMKWKK |
| Tat fragment (48-60) | 30 | GRKKRRQRRRPPQC |
| Signal sequence based peptide | 31 | GALFLGWLGAAGSTMGAW SQPKKKRKV |
| Amphiphilic model peptide | 32 | KLALKLALKALKAALKLA |

The detector molecule can also comprise an intracellular accessibility domain, such as a ligand that binds a cellular receptor that is present on cells. Such intracellular accessibility domains include, but are not limited to, a folic acid attached to the detector molecule that binds the folic acid receptor on a cell, and the like.

The detector molecule and the chimeric RNA polymerase of the present invention can further comprise a nuclear localization signal (NLS). NLS are well known in the art and are described in, for example, Nair et al. (2003, Nucleic Acid Research 31:397-399). One example of an NLS, derived from the SV40 large T antigen, is PKKKRKV (SEQ ID No. 33).

The present invention further comprises a nucleopeptide conjugate complex comprising an RNA polymerase or a chimeric RNA polymerase and a detector molecule bound to the RNA polymerase or chimeric RNA polymerase. The detector molecule and a recombinant molecule are bound through the CRPBD of the detector molecule and the detector binding domain of the chimeric RNA polymerase. The CRPBD of the detector molecule specifically binds to the detector binding domain of the chimeric RNA polymerase via the specific protein-protein affinity described elsewhere herein. Such specific protein-protein binding forms a nucleopeptide conjugate complex comprising a chimeric RNA polymerase and a detector molecule which is useful in the method of the present invention disclosed elsewhere herein.

Alternatively, a detector molecule is bound to an RNA polymerase via an antibody, or fragment thereof, that is covalently attached to the detector molecule. Preferably, the antibody is bound to the detector molecule and specifically binds an RNA polymerase such that the detector molecule is bound to the RNA polymerase in a manner that is useful for the methods of the present invention.

The nucleopeptide conjugate complex of the present invention comprises the various components of a chimeric RNA polymerase and a detector molecule, including a detector binding domain, a CRPBD, a signaling moiety comprising a fluorescent molecule, a PNA, and a cell penetrating peptide. The detector molecule specifically binds to the chimeric RNA polymerase through the CRPBD of the detector molecule selectively binding the detector binding domain of the chimeric RNA polymerase.

The present invention also provides for analogs of proteins or peptides which comprise a chimeric RNA polymerase or detector molecule as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "derivatives," and "variants" of the peptides of the invention (or of the DNA encoding the same) which derivatives and variants are a chimeric RNA polymerase or a detector molecule which have been altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of a chimeric RNA polymerase or a detector molecule of the present invention. Such properties biological/biochemical properties include, but are not limited to, the binding of the CRPBD to the detector binding domain, a signaling moiety, a target interacting domain, and an intracellular targeting domain, such as an NLS.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |

| Full Name | Three-Letter Code | One-Letter Code |
|---|---|---|
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The peptides of the present invention may be readily prepared by standard, well-established solid-phase peptide synthesis (SPPS) as described by Stewart et al. (Solid Phase Peptide Synthesis, 2nd Edition, 1984, Pierce Chemical Company, Rockford, Ill.) and as described by Bodanszky and Bodanszky (The Practice of Peptide Synthesis, 1984, Springer-Verlag, New York). At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and coupling thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the t-Boc method which utilizes tert-butyloxcarbonyl as the α-amino protecting group, and the Fmoc method which utilizes 9-fluorenylmethyloxycarbonyl to protect the α-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF (hydrofluoric acid) treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. Fmoc protecting group, in combination with DVB resin derivatized with methoxyalkoxybenzyl alcohol or equivalent linker, can be used for this purpose, with cleavage from the support being effected by TFA in dichloromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC or an amino acid analyzer. Protein sequencers, which sequentially degrade the peptide and identify the amino acids in order, may also be used to determine definitely the sequence of the peptide.

Prior to its use, the peptide is purified to remove contaminants. In this regard, it will be appreciated that the peptide will be purified so as to meet the standards set out by the appropriate regulatory agencies or for specific uses. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Figure 10:
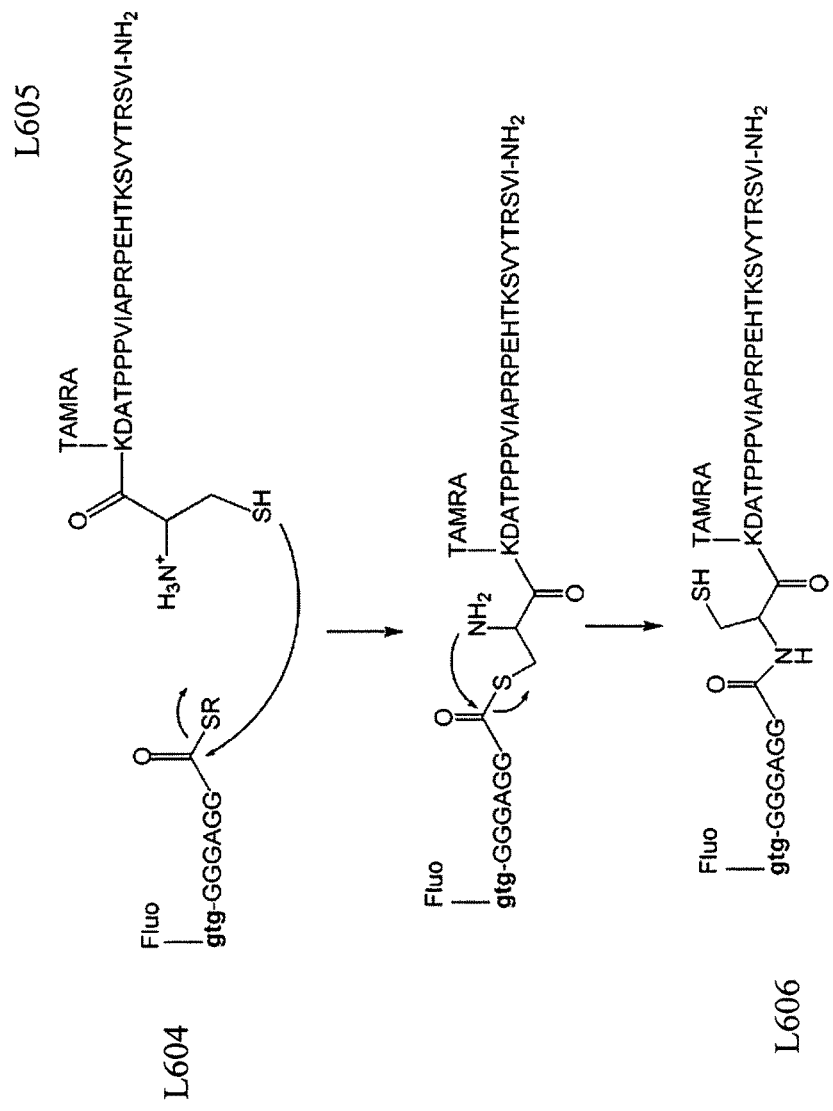
FIG. 10 is an image depicting a native chemical ligation (NCL) between peptide L604 and L605, resulting in peptide L606. Peptide L604 comprises SEQ ID No. 41, L605 comprises SEQ ID NO. 42 and L606 comprises SEQ ID No. 40. Fluo=fluorescein. TAMRA=tetramethylrhodamine.

The polypeptides and peptides of the present invention can also be prepared using, for example, native chemical ligation (NCL). NCL is a non-enzymatic coupling of unprotected peptides in aqueous solution. NCL involves a chemoselective reaction between a C-terminal thioester and a N-terminal cysteine residue to yield a native peptide bond at the site of ligation. As schematically depicted in FIG. 10, the first step is the chemoselective reaction of an unprotected synthetic peptide-thioester with another unprotected peptide segment containing a N-terminal cysteine (Cys) residue to give a thioester-linked intermediate as the initial covalent product. This intermediate undergoes spontaneous, rapid intramolecular reaction to form a native peptide bond at the ligation site. The reaction rate can also be increased when thiophenol is used as an additive.

IV. Vectors

In other related aspects, the invention includes an isolated nucleic acid encoding a chimeric RNA polymerase or a chimeric ribosomal subunit component operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Expression of a chimeric RNA polymerase or a chimeric ribosomal subunit component, either alone or fused to a detectable tag polypeptide, in a cell can be accomplished by generating a plasmid, viral, or other type of vector comprising the desired nucleic acid operably linked to a promoter/regulatory sequence which serves to drive expression of the protein, with or without tag, in cells in which the vector is introduced. Many promoter/regulatory sequences useful for driving constitutive expression of a gene are available in the art and include, but are not limited to, for example, the cytomegalovirus immediate early promoter enhancer sequence, the SV40 early promoter, as well as the Rous sarcoma virus promoter and the like. Moreover, inducible and tissue specific expression of the nucleic acid encoding a chimeric RNA polymerase or a chimeric ribosomal subunit component may be accomplished by placing the nucleic acid encoding a chimeric RNA polymerase or a chimeric ribosomal subunit component, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, hormones, and the like, are also contemplated in the invention. Thus, it will be appreciated that the invention includes the use of any promoter/regulatory sequence, which is either known or unknown, and which is capable of driving expression of the desired protein operably linked thereto.

Expressing a chimeric RNA polymerase or a chimeric ribosomal subunit component using a vector allows the isolation of large amounts of recombinantly produced protein. Further, expression of a chimeric RNA polymerase or a chimeric ribosomal subunit component driven by a promoter/regulatory sequence can allow expression of a chimeric RNA polymerase or a chimeric ribosomal subunit component in various cell and tissue types. Therefore, the invention includes not only methods of producing a chimeric RNA polymerase or a chimeric ribosomal subunit component for use in the methods of the present invention, but also includes methods of expressing a chimeric RNA polymerase or a chimeric ribosomal subunit component in any cell or tissue type known in the art, including eukaryotic cells, prokaryotic cells, tissue samples from eukaryotic organisms, and the like.

Selection of any particular plasmid vector or other DNA vector is not a limiting factor in this invention and a wide variety of vectors are well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The invention thus includes a vector comprising an isolated nucleic acid encoding a chimeric RNA polymerase or a chimeric ribosomal subunit component. The incorporation of a desired nucleic acid into a vector and the choice of vectors is well-known in the art as described in, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The invention also includes cells, viruses, proviruses, and the like, containing such vectors. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The nucleic acids encoding a chimeric RNA polymerase or a chimeric ribosomal subunit component may be cloned into various plasmid vectors. However, the present invention should not be construed to be limited to plasmids or to any particular vector. Instead, the present invention should be construed to encompass a wide plethora of vectors which are readily available and/or well-known in the art.

V. Recombinant Cells

The invention includes a recombinant cell comprising, inter alia, an isolated nucleic acid encoding a chimeric RNA polymerase or a chimeric ribosomal subunit component, a nucleic acid encoding an antibody that specifically binds an RNA polymerase, and the like. In one aspect, the recombinant cell can be transiently transfected with a plasmid encoding a portion of the nucleic acid encoding a chimeric RNA polymerase or a chimeric ribosomal subunit component. The nucleic acid need not be integrated into the cell genome nor does it need to be expressed in the cell. Moreover, the cell may be a prokaryotic or a eukaryotic cell and the invention should not be construed to be limited to any particular cell line or cell type. Such cells include, but are not limited to, neurons, stem cell, fibroblasts, astrocytes, lymphocytes, epithelial cells, plant cells, bacterial cells, and the like.

Further, it is important to note that the purpose of transgene-comprising, i.e., recombinant, cells should not be construed to be limited to the generation of an isolated chimeric RNA polymerase or a chimeric ribosomal subunit component. Rather, the invention should be construed to include any cell type into which a nucleic acid encoding a chimeric RNA polymerase or a chimeric ribosomal subunit component is introduced, including, without limitation, a prokaryotic cell and a eukaryotic cell comprising an isolated nucleic acid encoding a chimeric RNA polymerase or a chimeric ribosomal subunit component.

The invention includes a eukaryotic cell which, when the transgene of the invention is introduced therein, and the protein encoded by the desired gene is expressed therefrom, where it was not previously present or expressed in the cell or where it is now expressed at a level or under circumstances different than that before the transgene was introduced, a benefit is obtained. Such a benefit may include the fact that there has been provided a system wherein the expression of the desired gene can be used to study the in vitro expression of another gene in the cell or in a mammal in which the cell resides, a system wherein cells comprising the introduced gene can be used as research tools, and a system wherein mammal models are generated which are useful for the development of new research tools for selected biological, specifically transcription and translation of nucleic acids, in an organism or cell.

A cell expressing an isolated nucleic acid encoding a chimeric RNA polymerase or a chimeric ribosomal subunit component can be used to provide a chimeric RNA polymerase or a chimeric ribosomal subunit component to a cell, tissue, or whole animal where the expression of a chimeric RNA polymerase or a chimeric ribosomal subunit component results in the production of a chimeric RNA polymerase or a chimeric ribosomal subunit component for the detection of transcription or translation of a nucleic acid. A cell expressing an isolated nucleic acid encoding a chimeric RNA polymerase or a chimeric ribosomal subunit component can further be used to produce a chimeric RNA polymerase or a chimeric ribosomal subunit component for use in sequencing reactions and other methods described elsewhere herein. Therefore, the invention includes a cell expressing a chimeric RNA polymerase or a chimeric ribosomal subunit component for the production of a chimeric RNA polymerase or a chimeric ribosomal subunit component and for the detection of biological and biochemical phenomena, including, but not limited to, transcription and translation of nucleic acids.

One of ordinary skill would appreciate, based upon the disclosure provided herein, that a "knock-in" or "knock-out" vector of the invention comprises at least two sequences homologous to two portions of the nucleic acid which is to be replaced or deleted, respectively. The two sequences are homologous with sequences that flank the gene; that is, one sequence is homologous with a region at or near the 5' portion of the coding sequence of the nucleic acid encoding an RNA polymerase and the other sequence is further downstream from the first. One skilled in the art would appreciate, based upon the disclosure provided herein, that the present invention is not limited to any specific flanking nucleic acid sequences. Instead, the targeting vector may comprise two sequences which remove some or all of, for example, RNA polymerase (i.e., a "knock-out" vector) or which insert (i.e., a "knock-in" vector) a nucleic acid encoding a chimeric RNA polymerase or a chimeric ribosomal subunit component, or a fragment thereof, from or into a mammalian genome, respectively. The crucial feature of the targeting vector is that it comprise sufficient portions of two sequences located towards opposite, i.e., 5' and 3', ends of an RNA polymerase open reading frame (ORF) in the case of a "knock-out" vector, to allow deletion/insertion by homologous recombination to occur such that all or a portion of the nucleic acid encoding an RNA polymerase is deleted from a location on a mammalian chromosome.

The design of transgenes and knock-in and knock-out targeting vectors is well-known in the art and is described in standard treatises such as Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York), and the like. The upstream and downstream portions flanking or within the RNA polymerase coding region to be used in the targeting vector may be easily selected based upon known methods and following the teachings disclosed herein including the nucleic and amino acid sequences of RNA polymerase and chimeric RNA polymerase or a chimeric ribosomal subunit component. Armed with these sequences, one of ordinary skill in the art would be able to construct the transgenes and knock-out vectors of the invention.

Methods and compositions useful for maintaining mammalian cells in culture, primary cell culture or slice culture are well known in the art, wherein the mammalian cells are obtained from a mammal including, but not limited to, cells obtained from a mouse, a rat, a human, and other mammals, as well as non-mammalian eukaryotic organisms such as zebrafish, *C. elegans, Xenopus*, and the like.

VI. Antibodies

The present invention further includes an antibody that specifically binds an RNA polymerase, a chimeric RNA polymerase or a chimeric ribosomal subunit component of the present invention, a protein nucleic acid conjugate, or fragments thereof.

One skilled in the art would understand, based upon the disclosure provided herein, that an antibody that specifically binds an RNA polymerase, a chimeric RNA polymerase or a chimeric ribosomal subunit component, a protein nucleic acid conjugate, or fragments thereof, is useful for, inter alia, the detection of such molecules in a cell, tissue or organ. Further, an antibody that specifically binds to an RNA polymerase can be conjugated or otherwise attached to a detector molecule such that the detector molecule can specifically bind to the RNA polymerase via the conjugated antibody.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the RNA polymerase, detector molecule, a chimeric ribosomal subunit component or chimeric RNA polymerase portion is rendered immunogenic (e.g., RNA polymerase conjugated with keyhole limpet hemocyanin, KLH). The chimeric proteins are produced by cloning the appropriate nucleic acids encoding, for example, a detector molecule, a chimeric ribosomal subunit component or a chimeric RNA polymerase (e.g., SEQ ID NO:1 and SEQ ID NO:2) into a plasmid vector suitable for this purpose, such as, but not limited to, pMAL-2 or pCMX. Alternatively, antibodies to RNA polymerase II are available commercially from, for instance, Abcam, Inc. (Cambridge, Mass.).

However, the invention should not be construed as being limited solely to polyclonal antibodies that bind a chimeric RNA polymerase or a chimeric ribosomal subunit component, an RNA polymerase or a detector molecule. Rather, the invention should be construed to include other antibodies, as that term is defined elsewhere herein, to a chimeric RNA polymerase or a chimeric ribosomal subunit component, an RNA polymerase or a detector molecule, or portions thereof. Further, the present invention should be construed to encompass antibodies that, among other things, bind to a chimeric RNA polymerase or a chimeric ribosomal subunit component, an RNA polymerase or a detector molecule and are able to bind these molecule when present on Western blots, in cells, and in immunohistochemical staining of tissues thereby localizing such molecules in the tissues, and in immunofluorescence microscopy of a cell transiently or stably transfected with a nucleic acid encoding at least a portion of a chimeric RNA polymerase or a chimeric ribosomal subunit component, as well as to a cell or tissue that is contacted with a chimeric RNA polymerase or a chimeric ribosomal subunit component.

One skilled in the art would appreciate, based upon the disclosure provided herein, that the antibody can specifically bind with any portion of the protein, and the full-length protein can be used to generate antibodies specific therefor. However, the present invention is not limited to using the full-length protein as an immunogen. Rather, the present invention includes using an immunogenic portion of the protein to produce an antibody that specifically binds with a chimeric RNA polymerase or a chimeric ribosomal subunit component, an RNA polymerase or a detector molecule. That is, the invention includes immunizing an animal using an immunogenic portion, or antigenic determinant, of a chimeric RNA polymerase or a chimeric ribosomal subunit component, an RNA polymerase or a detector molecule, for example, an epitope comprising the linker region, the detector binding domain, or any other antigenic site on the molecule.

The antibodies can be produced by immunizing an animal such as, but not limited to, a rabbit or a mouse, with a chimeric RNA polymerase or a chimeric ribosomal subunit component, an RNA polymerase or a detector molecule, or a portion thereof, or by immunizing an animal using a protein comprising at least a portion of a chimeric RNA polymerase or a chimeric ribosomal subunit component, an RNA polymerase or a detector molecule, or a fusion protein including a tag polypeptide portion comprising, for example, a maltose binding protein tag polypeptide portion, covalently linked with a portion comprising the appropriate chimeric RNA polymerase or a chimeric ribosomal subunit component, RNA polymerase or detector molecule amino acid residues. The skilled artisan can also use smaller fragments of these proteins to produce antibodies that specifically bind a chimeric RNA polymerase or a chimeric ribosomal subunit component, an RNA polymerase or a detector molecule.

One skilled in the art would appreciate, based upon the disclosure provided herein, that various portions of an isolated chimeric RNA polymerase or a chimeric ribosomal subunit component, an RNA polymerase or a detector molecule can be used to generate antibodies to epitopes comprising the linker region, the detector binding domain, or any other antigenic site on the molecule or to epitopes present elsewhere on one of these molecules. Once armed with the sequence of a chimeric RNA polymerase or a chimeric ribosomal subunit component, an RNA polymerase or a detector molecule, the skilled artisan would understand, based upon the disclosure provided herein, how to obtain antibodies specific for the various portions of a chimeric RNA polymerase or a chimeric ribosomal subunit component, an RNA polymerase or a detector molecule polypeptide using methods well-known in the art or to be developed.

Therefore, the skilled artisan would appreciate, based upon the disclosure provided herein, that the present invention encompasses antibodies that specifically bind a chimeric RNA polymerase or a chimeric ribosomal subunit component, an RNA polymerase or a detector molecule.

The invention should not be construed as being limited solely to the antibodies disclosed herein or to any particular immunogenic portion of the proteins of the invention. Rather, the invention should be construed to include other antibodies, as that term is defined elsewhere herein, to a chimeric RNA polymerase or a chimeric ribosomal subunit component, an RNA polymerase or a detector molecule, or portions thereof, or to proteins sharing some homology with a chimeric RNA polymerase or a chimeric ribosomal subunit component, an RNA polymerase or a detector molecule.

One skilled in the art would appreciate, based upon the disclosure provided herein, that such antibodies can be used to localize the relevant protein in a cell and to study the role(s) of the polypeptides recognized thereby in various biochemical and biological processes. Moreover, the antibodies can be used to detect and/or measure the amount of protein present in a biological sample using well-known methods such as, but not limited to, Western blotting and enzyme-linked immunosorbent assay (ELISA). Moreover, the antibodies can be used to immunoprecipitate and/or immuno-affinity purify their cognate antigen using methods well-known in the art. In addition, the antibody can be conjugated or otherwise attached to a detector molecule so that the detector molecule specifically binds to a chimeric RNA polymerase, a chimeric ribosomal subunit component or a RNA polymerase in order to practice the methods of the present invention disclosed elsewhere herein.

The invention encompasses polyclonal, monoclonal, synthetic antibodies, and the like. One skilled in the art would understand, based upon the disclosure provided herein, that the crucial feature of the antibody of the invention is that the antibody bind specifically with a chimeric RNA polymerase or a chimeric ribosomal subunit component, an RNA polymerase or a detector molecule. That is, the antibody of the invention recognizes a chimeric RNA polymerase or a chimeric ribosomal subunit component, an RNA polymerase or a detector molecule, or a fragment thereof (e.g., an immunogenic portion or antigenic determinant thereof), on Western blots, in immunostaining of cells, and immunoprecipitates a chimeric RNA polymerase or a chimeric ribosomal subunit component, an RNA polymerase or a detector molecule using standard methods well-known in the art.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein.

Further, the antibody of the invention may be "humanized" using the technology described in, for example, Wright et al. (1992, Critical Rev. Immunol. 12:125-168), and in the references cited therein, and in Gu et al. (1997, Thrombosis and Hematocyst 77: 755-759). The present invention also includes the use of humanized antibodies specifically reactive with epitopes of a chimeric RNA polymerase, an RNA polymerase or a detector molecule. Such antibodies are capable of specifically binding a chimeric RNA polymerase, an RNA polymerase or a detector molecule, or a fragment thereof. The humanized antibodies of the invention have a human framework and have one or more complementarity determining regions (CDRs) from an antibody, typically, but not limited to a mouse antibody, specifically reactive with a chimeric RNA polymerase, an RNA polymerase or a detector molecule, or a fragment thereof.

When the antibody used in the invention is humanized, the antibody may be generated as described in Queen et al. (U.S. Pat. No. 6,180,370), Wright et al., (1992, Critical Rev. Immunol. 12:125-168) and in the references cited therein, or in Gu et al. (1997, Thrombosis and Hematocyst 77(4):755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as a chimeric RNA polymerase or a chimeric ribosomal subunit component, an RNA polymerase or a detector molecule, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

Human constant region (CDR) DNA sequences from a variety of human cells can be isolated in accordance with well known procedures. Preferably, the human constant region DNA sequences are isolated from immortalized B-cells as described in WO 87/02671, which is herein incorporated by reference. CDRs useful in producing the antibodies of the present invention may be similarly derived from DNA encoding monoclonal antibodies capable of binding to a chimeric RNA polymerase or a chimeric ribosomal subunit component, an RNA polymerase or a detector molecule. Such humanized antibodies may be generated using well known methods in any convenient mammalian source capable of producing antibodies, including, but not limited to, mice, rats, rabbits, or other vertebrates. Suitable cells for constant region and framework DNA sequences and host cells in which the antibodies are expressed and secreted, can be obtained from a number of sources, for example, American Type Culture Collection, Manassas, Va.

In addition to the humanized antibodies discussed above, other modifications to native antibody sequences can be readily designed and manufactured utilizing various recombinant DNA techniques well known to those skilled in the art. Moreover, a variety of different human framework regions may be used singly or in combination as a basis for humanizing antibodies directed to a chimeric RNA polymerase or a chimeric ribosomal subunit component, an RNA polymerase or a detector molecule. In general, modifications of genes may be readily accomplished using a variety of well-known techniques, such as site-directed mutagenesis (Gillman and Smith, Gene, 8:81-97 (1979); Roberts et al., 1987, Nature, 328:731-734).

Alternatively, a phage antibody library may be generated. To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (2001, Molecular Cloning: A Laboratory Manual, Cold Spring Harbor Laboratory, New York).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (992, Critical Rev. Immunol. 12:125-168).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/ phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222: 581-597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

VII. Methods

The present invention is based in part on the fact that many transcriptional analyses rely upon in vitro and in vivo assays, but these assays do not cover the broad range of transcription that occurs in live cells in real time. The methods and compositions disclosed herein allow real time detection of transcription in live cells, over a time course of minutes. The present methods are also useful for rapid expression profiling of isolated RNA populations. As disclosed elsewhere herein, monitoring the real-time production of RNA in the cellular nucleus is the most direct way to visualize in vivo transcription.

RNA polymerase is the enzyme that binds to cellular DNA and copies the DNA template into RNA. Mechanistically, when an RNA polymerase binds to DNA, the protein undergoes a conformational change that produces an RNA exit pore near the N-terminus of the protein where the newly synthesized RNA exits the RNA polymerase-DNA complex. A detector molecule placed near the RNA exit pore can detect the RNA as it is leaving the complex. Each gene that is being transcribed gives rise to a RNA of unique sequence.

The methods and compositions disclosed herein allow the sequence specific detection of a newly synthesized RNA as it exits the polymerase-DNA complex. The detector molecule disclosed herein is a hybrid peptide comprising a PNA that has been engineered to contain various sequences that permit cellular entry and nuclear localization to facilitate annealing of the PNA to a complementary sequence on RNA as it exits. The annealing of the PNA with an RNA sequence is detected by the interaction of at least two fluorescent molecules that have been engineered into the detector molecule and, preferably, flank the PNA sequence. Differences in fluorescent molecule interaction are detectable by changes in FRET or fluorescence polarity measurements. The detector molecule of the present invention is designed to bind in close proximity to the RNA exit pore of a chimeric RNA polymerase. To accomplish this, a targeting sequence, e.g. CRPBD, has been engineered into the detector molecule that will permit its binding to the detector binding domain of a chimeric RNA polymerase. Further, the detector binding domain has been engineered into an RNA polymerase near the region of the polymerase that forms the RNA exit pore. Upon addition of the detector molecule to live cells, the detector molecule crosses the cellular membrane, moves into the nucleus and binds to the RNA polymerase that is bound to genes that are to be transcribed. The signaling moiety of the detector molecule, upon interaction of the PNA with the complementary RNA sequence, generates a signal detectable by a shift in the FRET or fluorescence polarity of the detector molecule signaling moiety, preferably fluorescent molecules. Each time the PNA of a detector molecule bound to a chimeric RNA polymerase encounters a complementary sequence in the nascent RNA, a change in the fluorescent signal (blink) occurs. The time between these blinks correlates with the distance between the annealing sequences on the RNA. Upon retrieval of 3-4 blinks, the time differences are algorithmically compared to nucleotide sequences that have been deposited in a public nucleic acid database. Therefore, the transcription of individual genes is assessed. Individual gene signals are detectable since the genes are immobile in the genome, and consequently the blinks for any particular gene should occur in a localized spot in the genome. These blinks can be detected and quantified by confocal fluorescence and polarity microscopy, as well as by other methods disclosed elsewhere herein and known in the art.

As disclosed elsewhere herein, the detector molecule will specifically bind to a chimeric RNA polymerase through a CRPBD. The CRPBD will bind to a chimeric RNA polymerase at a specific epitope in an RNA polymerase, such as the SH3-domain of beta-PIX, which has been engineered into a specific region of an RNA polymerase, such as a T7 RNA polymerase, as described herein. SH3-domains mediate protein-protein interactions in a wide variety of signaling pathways in eukaryotic cells. SH3 domains bind to polyproline motifs. For instance, the SH3-domain of beta-PIX interacts with a small proline-rich region of 24 amino acids (SEQ ID NO:16) from a protein named alpha-PAK. The detector molecule further comprises a signal moiety of at least two fluorescent moieties, including, but not limited to, fluorescein (a donor) and tetramethylrhodamine (TAMRA; an acceptor), or analogs thereof, and PNA trimer, such as gtg. The fluorescent molecules are positioned such that fluorescence resonance energy transfer (FRET) or fluorescent polarity associations occur between the fluorescent molecules.

The detector molecule binds to the SH3 domain of the chimeric T7 RNA polymerase in such a way that the PNA trimer is positioned near the exit pore. When the RNA exits the pore, the PNAs base pair with their complementary bases. During this base pairing, the associated fluorescent molecules move apart and create a FRET signal, i.e. increasing fluorescence from the donor fluorophore fluorescein. As the RNA chain grows, differences in FRET occur only when the PNAs recognize their complements. This causes a blinking with increasing fluorescence from fluorescein and decreasing fluorescence from TAMRA that can be detected with polarity and optical methodologies disclosed elsewhere herein. The difference in time distance between the blinking can be transformed into nucleotide sequences characteristic of each mRNA sequence. Databases are then searched in order to elucidate the identity of the RNA being synthesized.

Thus, the present invention is based, in part, on the novel discovery that the transcription of DNA and the translation of RNA can be detected and monitored in real-time in a live cell or tissue. As disclosed herein, a detector molecule can be used to monitor and characterize the sequence of a nascent RNA molecule, which can then be used to determine the rate and conditions under which gene expression takes place.

The present invention is also based, in part, on the novel discovery that a chimeric RNA polymerase and a detector molecule can be used to rapidly sequence a nucleic acid molecule attached to a substrate without the use of conventional sequencing reactions and techniques.

A. Methods of Detecting Transcription of an RNA Molecule

The present invention includes a method for detecting the transcription of a DNA molecule as it is transcribed into an RNA molecule in a cell, tissue or organism in real time. The method comprises contacting a cell with a chimeric RNA polymerase comprising a detector binding domain. The method further comprises contacting a cell with a detector molecule that is capable of binding to the detector binding domain of the chimeric RNA polymerase via the CRPBD of the detector molecule. The detector molecule comprises a CRPBD, a signaling moiety and a PNA complementary to a portion of the RNA molecule emerging from the chimeric RNA polymerase via the exit pore of the RNA polymerase. The present method further comprises the step of detecting the signal generated by the signaling moiety produced by displacement of a fluorescent molecule on the detector molecule in relation to another fluorescent molecule in the signaling moiety. The displacement of the fluorescent molecule is caused by the binding of a PNA of the detector molecule to a portion of a nascent RNA molecule. The binding of the nascent RNA to the PNA causes the displacement of a fluorescent molecule, resulting in a detectable polarity or fluorescent energy resonance transfer (FRET) signal. The signal is detected using method well known in the art, including microscopy, confocal microscopy, exposure to light sensitive film, or the use of an apparatus that can detect fluorescent and polarity changes, for example, POLARSTAR OPTIMA or FLUOROSTAR (BMG Labtech, Durham, N.C.).

The cell is contacted with the chimeric RNA polymerase by placing the chimeric RNA polymerase in solution with the cell. The chimeric RNA polymerase localizes to the nucleus of the cell via the endogenous RNA polymerase nuclear localization signal (NLS) present on an RNA polymerase. Nuclear localization signals are well known in the art and are incorporated into nuclear proteins, including polymerases. Further, by virtue of a cell penetrating peptide engineered into a chimeric polymerase or otherwise conjugated to the chimeric polymerase, the chimeric polymerase can cross the cellular membrane. Alternatively, in another embodiment of the present invention, methods known in the art, such as electroporation, photoporation, cholesterol-modified chimeric polymerase or lipid-mediated transfer, are employed to introduce a chimeric polymerase into a cell.

The chimeric RNA polymerase can further be expressed in a cell or tissue by inducing a recombinant cell to express an isolated nucleic acid encoding a chimeric RNA polymerase using methods disclosed elsewhere herein. As a non-limiting example, a recombinant cell comprising a vector in which the vector encodes a recombinant isolated nucleic acid can be induced to express a chimeric RNA polymerase. The cell, once expressing a chimeric RNA polymerase, can then be contacted with a detector molecule to practice the method of the present invention.

The detector molecule binds to the chimeric RNA polymerase via a specific binding between a detector binding domain on the chimeric RNA polymerase and a CRPBD on the detector molecule. The detector binding domain and the CRPBD can be any two polypeptides that specifically bind each other, preferably an SH3 domain, an α-PAK domain, the components of a leucine zipper and the like. Further, as disclosed elsewhere herein, the detector binding domain and the CRPBD can comprise non-peptide molecules that specifically bind each other, including, but not limited to, biotin, avidin and streptavidin.

As disclosed elsewhere herein, the detector molecule comprises a PNA complementary to a portion of the RNA molecule emerging from the exit pore of the RNA polymerase. The PNA is covalently bound to the detector molecule and binds to the nascent RNA. Preferably, the PNA binds from about one to about ten RNA bases, even more preferably, from about one to about five RNA bases, even more preferably about two to about three RNA bases. Preferably, the PNA binds three RNA bases.

The detector molecule disclosed herein further comprises a signaling moiety attached to the detector molecule. More specifically, at least one fluorescent molecule of the signaling moiety is attached to the CRPBD of the detector molecule and at least a second fluorescent molecule of the signaling moiety is attached, either directly or indirectly, to the PNA. Even more specifically, the fluorescent molecules comprising the signaling moiety are separated from each other by at least the PNA.

The detector molecule can further comprise a cell penetrating peptide (CPP), such as a transportant (TP) peptide, a TP10 peptide, a pVEC peptide, a penetratin peptide, a tat fragment peptide, a signal sequence based peptide, an amphiphilic model peptide and the like. The CPP can be used to direct the detector molecule into the interior of a cell in order to selectively bind a chimeric RNA polymerase molecule such that the method of the present invention can be practiced.

When the nascent RNA emerges from the exit pore of the chimeric RNA polymerase, the PNA binds to a portion of the nascent RNA via hydrogen bonds between the complementary base pairs. The binding of the nascent RNA to the PNA results in the displacement of a second fluorescent molecule in the signaling moiety. The displacement of a fluorescent molecule is relative to the position of a first fluorescent molecule, resulting in the generation of a detectable signal. The detectable signal, thus detected, indicates that an RNA molecule having a sequence complementary to the PNA bound to the detector molecule has emerged from the exit pore of the chimeric RNA polymerase. The sequence of the PNA bound to the detector molecule, being known to the user of the present method, is then used to determine the sequence of the nascent RNA emerging from the exit pore of the chimeric RNA polymerase. The number and frequency of complementary binding events between the nascent RNA and the complementary PNA is compared to known sequences, and the transcription of specific genes is detected, thus detecting the transcription of a DNA molecule.

One of skill in the art, when armed with the present disclosure and the method disclosed herein, will realize that once a cell has been contacted with the molecules of the present invention, the transcription of DNA molecules can be investigated in real time in a cell, as opposed to the in vitro method present known in the art. In addition, the skilled artisan will readily realize that the conditions the cell, tissue or organism are subjected to can be varied in order to determine the effect of these conditions on the transcription of genes in the cell, tissue or organism.

In addition, the present invention further comprises a method of detecting transcription of a DNA molecule comprising contacting a cell with a recombinant RNA molecule and a detector molecule, which are bound to each other via the detector binding domain on the chimeric RNA polymerase molecule and the CRPBD of the detector molecule before the polymerase/detector molecule complex is placed in contact with a cell. That is, the present invention comprises a method of detecting transcription of a DNA molecule comprising contacting a cell with one large molecule (a nucleopeptide conjugate complex) comprising the chimeric RNA polymerase and the detector molecule attached through selective binding.

The present method is carried out essentially as disclosed elsewhere herein with the exception that the chimeric RNA polymerase and detector molecule are selectively bound to each other before they are put in contact with a cell.

The present invention further encompasses a method wherein an RNA polymerase is expressed or otherwise allowed to enter the interior of a cell, for example, by virtue of a nuclear localization signal, by electroporation, chemical transformation, and the like. The detector molecule is selectively bound to a subunit that binds an RNA polymerase during the course of DNA transcription. RNA polymerases contemplated in the present invention include, but are not limited to, the $\alpha$, $\beta$, $\beta'$ and $\sigma$ subunits of a eukaryotic RNA polymerase and the T7 polymerase. The detector molecule can be bound to a subunit via a selective binding event between two proteins as described elsewhere herein, or the detector molecule can be bound to an RNA polymerase subunit through the selective binding of an antibody to an RNA polymerase subunit, as disclosed elsewhere herein. The detector molecule/RNA polymerase subunit complex is then placed in contact with a cell as described elsewhere herein. The subunit, upon binding with the RNA polymerase, places the detector molecule in position to detect the transcription of a DNA molecule as described herein. Thus, the present invention comprises a detector molecule further comprising an RNA polymerase subunit, including, but not limited to the $\alpha$, $\beta$, $\beta'$ and $\sigma$ subunits of an RNA polymerase and/or the T7 polymerase.

B. Method of Detecting Translation of an RNA Molecule

The present invention further comprises a method for detecting the translation of an RNA molecule into a peptide. That is, the present invention includes a method of determining, in real time and in live cells, the frequency of translation of an mRNA molecule, as well as the sequence of the resulting peptide.

The method of the present invention comprises contacting a cell with a chimeric ribosome comprising a chimeric ribosomal subunit component. The method further comprises contacting a cell with a detector molecule that is capable of binding to the detector binding domain of the chimeric ribosome via the CRBD (chimeric ribosome binding protein) of the detector molecule. The detector molecule comprises a CRBD, a signaling moiety and a PNA complementary to a portion of the RNA molecule emerging from the chimeric ribosome via the exit pore of the 30s subunit of the ribosome. The present method further comprises the step of detecting the signal generated by the signaling moiety produced by displacement of a fluorescent molecule on the detector molecule in relation to another fluorescent molecule in the signaling moiety. The displacement of the fluorescent molecule is caused by the binding of a emerging RNA nucleotide to the PNA of the detector molecule. The binding of the emerging mRNA to the PNA causes the displacement of a fluorescent molecule, resulting in a detectable polarity or fluorescent energy resonance transfer (FRET) signal. The signal is detected using methods well known in the art, including microscopy, confocal microscopy, exposure to light sensitive film, or the use of an apparatus that can detect fluorescent and polarity changes, for example, POLARSTAR OPTIMA or FLUOROSTAR (BMG Labtech, Durham, N.C.).

In addition, the present invention encompasses the use of quantum dots as an emitter of fluorescence and a fluorescent molecule, such as fluorescein, or other fluorescent molecules described herein or known in the art, to detect a fluorescent and/or polarity shift detectable by the methods presently disclosed. Quantum dots produce fluorescence with little photobleaching and are described in, for example, U.S. Pat. Nos. 6,322,901; 6,576,291; 6,423,551; 6,251,303; 6,319,426; 6,426,513 and 6,444,143 and are available commercially (Quantom Dot Corp., Hayward, Calif.).

The cell is contacted with the chimeric ribosome by placing the chimeric ribosome in solution with the cell. The chimeric ribosome localizes to the cytoplasm of the cell. Further, by virtue of a CPP engineered into a chimeric ribosome or otherwise conjugated to a chimeric ribosome, the chimeric ribosome can cross the cellular membrane. Alternatively, in another embodiment of the present invention, methods known in the art, such as electroporation, photoporation, cholesterol-modified chimeric polymerase or lipid-mediated transfer, are employed to introduce a chimeric ribosome into a cell.

The chimeric ribosome can further be expressed in a cell or tissue by inducing a recombinant cell to express an isolated nucleic acid encoding a chimeric ribosomal subunit component using methods disclosed elsewhere herein. As a non-limiting example, a recombinant cell comprising a vector in which the vector encodes a recombinant isolated nucleic acid can be induced to express a chimeric ribosome or a chimeric ribosomal subunit component. The cell, once expressing a chimeric ribosome or chimeric ribosomal subunit component, can then be contacted with a detector molecule to practice the methods of the present invention.

The detector molecule binds to the chimeric ribosome via specific binding between a detector binding domain on the chimeric ribosome and a CRBD on the detector molecule.

The detector binding domain and the CRBD can be any two polypeptides that specifically bind each other, preferably an SH3 domain and an α-PAK domain or the components of a leucine zipper. Further, the detector molecule and CRBD can comprise non-peptide molecules that specifically bind to each other, including, but not limited to, biotin, avidin and streptavidin.

The detector binding domain and the CRBD (or the CRPBD or the CEBD) preferably bind to each other through the interaction of two proteins that specifically bind each other. However, the present invention is not limited to proteins that specifically bind each other, but also includes non-protein molecules that bind to each other, such as biotin and avidin or biotin and streptavidin. In addition, the use of antibodies, or antibody fragments, such as Fv fragments produced in phage display libraries, is encompassed in the present invention. In addition, a detector binding domain or a CRBD or a CRPBD or CEBD can comprise a metal molecule, such as a divalent or trivalent ion, and the conjugate binding partner can comprise a chelating agent that specifically binds a metal ion.

As disclosed elsewhere herein, the detector molecule comprises a PNA complementary to a portion of the RNA molecule emerging from the exit pore of the ribosome. The PNA is covalently bound to the detector molecule and comprises a series of nucleotides that bind to the emerging mRNA. Preferably, the PNA binds from about one to about ten nucleotides, even more preferably, from about one to about five nucleotides, even more preferably about two to about three nucleotides. Preferably, the PNA binds a tri-nucleotide.

The method disclosed herein further comprises a signaling moiety wherein the signaling moiety is attached to the detector molecule, more specifically, at least one fluorescent molecule of the signaling moiety is attached to the CRBD of the detector molecule and at least a second fluorescent molecule of the signaling moiety is attached, either directly or indirectly, to the PNA. Even more specifically, the fluorescent molecules comprising the signaling moiety are separated from each other by at least the PNA.

The detector molecule can further comprise a CPP, such as a TP peptide, a TP10 peptide, a pVEC peptide, a penetratin peptide, a tat fragment peptide, a signal sequence based peptide, an amphiphilic model peptide and the like. The CPP can be used to insert the detector molecule into the interior of a cell in order to selectively bind a chimeric RNA polymerase molecule such that the method of the present invention can be practiced.

When the translated mRNA emerges from the exit pore of the chimeric ribosome, the PNA binds the emerging mRNA via bonds between the complementary base pairs. The binding of the mRNA to the PNA results in the displacement of a second fluorescent molecule in the signaling moiety. The displacement of a fluorescent molecule is relative to the position of a first fluorescent molecule, resulting in the release of a detectable signal. The detectable signal, thus detected, indicates that an RNA molecule having a sequence complementary to the PNA bound to the detector molecule has emerged from the exit pore of the chimeric ribosome. The sequence of the PNA bound to the detector molecule, being known to the user of the present method, is then used to determine the sequence of the RNA emerging from the exit pore of the chimeric ribosome. The number and frequency of complementary binding events between the RNA and the complementary PNA is compared to known sequences, and the translation of specific genes is detected, thus detecting the translation of an RNA molecule.

One of skill in the art, when armed with the present disclosure and the method disclosed herein, will realize that once a cell has been contacted with the molecules of the present invention, the translation of RNA molecules can be investigated in real time in a cell, as opposed to the in vitro method present known in the art. In addition, the skilled artisan will readily realize that the conditions the cell, tissue or organism are subjected to can be varied in order to determine the effect of these conditions on the translation of mRNAs in the cell, tissue or organism.

In addition, the present invention further comprises a method of detecting translation of an RNA molecule comprising contacting a cell with a chimeric ribosome and a detector molecule, which are bound to each other via the detector binding domain on the chimeric ribosome molecule and the CRBD of the detector molecule before the chimeric ribosome/detector molecule complex is placed in contact with a cell. That is, the present invention comprises a method of detecting translation of an RNA molecule comprising contacting a cell with one large molecule comprising the chimeric ribosome and the detector molecule attached through specific binding.

The present method is carried out essentially as disclosed elsewhere herein with the exception that the chimeric ribosomal subunit component and detector molecule are selectively bound to each other before they are put in contact with a cell.

The present invention further encompasses a method wherein an ribosome is expressed or otherwise allowed to enter the interior of a cell, for example, by virtue of a liposome, by electroporation, chemical transformation, and the like. The detector molecule is selectively bound to an subunit of a ribosome, such as the 30s subunit or the 50s subunit, during the course of RNA translation. The detector molecule can be bound to a subunit via a selective binding event between two proteins as described elsewhere herein, or the detector molecule can be bound to an ribosome subunit through the selective binding of an antibody to an ribosome subunit, as disclosed elsewhere herein. The detector molecule/ribosome subunit complex is then placed in contact with a cell as described elsewhere herein. The subunit, upon binding with the other ribosomal subunit, places the detector molecule in position to detect the translation of an RNA molecule as described herein. Thus, the present invention comprises a detector molecule further comprising a ribosome subunit, including, but not limited to, the 50s and 30s subunit of a prokaryotic ribosome.

C. Method of Sequencing Nucleic Acids

The present invention further comprises a rapid in vitro method for sequencing a nucleic acid without using traditional sequencing reactions or techniques. The present invention is useful for the rapid sequencing of a nucleic acid. In addition, the present invention is useful for the identification of an isolated nucleic acid from a patient or a biological sample wherein an nucleic acid is isolated from a patient or a biological sample, sequenced using the methods of the present invention, and compared to known sequences of certain cell types. As a non-limiting example, a biological sample comprising tumor cells can be isolated from a patient and the nucleic acid from the biological sample can be sequenced and compared to known sequences of tumor cell nucleic acid in order to determine the identity of the tumor cells or the nucleic acid expression of a tumor cell. In addition, the present invention can be useful in comparing the expression of a nucleic acid in a cell or tissue when a stimulus is applied to the expression of the same nucleic acid from a known library of nucleic acids.

The method comprises attaching a double-stranded oligonucleotide comprising a promoter/regulatory sequence to a substrate. The substrate can be a glass slide, a plastic slide or dish, a nylon or cellulose membrane, and other such substrates well known in the art for conducting chemical and biological reactions. The promoter/regulatory sequence is attached to the substrate either directly, such as a covalent cross linking via glutaraldehyde, or through an intermediary, such as a biotin molecule. In the case of a biotin molecule, the substrate is coated with the corresponding binding partner, such as streptavadin. Other molecules well known in the art can be used to bind a promoter/regulatory sequence to a substrate and the present invention should not be construed as being limited to glutaraldehyde cross linking or biotin/streptavadin conjugation.

As an example, in one embodiment of the present invention, an amine-modified promoter/regulatory sequence is attached to a slide using an activated slide comprising, for example, a hydrophobic polymer containing N-hydroxysuccinimide ester reactive groups (CodeLink, Amersham, Piscataway, N.J.). In addition, a promoter/regulatory sequence is attached to a slide using UV crosslinking, siliconized quartz slides permitting chemical crosslinking, agarose or magnetic beads, and the like.

The oligonucleotide comprising the promoter/regulatory sequence is further digested with a restriction enzyme at the end opposite the end that is attached, either directly or indirectly, to the substrate. The oligonucleotide comprising the promoter/regulatory sequence is digested with any restriction enzyme known in the art to leave the oligonucleotide with sticky ends or blunt ends. Further, the promoter/regulatory sequence can be any known in the art, preferably the promoter/regulatory sequence for an RNA polymerase II, even more preferably the promoter/regulatory sequence for T7 RNA polymerase (TAATACGACTCACTATAGGG: SEQ ID NO:25).

In one embodiment, the promoter/regulatory sequence is synthesized as two complementary oligonucleotides comprising sticky ends, permitting ligation to complementary sticky ends. The synthesis of oligonucleotides is well known in the art.

A nucleic acid of interest is isolated from a cell, animal or tissue using methods well known in the art, such as TRIZOL based RNA isolation and the like. See Sambrook et al. (2001, Molecular Cloning: A Laboratory Manual, Cold Spring Harbor Laboratory Press, New York) and Ausubel et al. (1997, Current Protocols in Molecular Biology, Green & Wiley, New York). The nucleic acid of interest is then transcribed into a double stranded cDNA molecule using method well known in the art, such as transcription with reverse transcriptase. The double stranded cDNA is then digested with the restriction enzyme that was used to digest the oligonucleotide comprising the promoter/regulatory sequence such that the nucleic acid of interest has the corresponding sticky end or blunt end to the promoter/regulatory sequence. The promoter/regulatory sequence and the digested double stranded cDNA are then ligated together using methods well known in the art.

The promoter/regulatory sequence fused to a double stranded cDNA of interest is contacted with a chimeric RNA polymerase comprising a detector molecule. The chimeric RNA polymerase binds to the promoter/regulatory sequence and begins transcribing the double stranded cDNA of interest. The PNA of the detector molecule binds the nascent mRNA emerging from the chimeric RNA polymerase and emits a signal as described elsewhere herein. The signal is detected by a means for detection including, but not limited to, microscopy, confocal microscopy, multiphoton microscopy, exposure to light sensitive film, or the use of an apparatus that can detect fluorescent and polarity changes, for example, POLARSTAR OPTIMA or FLUOROSTAR (BMG Labtech, Durham, N.C.).

The signal thus detected is generated by the quenching and fluorescing of a fluorescent or polar signal emitted when the signaling moiety position is altered by the complementary binding of the PNA bound to the detector molecule and the nascent RNA. As described elsewhere herein, the PNA preferably binds a tri-nucleotide complement on the nascent RNA and causes a signal to be emitted. Thus, in order to sequence a nucleic acid of interest, the sequencing method of the present invention is performed substantially as described herein and is then repeated with a different PNA that binds a different sequence of the nascent RNA. Therefore, if the promoter/regulatory sequence and nucleic acid of interest are sequenced using a detector molecule with a PNA that binds, for example, CAC, a second reaction is performed using a chimeric RNA polymerase comprising a detector molecule wherein the detector molecule comprises a PNA having a sequence that does not bind CAC. The signal is detected by a means for detecting a signal as described elsewhere herein, and the results of the first reaction and the second reaction are compared and analyzed in order to determine the sequence, or a close approximation of the sequence, of the nucleic acid of interest.

VIII. Kits

The present invention encompasses various kits for detecting the transcription of an RNA molecule, the kit comprising a chimeric RNA polymerase, a detector molecule, and an instructional materials which describe use of the kit to perform the methods of the invention. These instructions simply embody the methods and examples provided herein. Although model kits are described below, the contents of other useful kits will be apparent to the skilled artisan in light of the present disclosure. Each of these kits is contemplated within the present invention. A kit is envisaged for each embodiment of the present invention.

The detector molecule of the present kit essentially includes the elements disclosed elsewhere herein. The detector molecule can comprise a cell penetrating peptide, a CRPBD that specifically binds a detector binding domain on a chimeric RNA polymerase, a signaling moiety comprising a fluorescent molecule and a PNA complementary to a portion of an RNA molecule. Preferably, the PNA binds a di-nucleotide or a tri-nucleotide, more preferably a tri-nucleotide. Preferably the fluorescent molecule is a ReAsH molecule, a BSR molecule, a Cy3B molecule, a Cy5 molecule, a fluorescein molecule, or another fluorescent molecule disclosed elsewhere herein.

The chimeric RNA polymerase included in a kit of the present invention can be an isolated polypeptide as described elsewhere herein, or can be expressed from an isolated nucleic acid as disclosed elsewhere herein.

In one embodiment of the present invention, the kit comprises an isolated chimeric RNA polymerase polypeptide. The isolated RNA polymerase polypeptide comprises, inter alia, a detector binding domain that specifically binds a CRPBD on a detector molecule described elsewhere herein.

In another embodiment of the present invention, the kit comprises an isolated nucleic acid encoding a chimeric RNA polymerase. The chimeric RNA polymerase encoded by the isolated nucleic acid of the present invention comprises, among other things, a detector binding domain that specifically binds a CRPBD on a detector molecule described elsewhere herein.

In yet another embodiment of the present invention, the kit comprises a chimeric ribosome for detecting the translation of an RNA to a protein. The kit comprises a chimeric ribosome subunit, or a fragment thereof, which further comprises a detector binding domain, and a variable linker region. The kit further comprises a detector molecule comprising a CRBD and a signaling moiety, such as a fluorescent molecule including a ReAsH molecule, a BSR molecule, a Cy3B molecule, a Cy5 molecule, a fluorescein molecule, or another fluorescent molecule disclosed elsewhere herein.

The chimeric ribosome included in a kit of the present invention can be an isolated polypeptide as described elsewhere herein, or can be expressed from an isolated nucleic acid as disclosed elsewhere herein.

In one embodiment of the present invention, the kit comprises an isolated chimeric ribosome polypeptide. The isolated chimeric ribosome polypeptide comprises, inter alia, a detector binding domain that specifically binds a CRBD on a detector molecule described elsewhere herein.

In another embodiment of the present invention, the kit comprises an isolated nucleic acid encoding a chimeric ribosome. The chimeric ribosome encoded by the isolated nucleic acid of the present invention comprises, among other things, a detector binding domain that specifically binds a CRBD on a detector molecule described elsewhere herein.

The kits of the present invention can further comprise additional reagents disclosed herein, such as plates and dishes used in the methods of the present invention, buffers, solutions and the like, as well as an applicator or other implements for performing the methods of the present invention. The kits of the present invention further comprise an instructional material.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1

Chimeric RNA Polymerase-SH3-T7 Fusion Constructs

The chimeric RNA polymerase of the present invention is engineered such that the detector molecule can associate with the detector binding domain of the chimeric RNA polymerase as the polymerase synthesizes RNA from the DNA template. An alpha-PAK domain and the SH3 domain of beta-PIX have been previously shown to associate in vivo and to have high interaction affinity. Accordingly, the beta-PIX SH3 domain has been engineered into the N-terminal region of T7 RNA polymerase.

Five constructs have been created in which the SH3-domain from Rat beta-Pix (AF044673; gi2865595, nt 1-189; SEQ ID NO:2) is cloned to the amino terminus of T7 RNA polymerase (NC_001604, nt 3171-5822; SEQ ID NO:1). In construct 1 (C1), the last amino acid of the SH3 domain is immediately followed by the T7 amino acid sequence, in constructs 2-5 ($C_2$-$C_5$), a 10 amino acid spacer peptide, containing zero to three prolines, respectively has been inserted between these two domains. The spacer peptide positions the two domains slightly apart from each other with increasing numbers of prolines providing more bend in the spacer peptide.

These prolines position the SH3 domain (detector binding domain) at equidistant positions around the spacer peptide α-helix. The spacer peptides that have been engineered into the chimeric RNA polymerase construct are 0-Prolines-GDKVQLIGFG (SEQ ID NO:17); 1-Proline-GEGLPGMCGG (SEQ ID NO:18); 2-Prolines-GPDDTPWDGG (SEQ ID NO:19); and 3-Prolines-GPPDTPYADG (SEQ ID NO:20). These spacer peptides permit more flexibility of the detector molecule bound to the chimeric RNA polymerase, so that the detector molecule can better interact with the nascent RNA. The α-helical nature of the spacer peptide positions the SH3 domain at a specific distance from the RNA exit pore.

The purification of T7 RNA polymerase from bacteria is a well established procedure (Davanloo et al., 1984 Proc. Nat'l. Acad. Sci. USA. 81: 2035-2039; Grodberg et al., 1988, J. Bacteriol. 170: 1245-1253; Zawadski et al., 1991, Nucleic Acids Res., 19: 1948; Li et al., 1999, Protein Expr. Purif. 16: 355-358) using standard protocols such as size exclusion and ion exchange columns. T7 RNA polymerase can be obtained from, for example, BL21-TIR bacteria, and a yield of several milligrams of protein from a 100 ml culture of BL21-TIR bacteria that have been engineered to express a chimeric RNA polymerase is readily possible.

The RNA polymerase constructs were cloned in the GATEWAY® vector system (InVitrogen, La Jolla, Calif.) so that shuttling between different experimental systems is facile. Five different bacterially-expressed chimeric T7 RNA polymerases have been made and the same five constructs are expressed in mammalian cells. While these constructs are appropriate choices for the initial experiments it may be necessary to position the capture peptide in other regions of the RNA polymerase to maximize the detectable signal, as disclosed elsewhere herein. This will be accomplished by performing insertional mutagenesis at various sites around the RNA exit pore, as is well known in the art.

The stepwise construction of C1 was performed as follows. The SH3 domain and T7 RNA polymerase were amplified by PCR in separate reactions using 5'phosphorylated primers at the ends that were to be ligated together (SEQ ID NO:8 and SEQ ID NO:9 for SH3; SEQ ID NO: 10 and SEQ ID NO:15 for T7) (SH3 3'-end and T7 5'-end). The SH3 and T7 RNA polymerase PCR products were ligated together. SH3-T7 ligation molecule was amplified by PCR using the ligation reaction as template. The correct size PCR product was extracted from an agarose gel. The SH3-T7 PCR product was cloned into pENTR/D-TOPO entry vector and transferred to expression vectors using GATEWAY® recombination system. Constructs 2-5 were created following the same strategy using 5' phosphorylated linker containing primers 0P/1P/2P/3P-T7-5'L in place of T7-5'L.

TABLE 2

Primer sequences

| Primer (SEQ ID NO.) | Sequence | Constructs |
|---|---|---|
| GWS-SHE-5'L (SEQ ID NO: 8) | cacc-atgactgataacgccaa cagcca | All |
| SH3-3'L (SEQ ID NO: 9) | P-gatctctcgtacgtagttg ct | All |

TABLE 2-continued

Primer sequences

| Primer (SEQ ID NO.) | Sequence | Constructs |
|---|---|---|
| T7-5'L (SEQ ID NO: 10) | P-atgaacacgattaacatcg ct | C 1 |
| 0P-T7-5'L (SEQ ID NO: 11) | P-ggcgataaggtccagctgat cggctttggc-atgaacacgat taacatcgct | C 2 |
| 1P-T7-5'L (SEQ ID NO: 12) | P-ggcgagggcctgccaggcat gtgtggcggc-atgaacacgat taacatcgct | C 3 |
| 2P-T7-5'L (SEQ ID NO: 13) | P-ggcccagatgatactccatg ggatggcggc-atgaacacgat taacatcgct | C 4 |
| 3P-T7-5'L (SEQ ID NO: 14) | P-ggcccaccagatactccata cgccgatggc-atgaacacgat taac | C 5 |
| T7-3'L (SEQ ID NO: 15) | ttacgcgaacgcgaagtccga | All |

"P" in the sequence indicates 5' phosphorylation

Figure 29:
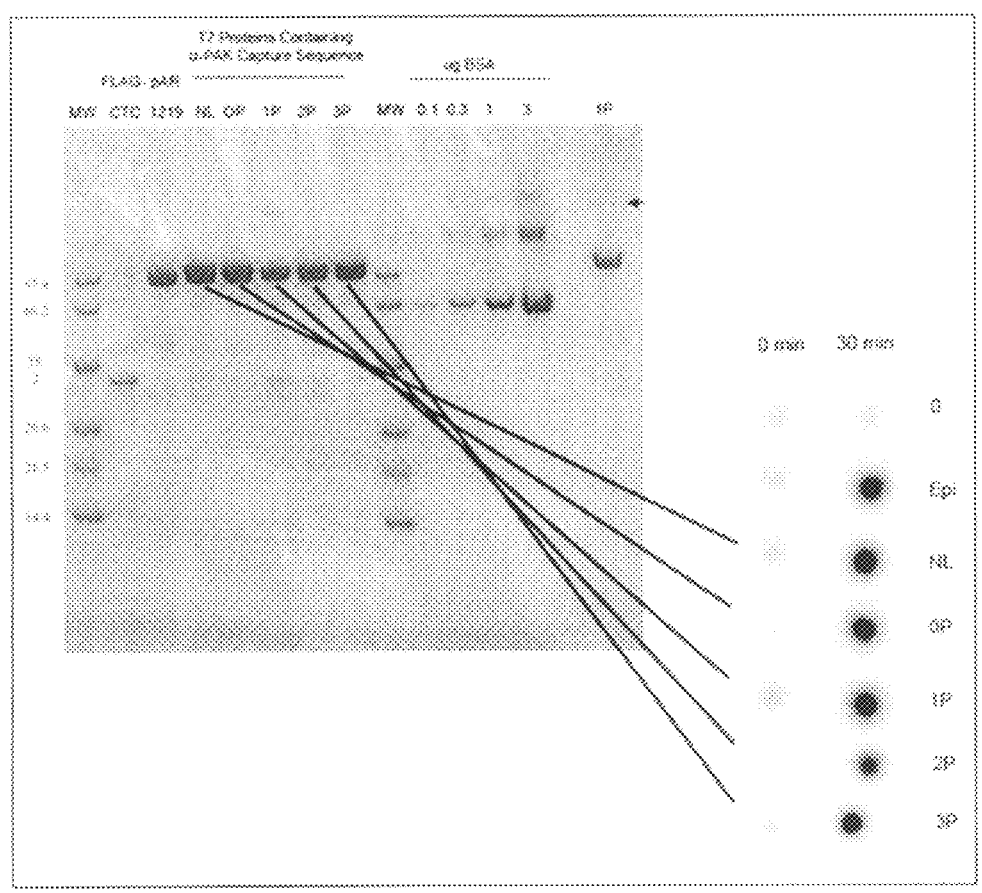
FIG. 29 is a series of two images. The image on the left depicts a denaturing protein gel of samples of proteins expressed from various chimeric T7 RNA polymerase constructs. NL=no spacer peptide. 0P=spacer peptide with one proline. 1P=spacer with two prolines. 3P=spacer peptide with three prolines. BSA=bovine serum albumin. FLAG-CTC=FLAG epitope tagged control (no T7 RNA polymerase). pAR 1219=expression vector expressing T7 RNA polymerase without a detector binding domain. Molecular weights of the MW markers are indicated next to the image of the gel. Image on the right depicts results of transcription assays, using the chimeric T7 RNA polymerases, at 0 minutes and 30 minutes. EPI=unmodified T7 RNA polymerase (EPICENTRE® Technologies, Madison, Wis.). The top row, labeled "0", had no RNA polymers added to the transcription reaction and serves as a background control.

BL21 bacteria were transformed with expression vectors comprising each of constructs C1-C5. The protein expressed from each chimeric T7 RNA polymerase construct was analyzed on a denaturing protein gel (FIG. 29). The levels of the protein can be estimated in comparison with the BSA protein-loading curve.

To assess whether the chimeric T7 RNA polymerases were still capable of synthesizing RNA, in vitro RNA transcription assays were performed. Chimeric RNA polymerase (30 ng) was added to an RNA transcription reaction containing a T7 RNA polymerase promoter-containing plasmid template and $P^{32}$-radiolabeled nucleotides. The radiolabeled nucleotides were incorporated into the nascent RNA. The 0 and 30 min time points for RNA synthetic capability of each of the cloned RNA polymerases are shown in the right hand panel of FIG. 29. Each of the chimeric T7 RNA polymerases exhibited RNA synthetic activity. Therefore, the insertion of a detector binding domain and a spacer peptide at the N-terminal of T7 RNA polymerase does not inactivate the enzyme. These modified RNA polymerases were then used in preliminary experiments for in vitro expression profiling.

Example 2

Synthesis of a Detector Molecule

The present Example describes the synthesis of different detector molecules for in vitro and in vivo studies using the methods of the present invention. Solid phase peptide synthesis (SPPS) using a t-butoxycarbonyl(t-Boc) strategy was used to synthesize peptides used to generate detector molecules. Specifically, SPPS was used to synthesize a peptide (L604) containing a C-terminal thioester, a linker, a PNA trimer and fluorescein; a peptide (L605) containing an α-PAK sequence and TAMRA; a peptide (L564) containing a C-terminal thioester, a linker, PNA trimer and fluorescein; and a peptide (L575) containing an α-PAK sequence, TAMRA and an N-terminal Cys. All of the peptides were purified by HPLC and subsequently analyzed by MALDI-TOF mass spectrometry.

Figure 12:
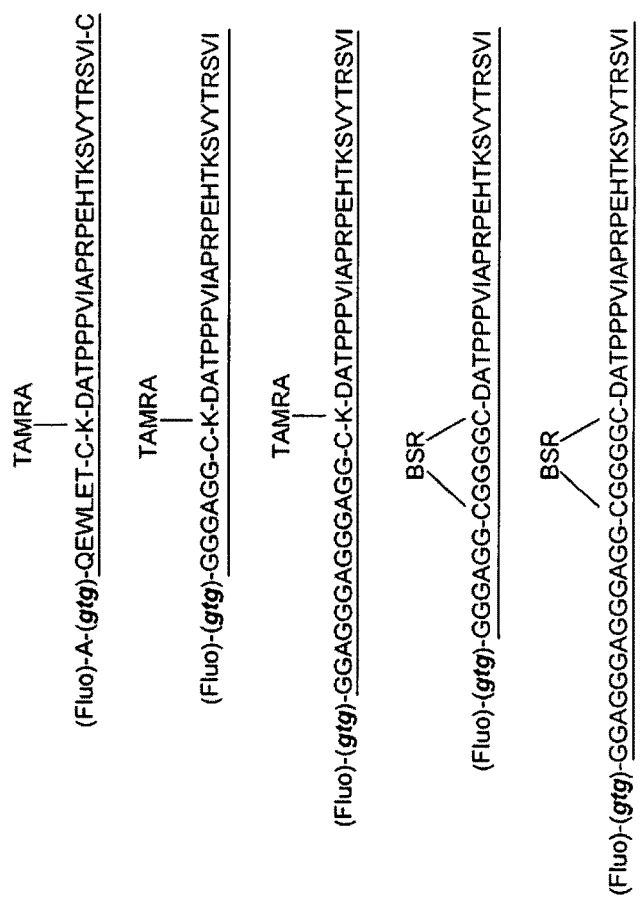
FIG. 12 is an image depicting multiple ligated detector molecules for in vitro detection of blinking signaling. The underlined portions are, top to bottom, SEQ ID NOs: 43, 40, 44, 45 and 46, respectively. Fluo=fluorescein. gtg=peptide nucleic acid (PNA). TAMRA=tetramethylrhodamine. The top three detector molecules have been synthesized (see Example 2).

Three different PNA-Linker peptides were ligated to an alpha-Pak-domain containing peptide to generate detector molecules for in vitro studies (top three molecules depicted in FIG. 12). Two other detector molecules contemplated for in vitro applications are also depicted in FIG. 12 (bottom two molecules).

Figure 11:
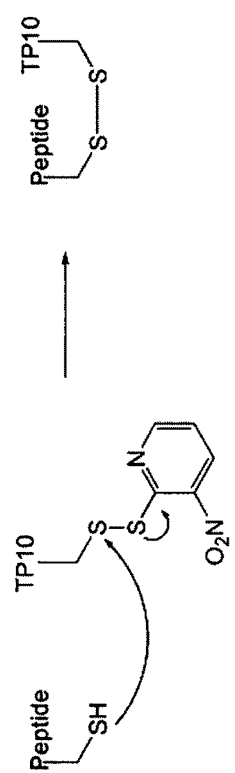
FIG. 11 is an image depicting disulfide formation between a peptide and the cell penetrating peptide (CPP) TP10, which contains 3-nitro-2-pyridinesulfenyl (Npys) activated Cysteine at its N-terminal.
Figure 13A:
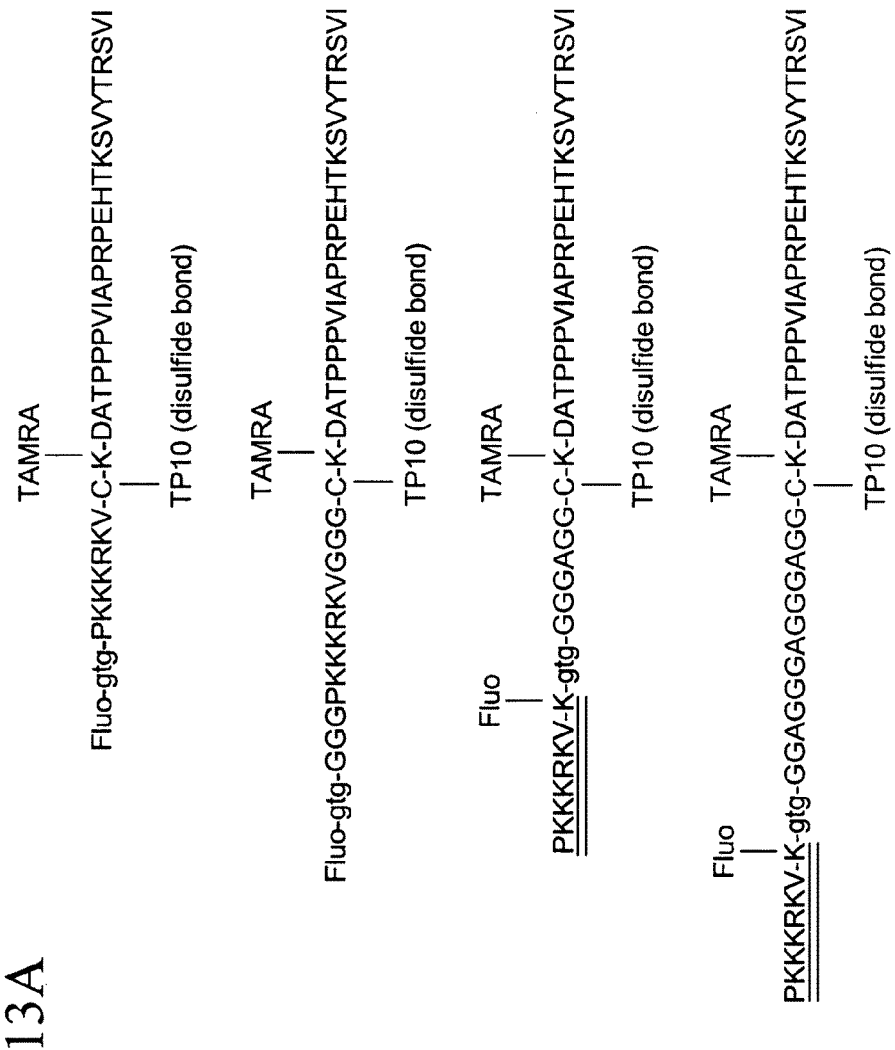
FIGS. 13A and 13B, is an image depicting multiple ligated detector molecules for in vivo detection of blinking signaling.
Figure 13B:

For in vivo studies, four different PNA-Linker peptides were ligated to an alpha-Pak-domain-containing peptide. Two of these contained an NLS as part of the linker (top two molecules in FIG. 13A). The other two contained an NLS attached to the PNA (bottom two molecules in FIG. 13A). Each of these were further coupled via disulfide bridge to a cell penetrating peptide, TP10, containing Npys activated Cys, (FIG. 11) to produce detector molecules. One in vivo detector molecule has been tested and the NLS successfully targeted the detector molecule to the cell nucleus. FIG. 13B depicts four other detector molecules contemplated for in vivo applications.

Figure 14:
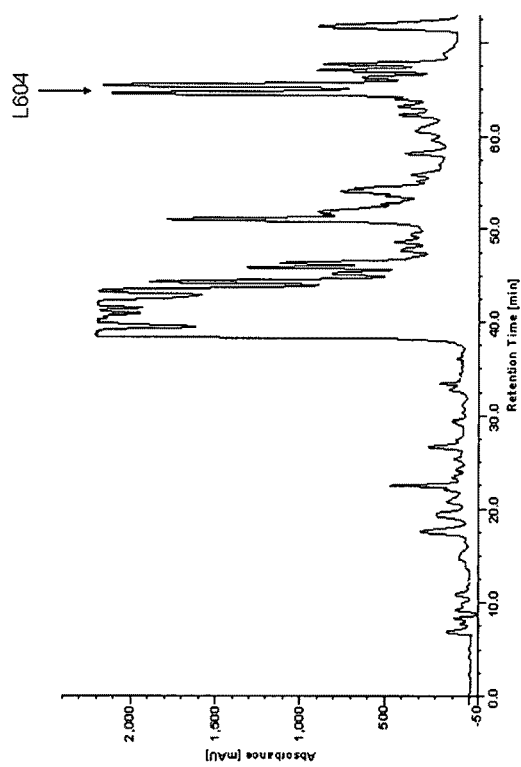
FIG. 14 is an image of the High Performance Liquid Chromatography (HPLC) spectrum of crude peptide L604.
Figure 15:
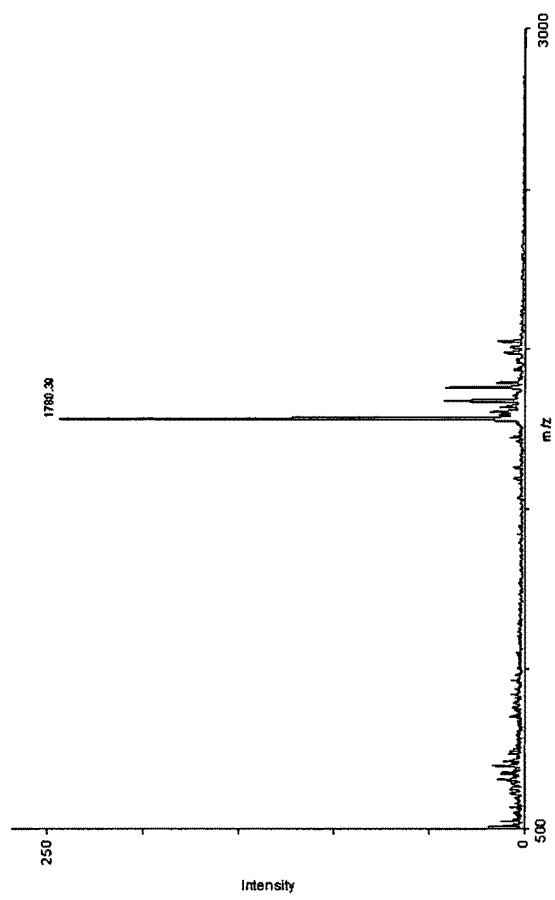
FIG. 15 is an image of the Matrix-Assisted Laser Desorption Time-of-Flight (MALDI-TOF) mass spectrum of the correct HPLC fraction of peptide L604.
Figure 16:
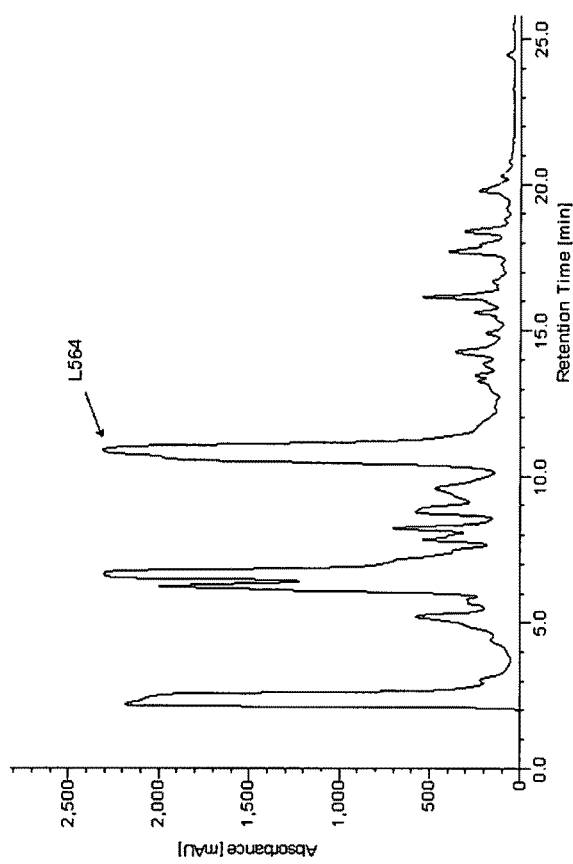
FIG. 16 is an image of the HPLC spectrum of crude peptide L564.
Figure 17:
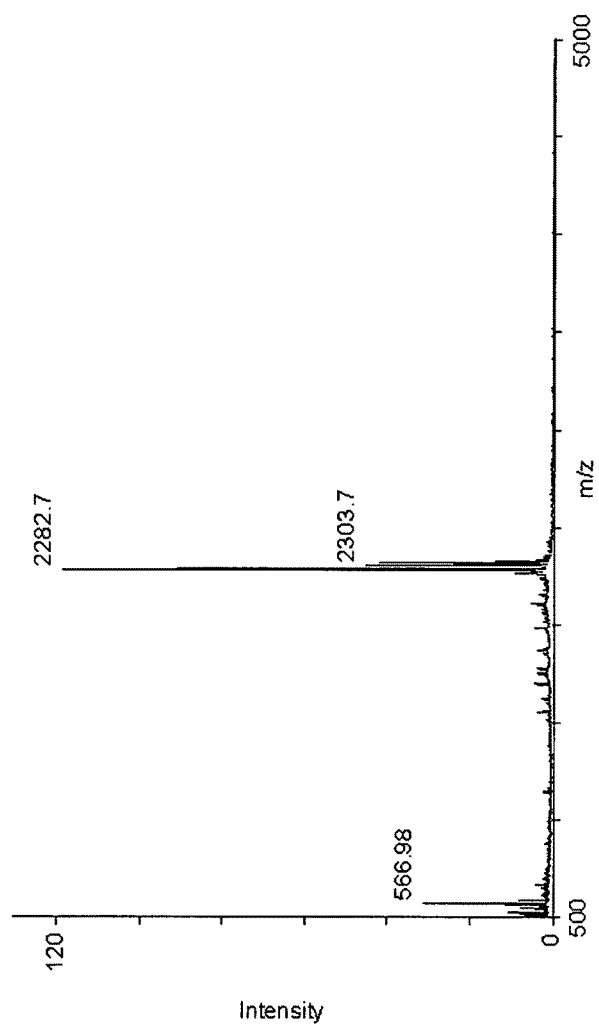
FIG. 17 is an image of the MALDI-TOF mass spectrum of the HPLC fraction containing peptide L564. The peaks at m/z 2282.7 and 2303.7 correspond to peptides L564 and L564 with sodium, respectively.

Two of the detector molecules (L606 and L602) and the TP10 sequence were synthesized as follows. To facilitate the synthesis of the thioester peptides, L604 and L564, a thioester peptide-producing resin linker for Boc chemistry-SPPS was used. Starting with the HF-labile MBHA resin, leucine was coupled followed by S-trityl mercaptopropionic acid by using standard SPPS conditions. The resulting resin was used as a starting resin for polypeptide-chain assembly after removal of the trityl protecting group by DCM/TFA/TIS. The desired thioester bond could be generated directly on the resin by coupling the remaining amino acids under standard coupling conditions. After HF cleavage, HPLC purification and subsequent mass spectrometry analyses, the C-terminal thioester peptides were used directly in NCL. The MALDI-TOF mass spectrometry data was recorded in the positive reflection mode. HPLC spectra of crude thioester peptides L604 and L564 can be seen in FIGS. 14 and 16, and the mass spectra of the correct fractions can be seen in FIGS. 15 and 17, respectively.

Figure 18:
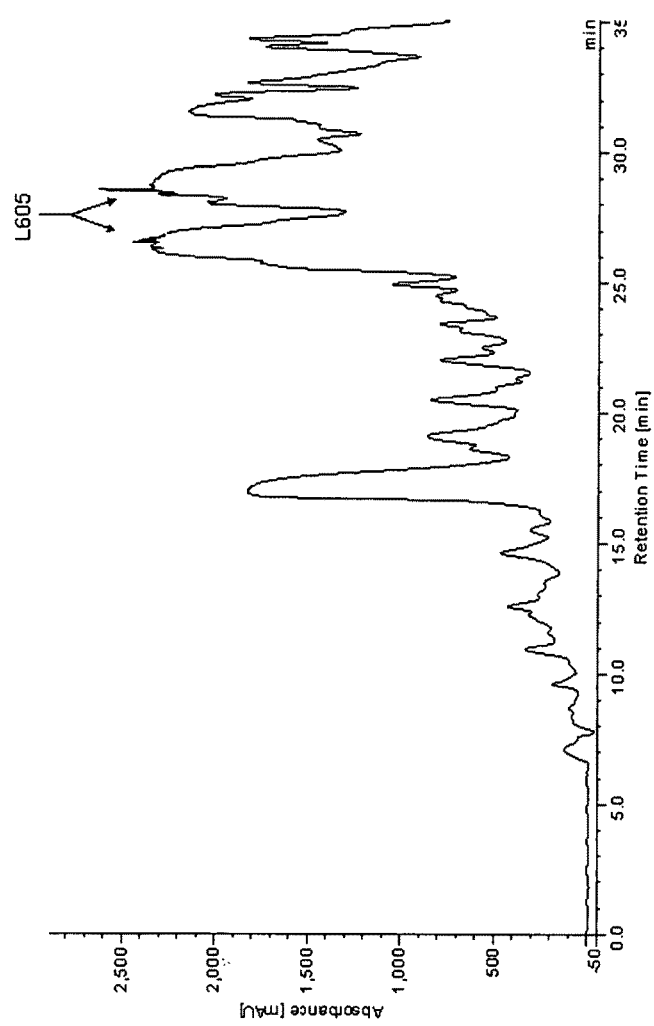
FIG. 18 is an image of the HPLC spectrum of crude peptide L605.
Figure 19:
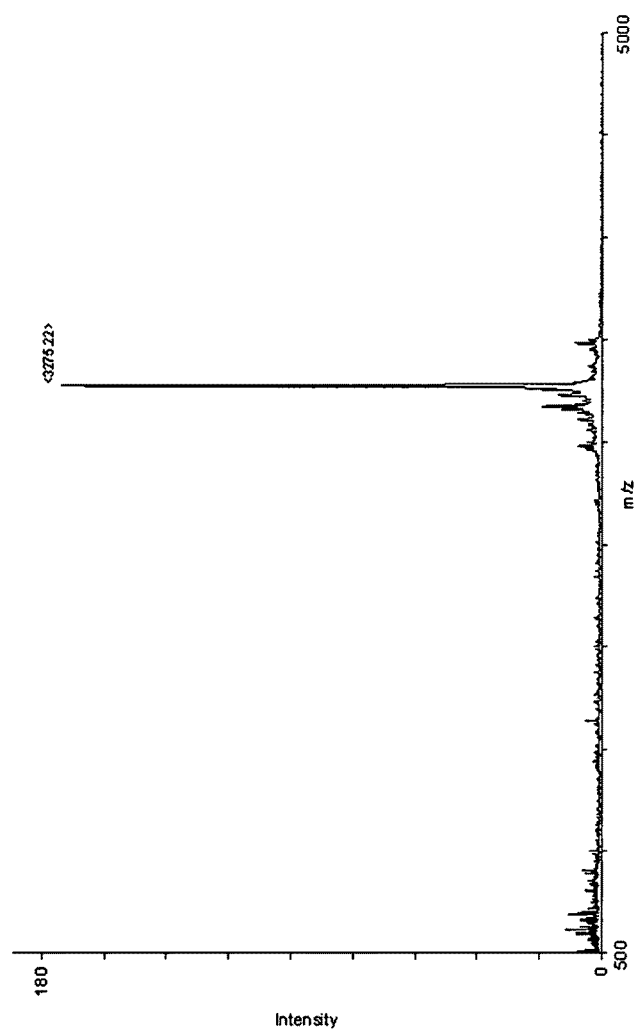
FIG. 19 is an image of the MALDI-TOF mass spectrum of the fraction containing peptide L605.
Figure 20:
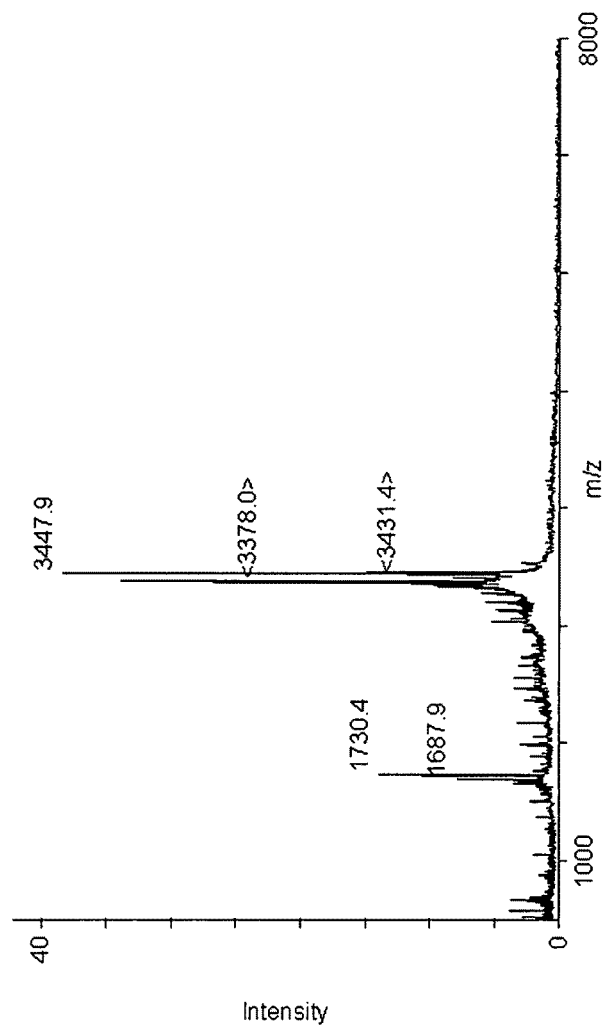
FIG. 20 is an image of the MALDI-TOF mass spectrum of crude peptide L575.

Peptides L605 and L575 were synthesized in a stepwise manner in a 0.1 millimolar scale on a peptide synthesizer (model 431A; Applied Biosystems, Framingham, Mass., U.S.A.) using a t-Boc strategy of SPPS. t-Boc amino acids were coupled as hydroxybenzotriazole esters to a p-methylbenzylhydrylamine resin (Bachem, Bubendorf, Switzerland) to obtain C-terminally amidated peptides. The peptides were treated with 20% piperidine in DMF to cleave off the Fmoc group on the $Lys^2$ side chain. TAMRA was dissolved in DMSO/DMF (1:1) together with 2 equivalents of DIEA and coupled over night to the $Lys^2$ side chain. HPLC and mass spectra for peptide L605 can be seen in FIGS. 18 and 19, and the mass spectrum for L575 can be seen in FIG. 20.

Figure 21:
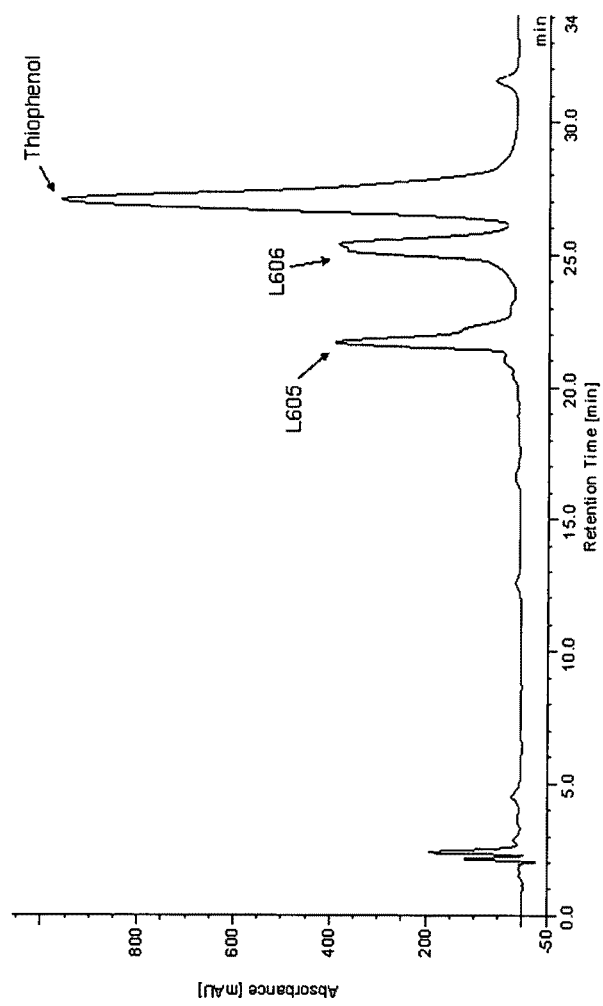
FIG. 21 is an image of the HPLC spectrum of NCL between peptides L604 and L605, resulting in peptide L606.
Figure 22:
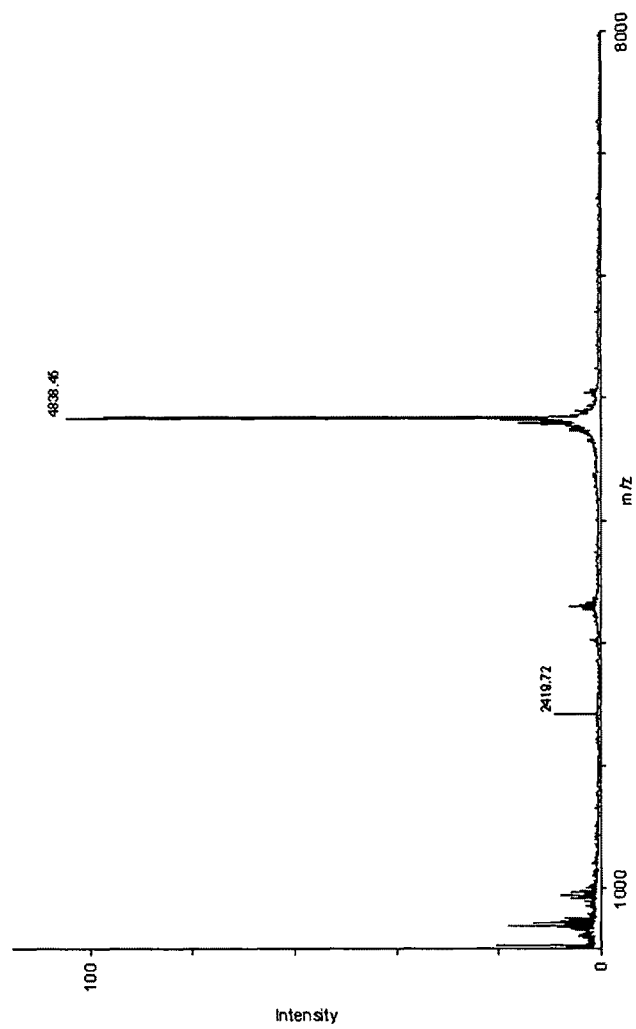
FIG. 22 is an image of the MALDI-TOF mass spectrum of the HPLC fraction containing peptide L606. The peaks at m/z 4838.5 and 2419.7 correspond to single and double charged peptide L606, respectively.

Native chemical ligation (NCL) between peptides L604 and L605, resulting in peptide L606, was performed in phosphate buffer, guanidine hydrochloride and thiophenol, at pH 7.2. The mixture was allowed to react overnight and was completed in 12 hours. HPLC spectrum of the NCL can be seen in FIG. 21 and the mass spectrum of the correct fraction can be seen in FIG. 22. NCL reaction for peptides L564 and L575, resulting in peptide L602, was performed similarly as for L604 and L605.

The detector molecules synthesized by the methods described herein can be optimizes in both terms of synthesis and function. As an example, the distance between the fluorescent molecules can be optimized to produce and receive the best signal. The CPP and/or nuclear localization signal can be modified for in vivo transcription detection.

Example 3

Expression Profiling and Sequencing

Figure 23:
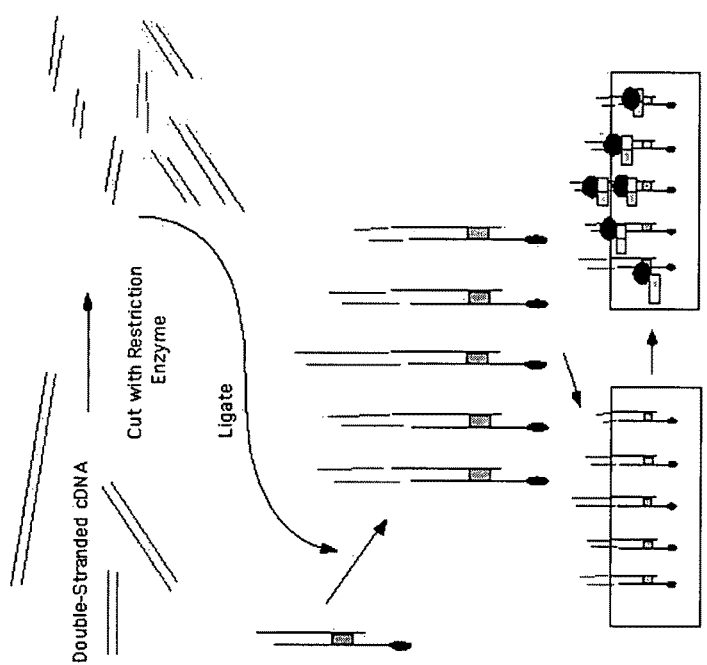
FIG. 23 is a schematic image depicting the detection of mRNAs on a microarray substrate. Oligonucleotides comprising a microarray binding moiety (dark oval), a T7 RNA polymerase promoter site (dark rectangle) and a restriction enzyme site are attached to an array and ligated to a restriction enzyme-digested cDNA. Chimeric RNA polymerase and detector molecule complexes are added.

Expression profiling and sequencing occurs on microarrays by ligating cDNA populations to short double-stranded oligonucleotide DNAs that are immobilized on the microarray (FIG. 23). These short DNA oligonucleotides are modified to facilitate the detection by the detector molecule using the methods of the present invention. DNAs are synthesized with a 5'-activatable amine on a 12-carbon extension on the 5'-end of the bound strand of the double-stranded oligonucleotide. The oligonucleotide also encodes a T7 RNA polymerase promoter site, a spacer region, and a ligatable restriction enzyme site, such as, for example, an EcoR1 site. The complementary oligonucleotide contains the complementary sequences minus the 5'-activatable amine but contains a 5'-phosphate. The sequence of this oligonucleotide is invariant between spots. The double-stranded oligonucleotide is spotted on amine-link glass slides using a GeneMachines OmniGrid arrayer (Ann Arbor, Mich.). The print density of these spots varies with each spot being about 150 microns in diameter with a 200 micron distance between the centers of adjacent spots.

Detection requires that individual DNAs must be distinguishable so the DNA density will vary between about 10,000 molecules per spot to about 250,000 molecules per spot. These densities differ so that multiple individual molecules are visible within a given field. Each row of spots is demarcated by a fluorescent molecule positioned at the beginning of each row.

After binding of the double-stranded oligonucleotide on the glass slides, a cDNA population is ligated directly to the immobilized oligonucleotide. The cDNA library is generated by conversion of mRNA into cDNA using a mixture of oligo-dT and random primers to initiate cDNA synthesis (FIG. 23). Both primers are used so that both the 3'-end of the RNA (oligo-dT primed) and sequences closer to the 5'-end of the RNA (random primed) are represented in the synthesized cDNA. Once the cDNA is synthesized, it is made double-stranded and digested with EcoR1. The digested DNA is ligated directly onto the microarray-immobilized oligonucleotides. Depending upon the ligation reaction, a concatemer of different cDNAs on each immobilized oligonucleotide can result. If the concatemer of different cDNAs causes difficulty in discerning distinct RNAs, then the EcoR1-digested cDNA is dephosphorylated so that self-ligation cannot occur, therefore biasing the ligation reactions towards ligation onto the immobilized oligonucleotides.

After ligation, the arrays are covered with a coverslip such that two ends of the coverslip are open, creating a chamber, so that solution can flow through the chamber. The chambered microarray is placed on the stage of a microscope capable of fluorescent stimulation and FRET detection. Alternatively, the slide is placed in the reaction/detection chamber of an automatic fluorescent detector, such as those described elsewhere herein. A chimeric T7 RNA polymerase, the in vitro detector molecule and NTPs are dialyzed or micropumped into the microarray chamber so that the chimeric RNA polymerase binds to the T7 RNA polymerase promoter, the detector molecule attaches to the RNA polymerase and, as RNA is synthesized, the fluorescein and TAMRA fluorescent molecules move relative to one another when the PNA binds to the complementary sequence on newly synthesized RNA as the RNA exits the RNA exit pore (FIG. 23).

A microarray was made by immobilizing amino-modified double-stranded DNA templates, containing the T7 RNA polymerase promoter site, on Codelink slides as described above. Two DNA templates were prepared. Actin cDNA and the pGEM cloning vector, each of which had a T7 RNA polymerase promoter operably linked to the coding sequence, were amplified using a 5'-PCR primer that was modified to contain a primary amine on a 16 carbon linker arm. This primary amine group was linked to the Codelink slide, thereby orienting the T7 RNA polymerase promoter such that transcription of the double-stranded DNA template would occur from the attached region of the DNA template to the free end of the template.

A mixture of three in vitro detector molecules comprising a gtg PNA (top three molecules in FIG. 12) was mixed with a mixture of all five chimeric RNA polymerases, added to the microarray and incubated in transcription buffer to transcribe the tethered DNA molecule into RNA. As shown in the enlarged image of the spotted array, detectable fluorescent signals are emitted during RNA transcription. The spots are imaged over time such that changes in fluorescence intensity can be detected and quantitated, therefore giving rise to the time- and sequence-dependent Blinker signal.

The blinking of the fluorescent molecules is assessed over the course of several minutes with the time between blinks measured. The blinking time associated with each RNA as it is being synthesized is plugged into a Constrained Local Dynamic Time Warp (CL-DTW) algorithm discussed elsewhere herein, developed by Dr. Junhyong Kim, that correlates time between blinking to the sequence of the nucleic acid. These data are used to query the rat, mouse and human databases for RNAs in which the sequence fits the blinking pattern. T7 RNA polymerase synthesizes RNA at the rate of about 80 bases per second, and consequently 12 microsecond resolution is required for resolution of single nucleotides. Since the methods described herein assess at least about three adjacent nucleotides though hybridization of the PNA trinucleotide sequence, the time resolution for detection of this trinucleotide sequence is significantly less stringent then 12 milliseconds. The frequency of finding 3 particular adjacent bases ($4^3$=1 in 64) divided by 80 bases/second equals 800 milliseconds which is the time between blinks. This time frame is easily discernable with available detectors known in the art.

Single molecule detection is assessed with the standard detection systems, described herein, but can also be assessed using a back-thinned multiplicative gain camera integrated into an inverted microscope that enhances single molecule resolution. Given the rate of RNA synthesis by RNA polymerase, imaging for just a few minutes is sufficient to unambiguously identify the ligated cDNAs.

The synthesis of various detector molecules that are optimal for FRET signal generation as well as fluorescence polarity measurements is described elsewhere herein. The distance between the fluorescent molecules for FRET is optimally 10-20 amino acids while for polarity measurements <10 amino acid separations are preferable. Therefore, detection can be supplemented or replaced using FRET or fluorescence detection, depending on the detector molecules of the present invention.

The selection of a trinucleotide PNA sequence on the detector molecule was made due to the relatively high annealing energies exhibited by PNAs with nucleic acids. Indeed, PNAs of 21 bases can have $T_m$'s as high as 90° C. The 3-base gtg PNA anneals transiently at 37° C. so that it can go on and off of the exiting RNA. This 3-base sequence described herein can also be extended to at least about 4 or 5 or 6 bases in length. The sequences of the 4-, 5- or 6-base PNAs is bioinformatically determined to maximize the number of interactions with a population of RNAs. This can be determined using known codon preferences, G:T ratios particular to a certain species, such as humans, mice or rats, and other characteristics of nucleic acids well known in the art.

The detectable blinking signal will unequivocally identify the ligated cDNAs. The number of different oligonucleotides that display detectable blinking signals for the same RNA permits an analysis of the abundance of that particular RNA in the initial RNA population. Sequencing of the ligated cDNAs is also possible using a combination of multiple trinucleotide PNA sequences in the detector molecule (Korn et al., 2003, Nucleic Acid Res., 31: 89). Thus, using all 64 different combinations of a trinucleotide allows complete sequence information to be obtained for any cDNA. This is done robotically in an iterative manner with one detector molecule being used, signal generated and then washed away and followed by another detector molecule with a different PNA sequence detector. Due to the way in which the detector molecule signal is generated, it is highly likely that the full complement of 64 combinations will not be necessary to determine the sequence of any given cDNA. Detector molecules with varying oligonucleotide sequences, such as a tri-nucleotide, can be synthesized using the methods disclosed elsewhere herein.

When the methods and compositions of the present invention are used to identify a novel RNA, the identity of the RNA can be confirmed independently. Confirmation of the RNA identity corresponding to the microarray blinking signal is determined by PCR. The sequence for the identified RNA is used to generate PCR primers to PCR amplify the sequence from the DNA spot on the microarray. This PCR reaction is carried out with the low density immobilized DNAs. Confirmation that the RNA is ligated to the microarray-immobilized DNA giving rise to the detectable blinking signal is afforded by one of the PCR primers being from the immobilized DNA which is 5' to the ligated cDNA. Further standard RNA amplification and microarray analysis can be performed to confirm that the same relative ratio of different transcripts as observed by the detectable blinking signal is parallel to that seen with the standard (although more time consuming) technology.

Example 4

Bioinformatic Analysis of In Vitro Blinker Signal

Signal Processing and Target Matching of Blinker Signals: After initial signal quantification from image capture and analysis, the measured Blinker signal is converted to transcript sequences. The approach starts with the generation of a library of candidate sequences. Each library sequences is converted into an in silico Blinker signal using a computational model of PNA:RNA duplex formation and detector response. The degree of match of a probe Blinker signal to the library of in silico target signals is quantified. Then, the best match and the reliability of the match is assessed statistically.

Figure 30:
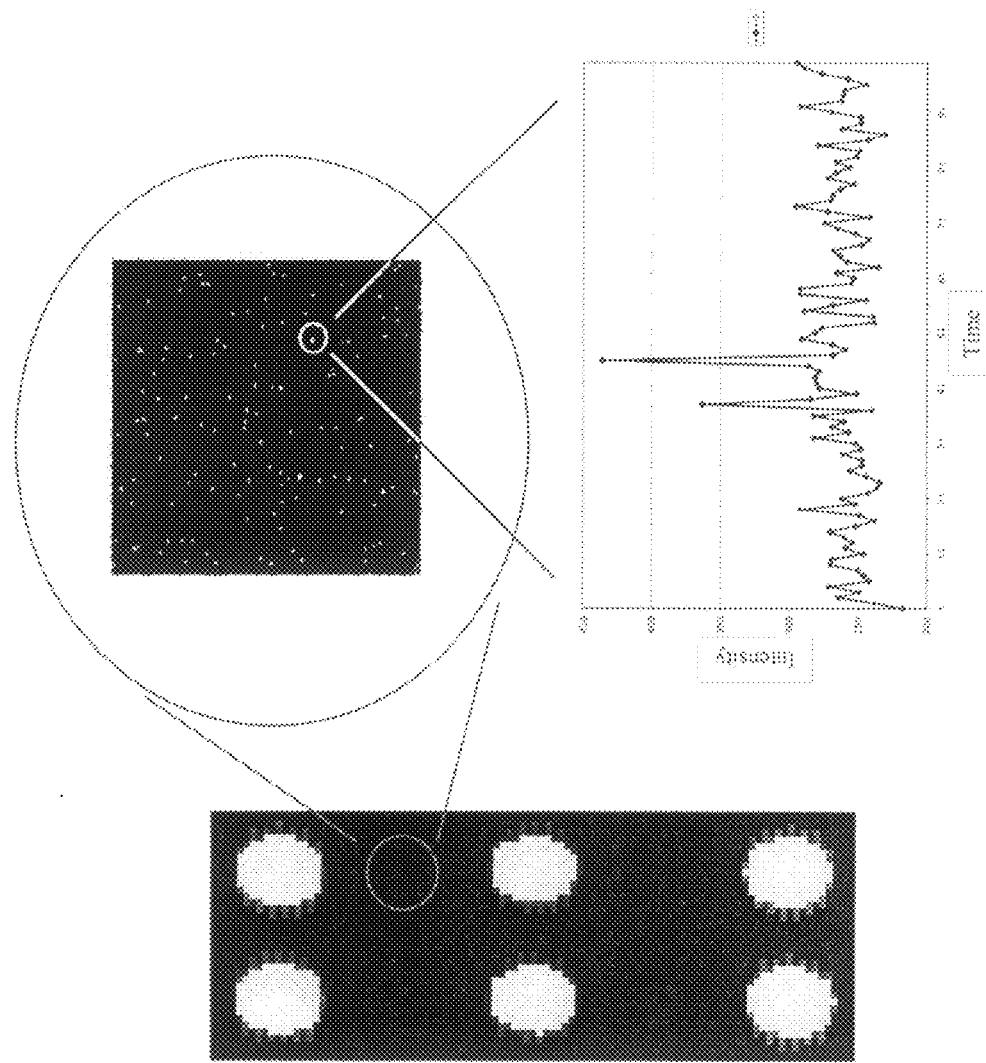
FIG. 30 is a series of images depicting a microarray onto which a Blinker detector molecule was spotted and a representative graph of a signal detected. The left image is of a microarray. The 6 large white circles are fluorescent orientation markers. An enlarged image of the circled region on the microarray is depicted at the top right. The fluorescent Blinker intensity signal from one spot is depicted as a function of time in the graph on the bottom right.

Generating a Library of In Silico Blinker Signals: The Blinker technique depends on detecting configuration changes in the PNA:RNA k-mer duplex through FRET. Given a k-mer PNA sequence, it is straightforward to compute the presence/absence of complementary k-mers in the target sequences. However, since the k-mer may form partial duplexes inducing differential modulation of the FRET response, there is more information in the Blinker signal than simple complementary matches. This can be seen in the graph in FIG. 30, where the measured Blinker signal has mixed modes of response peaks with the smaller peaks potentially corresponding to partial matches. Therefore, an in silico model of the Blinker signal for a candidate sequence is constructed first by computing a biophysical model of duplex configurations based on bonding free energies. A collection of candidate targets can be used to generate a library of in silico Blinker signals for comparison to the experimental probe signal.

Given a probe k-mer PNA sequence and a k-mer frame of a target transcript, the PNA and the RNA may be completely disassociated, bound at only the first position, bound only at the second position, and so on, for a total of $2^k$ configurations. The relative free energy of a duplex configuration is computed by summing the pair-bonding free energy values over the k-positions (for the subset of bonded positions) using a pre-determined parameter set, $[\Delta E_{ij} | i,j = \{A, C, G, U\}]$, that assigns bonding energy to each possible pair. In the preliminary data, the interactions were assumed to be transient and not strongly governed by stacking energy of the duplex helices. Therefore, −3 kcal, −2 kcal, and −1 kcal were assigned to C:G, A:U, and G:U pairs, respectively and zero to all other pairs. The probability of a potential configuration is computed using the quantity $$f(i) = e^{-\frac{1}{T}\sum_{p=1}^{k} \Delta E_{i(p),j(p)}}$$

for the ith configuration; the summation is over the k positional duplex state of the ith configuration, and T is the temperature parameter. Then the probability of the ith configuration is $$P(i) = f(i) \bigg/ \sum_{i=1}^{2^k} f(i).$$

Each duplex configuration implies a certain interaction distance between the coupled fluorescent molecules. For example, if the duplex is completely bound in all k positions, the fluorescent molecules are assumed to be at some relative distance d vis-á-vis the Förster distance (distance of 50% optimal resonance transfer). Each ith configuration is expected to induce d(i) relative distance. The modulation of the FRET output is modeled as the standard $6^{th}$-order response, $E = 1/(1+d(i)^6)$. Therefore, the expected Blinker signal at a particular k-mer frame of the target sequence is computed as $$B = \sum_{i}^{2^n} 1/(1+d(i)^6) \cdot P(i),$$

i.e., the expected FRET energy over the probability of the PNA:RNA duplex configurations. The parameters of the model can be estimated by a fit to the actual data measurements. The parameters will be numerically optimized by a least-square fit of the peak distribution and the peak transit time (the preliminary data was generated with a fit to the peak distribution).

Figure 31:
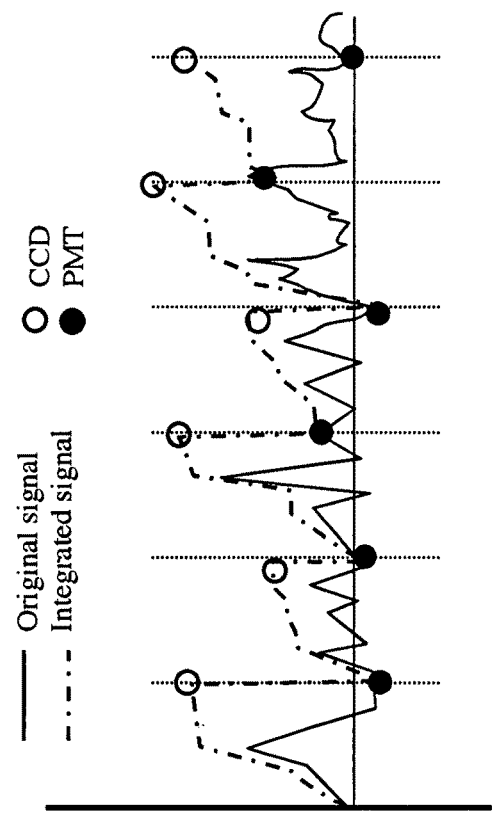
FIG. 31 depicts a model of Blinker signal (solid line) and expected signal when the original signal is integrated (dashed line) within discrete sampling intervals (indicated by dotted vertical lines). The open circles indicate values obtained from integrated signals and filled circles show values obtained from the original signal. Integrated signals are expected to be less sensitive to phase shift problems. PMT=photo multiplier tube. CCD=charge-coupled device.

The potential experimental measurement of a target sequence is a function of the FRET signal, movement across the target sequence by the polymerase, and the detection device. In particular, the important parameter is the temporal response of the detection device and the sampling interval in relation to the movement across the target sequence (governed by the processivity of the polymerase). A light collection device with a fast temporal response such as a Photo Multiplier Tube (PMT) will produce a shuttered time-slice signal that is close to the actual value at the sampling point; while, a device that integrates the collected light until sampling (e.g., CCD) will generate discrete values that are sums over intervals (FIG. 31). In general, a device that integrates the signal will be less sensitive to time domain errors (jitters). The Blinker signal will be modeled by incorporating both an integration model and a time-slice model. A suite of Perl/C++ programs has been already implemented with both the FRET signal and detector response models.

Matching Probe Blinker Signal To Target Blinker Signal: The probe Blinker signal from experimental measurements consists of a vector of numbers corresponding to the FRET output at discrete time intervals (sampling periods). An in silico Blinker signal from the library of target sequences also consists of a vector of numbers. The next step in the analysis is to compute a measure of match between the probe and target vectors and determine the best matching target. The match computation cannot be carried out as a simple vector-to-vector correlation because of inherent errors and biases in the Blinker signal production. The probe signal has three types of potential errors: error in FRET amplitude (e.g., due to duplex fluctuations), error in the time domain (called "jitter", due to processivity of the polymerase), and catastrophic error (e.g., dust, enzyme failure, etc). Bias in the Blinker signal arises from the fact that the measured values correspond to unknown frames of the probe sequence and each transcription event potentially runs into subsequent rounds of transcription without a clear boundary in the output signal; a Blinker signal is in an unknown phase and potentially concatenated with additional copies of the signal, again at unknown phases. Thus, the matching algorithm must be robust to all the error types as well as the phase shift/concatenation problem.

Figure 32:
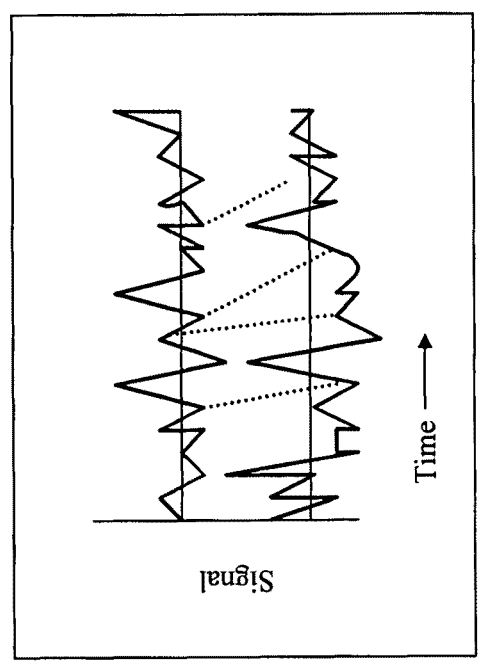
FIG. 32 depicts a representative alignment by a Constrained Local Dynamic Time Warp algorithm between two time series (dashed lines), allowing for varying degrees of time dilations.

To solve the above problems, a Constrained Local Dynamic Time Warp (CL-DTW) algorithm has been developed for signal matching. Dynamic Time Warp (DTW) is an algorithm developed in speech signal processing that has also been used for gene expression time series analysis. Similar to standard sequence alignment algorithms, the goal of the DTW algorithm is to find a best matching alignment between two sets of time series. Insertion and deletion in a DTW alignment can be interpreted as time domain jitter in either of the two time series (FIG. 32). The majority of the Blinker signal consists of background low-amplitude fluctuations interspersed with large peak deviations (see FIG. 30). Thus, the information density relevant to time alignment is low in most of the sequence, requiring the addition of an external regularity constraint. In the preliminary data, a simple constraint was implemented where the time domain jitter was limited to a maximum of Q time steps, where Q is a user-defined parameter (Q=2 in the preliminary data). Other constraints, such as the local path continuity constraints, will also be implemented. The form of the constraint imposes a tradeoff. If a strong constraint is applied, false-positive matches are reduced at the risk of missing true matches (false-negative) between signals with large amount of jitter or catastrophic error. The algorithm will be tuned from a collection of well-defined experimental data.

Because of the phase/concatenation problem described above, a global alignment is not expected to be informative for finding matches between probe and target. A local DTW algorithm was implemented by setting the dynamic programming table value to zero whenever the computed value falls below a critical value (computed from matching the signal to a constant), similar to the Smith-Waterman algorithm for sequence alignment.

Statistical Assessment of Blinker Signal Match: Once the probe signal and target signal is aligned using the CL-DTW procedure, a score has to be computed for the quality of the match. There are many possible scoring schemes. One possibility is to use the scoring scheme of the alignment procedure directly—this is often not likely to be optimal; the key goal of the alignment procedure is to obtain time-domain matches and not to assess the likelihood of two Blinker signals having the same sequence basis. In the preliminary trials, the use of discrete scores, sum-of-diagonal scores, chi-square weighted scores and number of matches divided by frame size, among others, have been investigated. Within the limited set of experimental data, reasonable performance was found with a scoring scheme that involves a chi-square weighted distance values along the diagonal of the local alignment. The scoring scheme will continue to be tuned, once additional Blinker data is available from a variety of sequences.

There are two additional statistical procedures to be assessed for the final output. First, multiple measurements of the Blinker signal are typically obtained for the same probe, usually from different image areas; thus the score from each of the replicate signals must be summarized into an overall match score. The problem of finding the right summary is analogous to summarizing the expression level value from multiple probes in a microarray experiment (e.g., Affymetrix platform). A simple mean is not likely to be reasonable due to the potential for catastrophic error and the phase/concatenation problem. A robust estimator such as the median, percentiles, or trimmed mean is required. In the preliminary data, the 95 percentile of a distribution-normalized value was used. With more empirical data, the summary procedure will be further fine-tuned. Second, given a library of targets, it will be desirable to assign a reliability value to each match score such that the results can be stated in the form of "probe X matches target Y with probability P". This requires a probability model for the match scores. In general, analytical derivation of such a probability model will not be possible. An empirical distribution will be generated based on a sampling (or resampling) of match scores from a reference null population. In the preliminary data, the score values were compared to a random collection of unassociated transcripts. A potentially reasonable null distribution can be generated by randomly sampling pairs of transcripts in the target organism genome (e.g., the rat genome), generating a Blinker signal using the in silico model, and computing the match score.

Preliminary In vitro Blinker Data Analysis Using These Algorithms: The preliminary Blinker signals were generated from two templates, ACT (actin) and PGEM (p-GEM vector sequence). Using the computational model described, an in silico model of the Blinker signal for both of the template sequences was derived. To generate a null comparison group (called NULL from here on), 75 transcripts from the mouse genome were randomly chosen, and a library of in silico Blinker sequences for these transcripts was generated.

The experimental Blinker signal for ACT or PGEM probes was generated under various different conditions, each denoted by a unique scan id (FIG. 33). The detector molecules used, denoted peptides 1, 2 and 3 in FIG. 33, correspond to the top three detector molecules, respectively, depicted in FIG. 12. A mixture of all five chimeric T7 RNA polymerases was used. Within each scan, 25 different Regions Of Interest (ROI) were selected, yielding 25 replicate measurements for each scan. Each ROI within a scan was sampled for 100 time intervals for a total of 10 minutes. Each of the 25 ROI data within a scan was matched against the ACT, PGEM, and NULL in silico Blinker signals using the Constrained Local Dynamical Time Warp (CL-DTW) algorithm described.

(Each in silico signal was generated at various phases and time intervals calibrated from experimentally measured polymerase processivity.)

For each experimental signal, the match score against ACT and PGEM was compared against the NULL match scores and kept only if the scores were within the top 95% of the NULL match scores. The relative ratio of the match scores for ACT and PGEM was computed as log(ACT/PGEM) for a total of (up to) 25 replicate log(ACT/PGEM) values. (Most scans had substantially fewer replicate values because the scores failed the comparison to the null distribution.) The replicate scores were examined for the best value favoring the ACT assignment (positive values) and the best values favoring the PGEM assignment (negative values). If the difference between the two best values exceeded a critical value (i.e., there was sufficient support for one or the other assignment), the best value was used to call an experimental scan as matching ACT or PGEM. If the critical value was not exceeded or if none of the replicates yielded match scores better than 95% of the null, no assignment was given.

FIG. 33 shows the results of this procedure for 14 scans, yielding 12 decisions and 2 no decision (scans 5 and 18). For the 12 decisions, 9 correct results (scans 1, 2, 6, 10, 13, 14, 25, 26, and 30) were obtained and 3 incorrect results (scans 17, 22 and 29). Assuming a binomial distribution and 50% probability of correct call, the probability of obtaining 9 or more correct calls in 12 trials by chance is 0.019, suggesting that experimental probe values can be assigned to the correct template with statistical significance. The current results were obtained by fine-tuning the parameters of the detection algorithm on the same dataset, thus the p-value must be interpreted with caution. New experiments will tune the algorithm using independent data sets for training and testing.

Example 5

In Vivo RNA Profiling in Differentially Stimulated Neurons

Figure 24:
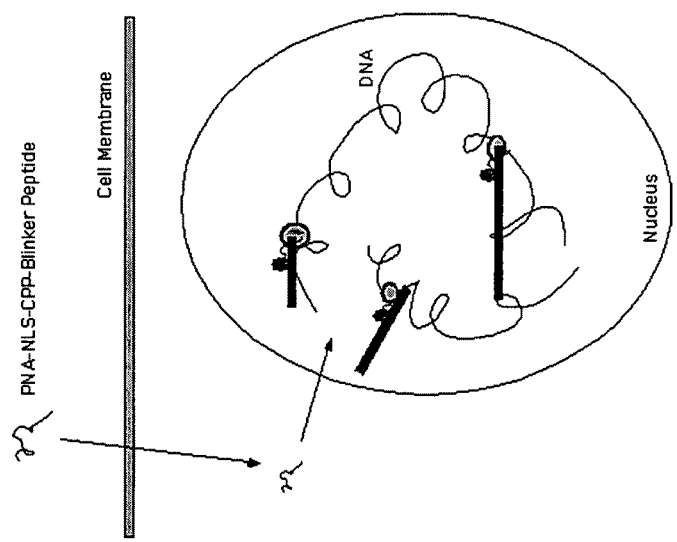
FIG. 24 is a schematic image depicting the in vivo detection of transcription by a detector molecule and chimeric RNA polymerase.

The in vivo detector molecules of the present invention comprise a CPP, an α-PAK sequence (Manser et al., 1998, Mol. Cell. 1: 183-192), a nuclear localization sequence, a linker and the PNA. The nuclear localization sequence is necessary to direct the detector molecule into the nucleus. The ability of the detector molecule to enter the cell and nucleus allows the in vivo detection of nuclear transcription in neurons and other cells known in the art that are stimulated such that the transcription patterns of different morphological sites can be assessed (FIG. 24).

The detection of in vivo transcription requires the introduction of the detector molecule into live cells. This is accomplished using cell penetrating peptides. The class of peptides comprising the CPPs is well known in the art (Hallbrink et al., 2001, Biochim. Biophys. Acta. 1515:101-109; Jarver, 2004, Drug Discov. Today 9: 395-402; Pooga et al., 2001 Curr. Cancer Drug Targets 1: 231-239; Pooga et al., 2001, FASEB J. 15: 1451-1453; Pooga et al., 1998, FASEB J. 12: 67-77). The CPP crosses the cell membrane and concentrates in the neuronal cell soma and dendrites. These data are the first showing that CPPs will transport into live neurons and demonstrate that the CPP-coupled detector molecule can penetrate a cell for use in the present invention.

Introduction of the detector molecule into a cell can be accomplished using the inherent properties of a CPP, or, alternatively, can be introduced to a cell using laser pulse irradiation to form transient pores in cell membranes together so that exogenous mRNA, proteins or DNA can diffuse into selected cells. The core technology consists of the use of a high-energy pulsed laser to introduce transient pores in cell membranes together with the application of mRNA, or other genetic or non-genetic materials to modify the function of living cells. Preliminary experiments demonstrate that the assay is 100% efficient in transient RNA introduction into cells as observed by RNA translation.

Specifically, two independent lasers, one for photoporation the other for imaging, are used, and their beams are combined through a common microscope head. This permits visualization of a field of cells and selection of the region for photoporation. During photoporation an extracellular dye or label is included with the mRNA, permitting immediate feedback about the success of photoporation.

It is characteristically quite difficult to introduce DNA or RNA into neurons. When combining photoporation with an mRNA application, routine expression of the encoded protein is possible. As an example, GFP mRNA is introduced into the bathing saline of cultured hippocampal neurons. The cells are imaged using the presence of an extracellular contrast agent, Alexa 568, together with two-photon imaging. After identifying the cell of choice, photoporation pulses are delivered from a separate laser (720 nm) that briefly leads to pore formation in the cell to allow the extracellular dye and mRNA to enter the cell. The cell is immediately labeled with the Alexa dye, and after hours expresses the protein encoded by the mRNA. This photoporation approach has proven repeatedly successful and can be used to deliver a detector molecule to a cell.

Varying the energy of laser excitation, the time of excitation and the concentration of the detector molecule will allow intracellular entry of the detector molecule. Photobleaching of the fluorescent moieties on the detector molecule should not be a factor since the photoporation occurs over microseconds.

A cell or tissue that in which real-time in vivo transcription analysis is to occur can be transfected to express a chimeric RNA polymerase in a cell or tissue. A chimeric RNA polymerase that has been cloned in the Gateway cloning system is shuttled into the mammalian expression vector that contains a CMV mammalian promoter. This is a strong promoter giving rise to a high level of expression of transgenes under its control. The relative ratio of chimeric RNA polymerase to endogenous RNA polymerase will have a bearing on the ability to detect nuclear transcription. If there is too much endogenous polymerase then the chimeric RNA polymerase may not bind to activated genes while if there is too much chimeric RNA polymerase relative to endogenous RNA polymerase, there might be dispersed of a signal (multiple RNA polymerases on one gene) on a single gene giving rise to an uninterpretable blinking signal. Bioinformatics analysis will aid in identifying the specific signal. In addition, the amount of chimerc RNA polymerase made in transfected cells can be titrated by using other promoters disclosed herein, or by using inducible promoters, including, but not limited to, a tetracycline/doxycycline inducible promoter, such as the Tet-on promoter system (Clontech, Palo Alto, Calif.).

Once the detector molecule is taken up by the cells, a transcriptional blinking signal may be generated before the sample can be imaged. Consequently, it may be necessary to slow down the transcriptional process so that the blinking can occur in a concerted manner. If this is necessary then the cultures are cooled from 37° C. to lower temperatures by 2° increments to determine the proper balance between the ability to detect transcription and the temperature necessary to keep the cells physiologically viable and responsive to stimulation.

The imaging of the detectable blinking signal within the cellular nucleus may require rapid manipulation of the focal plane, which can be aided with the use of a highly sensitive back-thinned multiplicative gain camera (Cascade 512B Camera, Photometrics, Tucson, Ariz.).

The FRET signal from the in vivo detector molecule can depend upon the length of the spacer region between the fluorescent moieties. In a linear α-helix, a distance of 10-20 amino acids appears to be ideal for FRET to occur. Shorter spacer regions, while permitting FRET, increase the ability to detect differences in fluorescent polarity. In addition to FRET detection the detector molecule of the present invention permits detection in differences of fluorescence polarization (Bell et al. 2002, Biophys. J. 83: 1050-1073; Haustein et al., 2004, Curr. Opin. Struct. Biol. 14: 531-540, van der Heide et al., 2000 Biophys J., 78: 2138-2150). Fluorescence polarity is detectable when two fluorescent molecules interact, essentially through planar interactions of their resonant ring structures. Two fluorescent moieties that are free to rotate around single covalent bonds will orient themselves to increase stacking energy and when this is perturbed changes in polarization are observed. Polarization signals are increased and noise decreased when there is more stability to one of the fluorescent molecules. The detector molecule of the present invention, especially those detector molecules used in in vivo applications, can comprise a fluorescent molecule covalently attached to the peptide through two linkages, as disclosed elsewhere herein. This fluorescent compound can be, for example, bis-(N-iodoacetyl(piperazinyl)sulfonerhodamine, which has been used extensively in the art to assess fluorescent polarity induced changes due to cytoskeletal protein movements.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A method of detecting transcription of a DNA molecule, the method comprising contacting a cell with a detector molecule and a chimeric RNA polymerase molecule comprising a detector binding domain that specifically binds to the detector molecule, wherein the detector molecule and the chimeric RNA polymerase molecule localize to the nucleus of the cell;
wherein the detector molecule comprises;
   a) a chimeric RNA polymerase binding domain (CRPBD) capable of binding to the detector binding domain,
   b) a peptide nucleic acid (PNA) complementary to a portion of an RNA molecule; and
   c) a signaling moiety,
   and wherein when the chimeric RNA polymerase transcribes the DNA to produce a nascent RNA molecule, the PNA binds to the nascent RNA molecule and a signal is emitted by the detector molecule, and
   detecting the signal, thereby detecting transcription of the DNA molecule.

2. The method of claim 1, wherein the detector molecule further comprises a cell penetrating peptide.

3. The method of claim 1, wherein the detector binding domain is selected from the group consisting of an SH3 domain and a leucine zipper.

4. The method of claim 1, wherein the CRPBD is selected from the group consisting of an α-PAK domain and a leucine zipper.

5. The method of claim 2, wherein the cell penetrating peptide is selected from the group consisting of a transportan peptide (TP), a TP10 peptide, a pVEC peptide, a penetratin peptide, a tat fragment peptide, a signal sequence based peptide, and an amphiphilic model peptide.

6. The method of claim 1, wherein the signaling moiety comprises a fluorescent molecule.

7. The method of claim 6, wherein the fluorescent molecule is selected from the group consisting of ReAsH, bis-((N-iodoacetyl)piperazinyl)sulfonerhodamine (BSR), Cy3B, Cy5, tetramethylrhodamine and fluorescein.

8. The method of claim 1, wherein the PNA is complementary to a di-nucleotide or a tri-nucleotide of the nascent RNA molecule.

9. The method of claim 8, wherein the PNA is complementary to a tri-nucleotide of the nascent RNA molecule.

10. The method of claim 9, wherein the tri-nucleotide has the nucleic acid sequence CAC.

11. The method of claim 1, wherein the chimeric RNA polymerase is a chimeric RNA polymerase II.

12. The method of claim 1, wherein the chimeric RNA polymerase is a chimeric T7 RNA polymerase.

13. The method of claim 1, wherein the signal is a fluorescent resonance energy transfer (FRET) signal or a polarity change signal.

14. The method of claim 1, wherein the cell is an eukaryotic cell.

15. The method of claim 1, wherein the cell is in an animal.

16. The method of claim 15, wherein the animal is a mammal.

17. A method of detecting the transcription of a nucleic acid molecule, the method comprising
contacting a cell with a detector molecule and a chimeric enzyme that transcribes a nucleic acid molecule, wherein the chimeric enzyme comprises a detector binding domain that specifically binds the detector molecule, wherein the detector molecule and the chimeric enzyme localize to the nucleus of the cell, wherein the detector molecule comprises:
a) a chimeric enzyme binding domain (CEBD) capable of binding to the detector binding domain,
b) a PNA complementary to a portion of a nucleic acid molecule; and
c) a signaling moiety,
and wherein when the chimeric enzyme transcribes a nucleic acid, the PNA binds to a nascent nucleic acid molecule emerging from the enzyme and a signal is emitted by the detector molecule, and
detecting the signal, thereby detecting transcription of a nucleic acid molecule.

18. The method of claim 17, wherein the detector molecule further comprises a cell penetrating peptide.

19. The method of claim 17, wherein the detector binding domain is selected from the group consisting of an SH3 domain and a leucine zipper.

20. The method of claim 17, wherein the CEBD is selected from the group consisting of an α-PAK domain and a leucine zipper.

21. The method of claim 18, wherein the cell penetrating peptide is selected from the group consisting of a transportan peptide (TP), a TP10 peptide, a pVEC peptide, a penetratin peptide, a tat fragment peptide, a signal sequence based peptide, and an amphiphilic model peptide.

22. The method of claim 17, wherein the signaling moiety comprises a fluorescent molecule.

23. The method of claim 22, wherein the fluorescent molecule is selected from the group consisting of ReAsH, bis-((N-iodoacetyl)piperazinyl)sulfonerhodamine (BSR), Cy3B, Cy5, and fluorescein.

24. The method of claim 17, wherein the PNA is complementary to a di-nucleotide or a tri-nucleotide portion of a nucleic acid molecule.

25. The method of claim 24, wherein the PNA is complementary to a tri-nucleotide portion of a nucleic acid molecule.

26. The method of claim 25, wherein the tri-nucleotide has the nucleic acid sequence CAC.

27. The method of claim 17, wherein the chimeric enzyme that transcribes a nucleic acid molecule is a chimeric RNA polymerase II.

28. The method of claim 17, wherein the chimeric enzyme that transcribes a nucleic acid molecule is a chimeric T7 RNA polymerase.

29. The method of claim 17, wherein the signal is fluorescent resonance energy transfer (FRET) signal or a polarity change signal.

30. The method of claim 17, wherein the cell is an eukaryotic cell.

31. The method of claim 17, wherein the cell is in an animal.

32. The method of claim 31, wherein the animal is a mammal.

33. A method of identifying a nucleic acid that is transcribed, the method comprising
contacting a cell with a detector molecule and a chimeric enzyme that transcribes a nucleic acid molecule, wherein the chimeric enzyme comprises a detector binding domain that specifically binds the detector molecule, wherein the detector molecule and the chimeric enzyme localize to the nucleus of the cell, wherein the detector molecule comprises:
a) a chimeric enzyme binding domain (CEBD) capable of binding to the detector binding domain,
b) a PNA complementary to a portion of the nucleic acid molecule; and
c) a signaling moiety,
and wherein when the chimeric enzyme transcribes the nucleic acid, the PNA binds to a nascent nucleic acid molecule emerging from the enzyme and a signal is emitted by the detector molecule,
detecting the signal, and
identifying the nucleic acid molecule transcribed using a constrained local dynamic time warp algorithm to match the signal detected to a library of signals associated with specific sequences, thereby identifying the nucleic acid that is transcribed.

* * * * *